US011308618B2

(12) United States Patent
Connor

(10) Patent No.: US 11,308,618 B2
(45) Date of Patent: Apr. 19, 2022

(54) HEALTHY-SELFIE(TM): A PORTABLE PHONE-MOVING DEVICE FOR TELEMEDICINE IMAGING USING A MOBILE PHONE

(71) Applicant: Robert A. Connor, St. Paul, MN (US)

(72) Inventor: Robert A. Connor, St. Paul, MN (US)

(73) Assignee: Holovisions LLC, St. Paul, MN (US)

( * ) Notice: Subject to any disclaimer, the term of this patent is extended or adjusted under 35 U.S.C. 154(b) by 0 days.

(21) Appl. No.: 17/404,174

(22) Filed: Aug. 17, 2021

(65) Prior Publication Data

US 2022/0005191 A1 Jan. 6, 2022

Related U.S. Application Data

(63) Continuation-in-part of application No. 16/706,111, filed on Dec. 6, 2019, now Pat. No. 11,176,669.

(60) Provisional application No. 62/833,761, filed on Apr. 14, 2019.

(51) Int. Cl.
*G06T 7/00* (2017.01)
*G16H 40/67* (2018.01)
*H04B 1/3877* (2015.01)
*H04M 1/04* (2006.01)

(52) U.S. Cl.
CPC .......... *G06T 7/0012* (2013.01); *G16H 40/67* (2018.01); *H04B 1/3877* (2013.01); *H04M 1/04* (2013.01); *G06T 2207/30196* (2013.01)

(58) Field of Classification Search
CPC ........ G06T 7/0012; G06T 2207/30196; G16H 40/67; H04B 1/3877; H04M 1/04
See application file for complete search history.

(56) References Cited

U.S. PATENT DOCUMENTS

| | | | |
|---|---|---|---|
| 5,016,173 A | 5/1991 | Kenet et al. | |
| 6,873,340 B2 | 3/2005 | Luby | |
| 6,925,357 B2 | 8/2005 | Wang et al. | |
| 7,142,945 B2 | 11/2006 | Wang et al. | |
| 7,142,947 B2 | 11/2006 | Wang et al. | |
| 7,158,860 B2 | 1/2007 | Wang et al. | |
| 7,161,322 B2 | 1/2007 | Wang et al. | |
| 7,162,063 B1 | 1/2007 | Craine et al. | |
| 7,164,969 B2 | 1/2007 | Wang et al. | |
| 7,164,970 B2 | 1/2007 | Wang et al. | |
| 7,171,286 B2 | 1/2007 | Wang et al. | |
| 7,218,992 B2 | 5/2007 | Wang et al. | |
| 8,638,986 B2 | 1/2014 | Jiang et al. | |
| 8,718,837 B2 | 5/2014 | Wang et al. | |
| 8,755,053 B2 | 6/2014 | Fright et al. | |
| 8,965,579 B2 | 2/2015 | Wang et al. | |

(Continued)

OTHER PUBLICATIONS

Ashique, 2015, "Clinical Photography in Dermatology Using Smartphones: An Overview," Indian Dermatology Online Journal, Jun. 3, 2015, 158.

(Continued)

*Primary Examiner* — Christopher M Brandt

(57) ABSTRACT

This invention is a portable phone-moving device to guide medical imaging using a mobile phone or other camera-enabled mobile device. The device automatically moves the phone or other mobile device over a selected portion of a person's body to guide the capturing of phone images of that portion from different angles and/or distances for medical imaging purposes.

20 Claims, 24 Drawing Sheets

(56) References Cited

U.S. PATENT DOCUMENTS

| | | |
|---|---|---|
| 9,007,433 B2 | 4/2015 | Ozcan et al. |
| 9,042,967 B2 | 5/2015 | Dacosta et al. |
| 9,161,716 B2 | 10/2015 | Estocado |
| 9,179,844 B2 | 11/2015 | Fright et al. |
| 9,285,323 B2 | 3/2016 | Burg et al. |
| 9,377,295 B2 | 6/2016 | Fright et al. |
| 9,469,030 B2 | 10/2016 | Wang et al. |
| 9,607,380 B2 | 3/2017 | Burg et al. |
| 9,674,407 B2 | 6/2017 | Gupta et al. |
| 9,696,897 B2 | 7/2017 | Garcia |
| 9,818,193 B2 | 11/2017 | Smart |
| 9,861,285 B2 | 1/2018 | Fright et al. |
| 9,863,811 B2 | 1/2018 | Burg |
| 9,955,910 B2 | 5/2018 | Fright et al. |
| 9,974,612 B2 | 5/2018 | Pinter et al. |
| 10,146,909 B2 | 12/2018 | Dimov et al. |
| 10,157,477 B2 | 12/2018 | Chen |
| 10,267,743 B2 | 4/2019 | Burg et al. |
| 10,362,984 B2 | 7/2019 | Adiri et al. |
| 10,559,081 B2 | 2/2020 | Omer et al. |
| 10,755,438 B2 | 8/2020 | Chen |
| 10,948,352 B2 | 3/2021 | Burg et al. |
| 10,991,096 B2 | 4/2021 | Adiri et al. |
| 11,026,624 B2 | 6/2021 | Adiri et al. |
| 11,026,634 B2 | 6/2021 | De Brouwer et al. |
| 11,030,778 B2 | 6/2021 | Burg et al. |
| 2003/0085908 A1 | 5/2003 | Luby |
| 2004/0019269 A1 | 1/2004 | Schaefer et al. |
| 2004/0059199 A1 | 3/2004 | Thomas et al. |
| 2004/0220464 A1 | 11/2004 | Benninger et al. |
| 2007/0112464 A1 | 5/2007 | Wang et al. |
| 2009/0093688 A1 | 4/2009 | Mathur |
| 2010/0091104 A1 | 4/2010 | Sprigle et al. |
| 2010/0271470 A1 | 10/2010 | Stephan et al. |
| 2011/0013006 A1 | 1/2011 | Uzenbajakava et al. |
| 2011/0216204 A1 | 9/2011 | Elwell et al. |
| 2012/0035469 A1 | 2/2012 | Whelan et al. |
| 2012/0197439 A1 | 8/2012 | Wang et al. |
| 2012/0197464 A1 | 8/2012 | Wang et al. |
| 2012/0218379 A1 | 8/2012 | Ozcan et al. |
| 2012/0259229 A1 | 10/2012 | Wang et al. |
| 2013/0053677 A1 | 2/2013 | Schoenfeld |
| 2013/0128223 A1 | 5/2013 | Wood et al. |
| 2013/0331708 A1 | 12/2013 | Estocado et al. |
| 2014/0029815 A1 | 1/2014 | Kadir et al. |
| 2014/0139616 A1 | 5/2014 | Pinter et al. |
| 2014/0155755 A1 | 6/2014 | Pinter et al. |
| 2014/0257058 A1 | 9/2014 | Clarysse et al. |
| 2014/0300722 A1 | 10/2014 | Garcia |
| 2014/0313303 A1 | 10/2014 | Davis et al. |
| 2015/0002606 A1 | 1/2015 | Hyde et al. |
| 2015/0036043 A1 | 2/2015 | Markovic et al. |
| 2015/0044098 A1 | 2/2015 | Smart et al. |
| 2015/0119652 A1 | 4/2015 | Hyde et al. |
| 2015/0119721 A1 | 4/2015 | Pedersen et al. |
| 2015/0150457 A1 | 6/2015 | Wu et al. |
| 2015/0201511 A1* | 7/2015 | Lee .................. H04M 1/04 361/679.55 |
| 2015/0278431 A1 | 10/2015 | Hyde et al. |
| 2015/0278480 A1 | 10/2015 | Hyde et al. |
| 2015/0308961 A1 | 10/2015 | Burg et al. |
| 2015/0313484 A1 | 11/2015 | Burg et al. |
| 2015/0359458 A1 | 12/2015 | Erickson et al. |
| 2015/0379735 A1 | 12/2015 | Lim et al. |
| 2016/0042513 A1 | 2/2016 | Yudovsky et al. |
| 2016/0163028 A1 | 6/2016 | Xu et al. |
| 2016/0206205 A1 | 7/2016 | Wu et al. |
| 2016/0248994 A1 | 8/2016 | Liu |
| 2016/0294996 A1* | 10/2016 | Yen .................. H04M 1/04 |
| 2017/0000351 A1 | 1/2017 | Fright et al. |
| 2017/0053073 A1 | 2/2017 | Allen et al. |
| 2017/0098137 A1 | 4/2017 | Burg et al. |
| 2017/0099449 A1 | 4/2017 | Kang et al. |
| 2017/0118404 A1 | 4/2017 | Song et al. |
| 2017/0229149 A1 | 8/2017 | Rothschild et al. |
| 2017/0293297 A1 | 10/2017 | Kim et al. |
| 2017/0315108 A1 | 11/2017 | Yoon et al. |
| 2017/0316155 A1 | 11/2017 | Fairbairn et al. |
| 2017/0316582 A1 | 11/2017 | Chen |
| 2017/0345183 A1 | 11/2017 | Chen |
| 2018/0028108 A1 | 2/2018 | Shluzas et al. |
| 2018/0039387 A1 | 2/2018 | Cheong et al. |
| 2018/0074636 A1 | 3/2018 | Lee et al. |
| 2018/0198982 A1 | 7/2018 | Lee et al. |
| 2018/0199856 A1 | 7/2018 | Tiwari et al. |
| 2018/0218637 A1 | 8/2018 | Lee et al. |
| 2018/0220952 A1 | 8/2018 | Lee et al. |
| 2018/0246591 A1 | 8/2018 | Huijser et al. |
| 2018/0249062 A1 | 8/2018 | Jin et al. |
| 2018/0252585 A1 | 9/2018 | Burg et al. |
| 2018/0263703 A1 | 9/2018 | Pinter et al. |
| 2018/0279943 A1 | 10/2018 | Budman et al. |
| 2018/0289334 A1 | 10/2018 | De Brouwer et al. |
| 2018/0293350 A1 | 10/2018 | Dimov et al. |
| 2018/0302564 A1 | 10/2018 | Liu et al. |
| 2018/0330522 A1 | 11/2018 | Pedersen et al. |
| 2018/0352150 A1 | 12/2018 | Purwar et al. |
| 2018/0357763 A1 | 12/2018 | Pedersen et al. |
| 2018/0374215 A1 | 12/2018 | Omer et al. |
| 2019/0008694 A1 | 1/2019 | Piotrowski et al. |
| 2019/0028634 A1 | 1/2019 | Koehler et al. |
| 2019/0028674 A1 | 1/2019 | Smits et al. |
| 2019/0038135 A1 | 2/2019 | Lee et al. |
| 2019/0050988 A1 | 2/2019 | Dimov et al. |
| 2019/0083025 A1 | 3/2019 | Aung et al. |
| 2019/0141271 A1 | 5/2019 | Kang et al. |
| 2019/0244566 A1 | 8/2019 | Kim et al. |
| 2019/0251710 A1 | 8/2019 | Park et al. |
| 2019/0281204 A1 | 9/2019 | Darty et al. |
| 2019/0290187 A1 | 9/2019 | Adiri et al. |
| 2019/0298183 A1 | 10/2019 | Burg et al. |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0320969 A1 | 10/2019 | Levi et al. |
| 2019/0325914 A1 | 10/2019 | Rothschild et al. |
| 2019/0343396 A1 | 11/2019 | Khosravi et al. |
| 2019/0350535 A1 | 11/2019 | Zhao et al. |
| 2019/0391236 A1 | 12/2019 | Downing et al. |
| 2019/0391729 A1 | 12/2019 | Josephson et al. |
| 2020/0041761 A1 | 2/2020 | Seo et al. |
| 2020/0053298 A1 | 2/2020 | Liu et al. |
| 2020/0059596 A1 | 2/2020 | Yoo et al. |
| 2020/0085164 A1 | 3/2020 | Tamir et al. |
| 2020/0105013 A1 | 4/2020 | Chen |
| 2020/0126227 A1 | 4/2020 | Adiri et al. |
| 2020/0126283 A1 | 4/2020 | Van Vuuren et al. |
| 2020/0126593 A1 | 4/2020 | Rothschild et al. |
| 2020/0170564 A1 | 6/2020 | Jiang et al. |
| 2020/0185073 A1 | 6/2020 | De Brouwer et al. |
| 2020/0186782 A1 | 6/2020 | Bigioi et al. |
| 2020/0193580 A1 | 6/2020 | Mccall et al. |
| 2020/0193597 A1 | 6/2020 | Fan et al. |
| 2020/0196962 A1 | 6/2020 | Zhao et al. |
| 2020/0211193 A1 | 7/2020 | Adiri et al. |
| 2020/0211228 A1 | 7/2020 | Adiri et al. |
| 2020/0225166 A1 | 7/2020 | Burg et al. |
| 2020/0241290 A1 | 7/2020 | Breese et al. |
| 2020/0279659 A1 | 9/2020 | De Brouwer et al. |
| 2020/0280661 A1 | 9/2020 | Barnes et al. |
| 2020/0293887 A1 | 9/2020 | De Brouwer et al. |
| 2020/0310083 A1 | 10/2020 | Kim et al. |
| 2020/0330028 A1 | 10/2020 | Nejati et al. |
| 2020/0342987 A1 | 10/2020 | De Brouwer et al. |
| 2020/0348493 A1 | 11/2020 | Seo et al. |
| 2020/0352515 A1 | 11/2020 | Godavarty et al. |
| 2020/0352686 A1 | 11/2020 | Yancey et al. |
| 2020/0364862 A1 | 11/2020 | Dacosta et al. |
| 2020/0374437 A1 | 11/2020 | Kang et al. |
| 2020/0381127 A1 | 12/2020 | Silverman et al. |
| 2020/0401830 A1 | 12/2020 | Zhu et al. |
| 2020/0404164 A1 | 12/2020 | Wu et al. |
| 2021/0004995 A1 | 1/2021 | Burg et al. |
| 2021/0007606 A1 | 1/2021 | Su et al. |

(56) References Cited

U.S. PATENT DOCUMENTS

| | | |
|---|---|---|
| 2021/0012130 A1 | 1/2021 | Park et al. |
| 2021/0029300 A1 | 1/2021 | Lee et al. |
| 2021/0077233 A1 | 3/2021 | Yancey et al. |
| 2021/0082094 A1 | 3/2021 | Mccall et al. |
| 2021/0084216 A1 | 3/2021 | Choi et al. |
| 2021/0124424 A1 | 4/2021 | Sandhan et al. |
| 2021/0127989 A1 | 5/2021 | Atamanuk et al. |
| 2021/0128021 A1 | 5/2021 | Emalfarb et al. |
| 2021/0132795 A1 | 5/2021 | Kurbanova et al. |
| 2021/0136263 A1 | 5/2021 | Pitman |
| 2021/0142888 A1 | 5/2021 | Adiri et al. |
| 2021/0145359 A1 | 5/2021 | Hunt et al. |
| 2021/0161621 A1 | 6/2021 | Salah et al. |
| 2021/0186658 A1 | 6/2021 | Salah et al. |
| 2021/0201479 A1 | 7/2021 | Fan et al. |
| 2021/0203871 A1 | 7/2021 | Kang et al. |
| 2021/0217797 A1 | 7/2021 | Hashiguchi et al. |
| 2021/0218923 A1 | 7/2021 | Yoda et al. |
| 2021/0225032 A1 | 7/2021 | Hain et al. |
| 2021/0225492 A1 | 7/2021 | Fairbairn et al. |
| 2021/0225509 A1 | 7/2021 | Wang et al. |
| 2021/0225516 A1 | 7/2021 | Liu et al. |
| 2021/0226906 A1 | 7/2021 | Ryu et al. |
| 2021/0227019 A1 | 7/2021 | Soon-Shiong et al. |
| 2021/0227413 A1 | 7/2021 | Yang et al. |

OTHER PUBLICATIONS

Burns, 2015, "Digital Photography and the Medical Selfie," Journal of Participatory Medicine, Feb. 11, 2015, 7, e3.

Burns, 2019, "Creating Consumer-Generated Health Data: Interviews and a Pilot Trial Exploring How and Why Patients Engage," Journal of Medical Internet Research, 2019, 21(6), e12367.

Coleman, 2019, "Cell Phone Based Colorimetric Analysis for Point-of-Care Settings," The Analyst, Jan. 28, 2019, 144(6), 1935-1947.

Diethei, 2018, "Using Smartphones to Take Eye Images for Disease Diagnosis in Developing Countries," Proceedings of the Second African Conference for Human Computer Interaction: Thriving Communities (Windhoek, Namibia) (AfriCHI '18), ACM, New York, NY, Article 34.

Diethei, 2020, "Medical Selfies: Emotional Impacts and Practical Challenges," MobileHCI '20: 22nd International Conference on Human-Computer Interaction with Mobile Devices and Services, Oct. 5, 2020, 8, 1-2.

Farr, 2020, "Healthy.io, Maker of a Medical Selfie, Is Part of the New Generation of Israeli Health-Tech Companies," CNBC, Jun. 22, 2020.

Florida Atlantic Atlantic University, 2019, "Selfies to Self-Diagnosis: Algorithm Amps Up Smartphones to Diagnose Disease," Science Daily, Feb. 12, 2019.

Granot, 2008, "A New Concept for Medical Imaging Centered on Cellular Phone Technology," PloS one, 3, e2075.

Healthy.io, White White Paper, 2020, "Digitizing Wound Management: A Standardized, Evidence-Based Approach to Healing," Healthy.io, White Paper, 2020.

Lee, 2018, "Recent Trends in Teledermatology and Teledermoscopy," Dermatology Practical & Conceptual, Aug. 3, 2018, 214.

Mai, 2020, "The Effect of Perioral Scan and Artificial Skin Markers on the Accuracy of Virtual Dentofacial Integration: Stereophotogrammetry Versus Smartphone Three-Dimensional Face-Scanning," International Journal of Environmental Research and Public Health, 2020, 18(1), 229.

Otero, 2019, "Comparison of Different Smartphone Cameras to Evaluate Conjunctival Hyperaemia in Normal Subjects," Scientific Reports, Sep. 2019, 1339.

Peng, 2017, "Constructing a 3D Multiple Mobile Medical Imaging System through Service Science, Management, Engineering and Design," Systems, 2017, 5(1), 5.

Pires, 2015, "Wound Area Assessment Using Mobile Application," Biodevices, 2015.

Pivo, 2019, "Pivo Pod Get Insanely Creative Gifs, Photos, Videos," Indiegogo, campaign closed Jan. 19, 2019.

Senthilkumaran, 2021, "Simple Technique for Medical Photography in the Emergency Department During the COVID Pandemic: Say Cheese," Journal of Emergency Medicine, Letter to the Editor, May 1, 2021, 60(5), e135.

Wicklund, 2019, "mHealth Researchers Look to Make the Selfie a Health Resource," mHealth Intelligence, Aug. 9, 2019.

Wong, 2018, "Real-World Use of Telemedicine: A Picture Is Worth a Thousand Words," PMFA Journal, 5(2), Dec./Jan. 2018.

Zhou, 2012, "A Survey of Optical Imaging Techniques for Assessing Wound Healing," International Journal of Intelligent Control and Systems, Sep. 2012 17(3), 79-85.

\* cited by examiner

HEALTHY-SELFIE(TM): A PORTABLE PHONE-MOVING DEVICE FOR TELEMEDICINE IMAGING USING A MOBILE PHONE

CROSS-REFERENCE TO RELATED APPLICATIONS

This application is a continuation-in-part of U.S. patent application Ser. No. 16/706,111 entitled "System for Remote Medical Imaging using Two Conventional Smart Mobile Devices and/or Augmented Reality (AR)" filed on 2019 Dec. 6. U.S. patent application Ser. No. 16/706,111 claimed the priority benefit of U.S. provisional patent application No. 62/833,761 entitled "Mobile Devices (such as Mobile Phones) for Remote and/or Virtual Health Care" filed on 2019 Apr. 14. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to remote medical imaging using conventional mobile devices.

INTRODUCTION

There are many reasons for remote medical evaluation via electronic communication (e.g. telemedicine). With remote medical evaluation, people in low-population areas who do not have local healthcare specialists can have remote access to care from non-local specialists. Also, remote medical evaluation can help people with limited transportation to receive care from their homes and help people with busy work schedules get care at convenient times. Further, as highlighted by the recent pandemic, remote medical evaluation can help people to avoid the in-person contact which can spread contagious disease. Also, from a provider perspective, remote medical evaluation can enhance provider productivity, lower the cost of care, and broaden a provider's geographic service area.

For these reasons, as well as technological advances, there has been progress in remote medical evaluation during the past several years. The quality and functionality of internet-based medical video conferencing has improved. Mobile phones have become ubiquitous and the quality of images captured by their cameras has improved. Increasingly-sophisticated software, machine-learning, and AI programs are playing a greater role in telemedicine and virtual care portals. Accordingly, remote medical evaluation is growing.

Despite these advances, however, there are still significant challenges remote medical evaluation, especially for remote imaging. For example, when people take a picture of a portion of their body using a conventional mobile phone and send the picture to a healthcare provider for evaluation, the provider can face a number of problems when trying to evaluate the image. These potential problems include: improper distance from the phone to the body, out-of-focus image, and insufficient cues to assess the size and orientation of an area of interest; improper angle or limited number of angles between the phone and the body which make it difficult to assess three-dimensional attributes of the area; improper ambient lighting level or color, and differences in image color calibration, caused by different types of phones, which confound provider assessment of body color.

As will be discussed in the next section, some innovative companies have begun to tackle these problems with remote medical imaging for telemedicine. Some are creating customized medical devices, such as medical robots, which are used in healthcare facilities. However, thus far these customized medical devices tend to be expensive and not suited for home use. Remote medical evaluation would be greatly facilitated by a relatively low-cost technology which takes full advantage of the wide-spread use of conventional mobile devices. Some innovative companies are developing products which take advantage of conventional mobile phones for medical purposes. Their products include fiducial strips and stickers (with size markings and colors) which are placed near a person's body to improve calibration and assessment of the size, shape, and/or color of a body area in a phone-based image. Such strips and sticks are also being used as a color reference to which a color-changing medical test strip can be compared. Other innovative companies are focusing on software, machine learning, three-dimensional models, and tracking changes in a body area over time.

However, despite these innovations, there is an unmet need for portable, low-cost, and easy-to-use technology to guide remote medical imaging using conventional camera-equipped mobile phones to address the medical imaging problems noted above, especially those related to distance, angle, lighting, and color. This need is addressed by the invention (the "Healthy Selfie"™) which is disclosed herein.

REVIEW OF THE RELEVANT ART

This review of the relevant art starts with a review of patents and patent applications. U.S. Pat. No. 5,016,173 (Kenet et al., May 14, 1991, "Apparatus and Method for Monitoring Visually Accessible Surfaces of the Body") discloses an apparatus and method for in vivo monitoring of body surfaces. U.S. patent application 20030085908 (Luby, May 8, 2003, "Method and Apparatus for an Automated Reference Indicator System for Photographic and Video Images") and U.S. Pat. No. 6,873,340 (Luby, Mar. 29, 2005, "Method and Apparatus for an Automated Reference Indicator System for Photographic and Video Images") disclose an automated reference indicator system with at least one indicator patch placed near an area of interest. U.S. patent application 20040019269 (Schaefer et al., Jan. 29, 2004, "Early Detection of Inflammation and Infection Using Infrared Thermography") discloses a method for detecting inflammation using infrared thermography.

U.S. patent application 20040059199 (Thomas et al., Mar. 25, 2004, "Wound Assessment and Monitoring Apparatus and Method") discloses a wound assessment and monitoring apparatus and method for monitoring the development of wounds by patients of a health care facility. U.S. patent application 20040220464 (Benninger et al., Nov. 4, 2004, "Method and Apparatus for Carrying Out a Televisit") discloses a method of carrying out a televisit comprising acquiring the data of a patient, recording an image of at least one body zone of the patient, and transmitting the data and the image to a medical institution.

U.S. Pat. No. 6,925,357 (Wang et al., Aug. 2, 2005, "Medical Tele-Robotic System"), U.S. Pat. No. 7,142,945

(Wang et al., Nov. 28, 2006, "Medical Tele-Robotic System"), U.S. Pat. No. 7,142,947 (Wang et al., Nov. 28, 2006, "Medical Tele-Robotic Method"), U.S. Pat. No. 7,164,970 (Wang et al., Jan. 16, 2007, "Medical Tele-Robotic System"), and U.S. Pat. No. 7,218,992 (Wang et al., May 15, 2007, "Medical Tele-Robotic System") disclose a remote-controlled telemedicine robot. U.S. Pat. No. 7,158,860 (Wang et al., Jan. 2, 2007, "Healthcare Tele-Robotic System Which Allows Parallel Remote Station Observation") and U.S. Pat. No. 7,171,286 (Wang et al., Jan. 30, 2007, "Healthcare Tele-Robotic System with a Robot That Also Functions as a Remote Station") disclose a mobile medical robot which provides audio and visual information. U.S. Pat. No. 7,161,322 (Wang et al., Jan. 9, 2007, "Robot with a Manipulator Arm") discloses a robot with an arm coupled to a platform.

U.S. patent application 20070112464 (Wang et al., May 17, 2007, "Apparatus and Method for Patient Rounding with a Remote Controlled Robot") and U.S. Pat. No. 7,164,969 (Wang et al., Jan. 16, 2007, "Apparatus and Method for Patient Rounding with a Remote Controlled Robot") disclose a remote-controlled medical robot. U.S. patent applications 20120197439 (Wang et al., Aug. 2, 2012, "Interfacing with a Mobile Telepresence Robot") and U.S. patent application 20120197464 (Wang et al., Aug. 2, 2012, "Interfacing with a Mobile Telepresence Robot") and U.S. Pat. No. 8,718,837 (Wang et al., May 6, 2014, "Interfacing with a Mobile Telepresence Robot"), U.S. Pat. No. 8,965,579 (Wang et al., Feb. 24, 2015, "Interfacing with a Mobile Telepresence Robot"), and U.S. Pat. No. 9,469,030 (Wang et al., Oct. 18, 2016, "Interfacing with a Mobile Telepresence Robot") disclose a mobile telepresence robot with a drive system, a control system, an imaging system, and a mapping module.

U.S. Pat. No. 7,162,063 (Craine et al., Jan. 9, 2007, "Digital Skin Lesion Imaging System and Method") discloses detection of skin lesions using digital baseline image data of an area, a physical calibration piece near the area, and monitoring area changes. U.S. patent application 20090093688 (Mathur, Apr. 9, 2009, "System, Device, and Method for Remote Monitoring and Servicing") discloses an interface device with a built-in video camera which is configured to send video information from the built-in video camera as well as physiological information to a remote monitoring facility.

U.S. patent applications 20100091104 (Sprigle et al., Apr. 15, 2010, "Systems and Methods for the Measurement of Surfaces") and 20120035469 (Whelan et al., Feb. 9, 2012, "Systems and Methods for the Measurement of Surfaces") disclose a portable, hand-held, non-contact surface measuring system comprising an image capturing element, at least four projectable reference elements positioned parallel to one another at known locations around the image capturing element, a processing unit, and a user interface. U.S. patent application 20100271470 (Stephan et al., Oct. 28, 2010, "Method and Aparratus for Characterizing a Person's Skin Imperfections") discloses a method of characterizing a person's skin imperfections using a digital color image-taking device.

U.S. patent application 20110013006 (Uzenbajakava et al., Jan. 20, 2011, "Apparatus for Skin Imaging, System for Skin Analysis") discloses an apparatus for skin imaging which captures near-field and far-field skin images under different illumination angles. U.S. patent application 20110216204 (Elwell et al., Sep. 8, 2011, "Systems and Methods for Bio-Image Calibration") discloses products for bio-image calibration.

U.S. patent application 20120218379 (Ozcan et al., Aug. 30, 2012, "Incoherent Lensfree Cell Holography and Microscopy on a Chip") and U.S. Pat. No. 9,007,433 (Ozcan et al., Apr. 14, 2015, "Incoherent Lensfree Cell Holography and Microscopy on a Chip") disclose a system for imaging a cytological sample including a sample holder which holds a cytological sample. U.S. patent application 20120259229 (Wang et al., Oct. 11, 2012, "Apparatus and Methods for In Vivo Tissue Characterization by Raman Spectroscopy") discloses a spectrometer system for differentiating tumor lesions. U.S. patent application 20130053677 (Schoenfeld, Feb. 28, 2013, "System and Method for Wound Care Management Based on a Three Dimensional Image of a Foot") discloses a system for wound care management using a scanner configured to obtain a two-dimensional image of the plantar surface of the foot.

U.S. patent application 20130128223 (Wood et al., May 23, 2013, "Digital-Based Medical Devices") discloses a hand-held ophthalmic examination instrument which emits amber light and white light. U.S. patent application 20130331708 (Estocado et al., Dec. 12, 2013, "Diagnostic Imaging System for Skin and Affliction Assessment") and U.S. Pat. No. 9,161,716 (Estocado, Oct. 20, 2015, "Diagnostic Imaging System for Skin and Affliction Assessment") disclose a size-assessment tool which is placed near an affliction for imaging. U.S. Pat. No. 8,638,986 (Jiang et al., Jan. 28, 2014, "Online Reference Patch Generation and Pose Estimation for Augmented Reality") discloses a reference patch generated using a captured image of a planar object with two perpendicular sets of parallel lines. U.S. patent application 20140029815 (Kadir et al., Jan. 30, 2014, "Measurement System for Medical Images") discloses a method of measuring a parameter of a structure on a medical image with a measurement tool displayed on a slice of the image.

U.S. Pat. No. 8,755,053 (Fright et al., Jun. 17, 2014, "Method of Monitoring a Surface Feature and Apparatus Therefor"), U.S. Pat. No. 9,377,295 (Fright et al., Jun. 28, 2016, "Method of Monitoring a Surface Feature and Apparatus Therefor"), and U.S. Pat. No. 9,955,910 (Fright et al., May 1, 2018, "Method of Monitoring a Surface Feature and Apparatus Therefor") disclose determination of the dimensions of a surface feature by capturing an image of the surface feature and determining a scale associated with the image. U.S. patent application 20170000351 (Fright et al., Jan. 5, 2017, "Handheld Skin Measuring or Monitoring Device") and U.S. Pat. No. 9,179,844 (Fright et al., Nov. 10, 2015, "Handheld Skin Measuring or Monitoring Device") and U.S. Pat. No. 9,861,285 (Fright et al., Jan. 9, 2018, "Handheld Skin Measuring or Monitoring Device") disclose a handheld skin monitoring or measuring device with a camera and a structured light arrangement configured to project laser beams.

U.S. patent applications 20140139616 (Pinter et al., May 22, 2014, "Enhanced Diagnostics for a Telepresence Robot"), U.S. patent application 20140155755 (Pinter et al., Jun. 5, 2014, "Enhanced Diagnostics for a Telepresence Robot"), and U.S. patent application 20180263703 (Pinter et al., Sep. 30, 2018, "Enhanced Diagnostics for a Telepresence Robot"), and U.S. Pat. No. 9,974,612 (Pinter et al., May 22, 2018, "Enhanced Diagnostics for a Telepresence Robot") disclose a telepresence robot which may include an image sensor, a thermal camera, a depth sensor, and one or more systems for interacting with patients. U.S. patent application 20140257058 (Clarysse et al., Sep. 11, 2014, "Automated Personal Medical Diagnostic System, Method, and Arrangement") discloses an automated personal medical diagnostic system with at least one sensor to measure at least one physiological condition.

U.S. patent application 20140300722 (Garcia, Oct. 9, 2014, "Image-Based Measurement Tools") and U.S. Pat. No. 9,696,897 (Garcia, Jul. 4, 2017, "Image-Based Measurement Tools,") disclose using an available object (such as a coin, bank note, person of known height, sticker of known dimensions, printed object of known dimensions, or shape made of projected light) as a fiducial marker in mobile device imaging. U.S. patent application 20140313303 (Davis et al., Oct. 23, 2014, "Longitudinal Dermoscopic Study Employing Smartphone-Based Image Registration") discloses how a user can capture skin images using a smartphone and these images can be co-registered, color-corrected, and presented to the user (or a clinician) for review.

U.S. patent application 20150002606 (Hyde et al., Jan. 1, 2015, "Medical Support System Including Medical Equipment Case") discloses a medical equipment case for containing and transporting at least one article of medical equipment and a two-way audio-visual system. U.S. patent application 20150119652 (Hyde et al., Apr. 30, 2015, "Telemedicine Visual Monitoring Device with Structured Illumination") discloses a system for providing telemedicine support with structured illumination and two-way audio visual communication between a patient and a remote caregiver. U.S. patent applications 20150278431 (Hyde et al., Oct. 1, 2015, "Quantified-Self Machines and Circuits Reflexively Related to Kiosk Systems and Associated Fabrication Machines and Circuits") and 20150278480 (Hyde et al., Oct. 1, 2015, "Quantified-Self Machines and Circuits Reflexively Related to Kiosk Systems and Associated Food-And-Nutrition Machines and Circuits") disclose a system and method electronically receives user biological status information from electronically involved detection of one or more biological user conditions.

U.S. patent application 20150036043 (Markovic et al., Feb. 5, 2015, "Bioscicon's Cellphone Camera—Microscope Universal Adapter") discloses a device which simulates movement of a human examiner analyzing cytopathological specimens using a microscope. U.S. patent applications 20150044098 (Smart et al., Feb. 12, 2015, "Hyperspectral Imaging Systems, Units, and Methods") and 20190281204 (Darty et al., Sep. 12, 2019, "Hyperspectral Imager Coupled with Indicator Molecule Tracking") disclose methods and systems for concurrent imaging at multiple wavelengths. U.S. patent applications 20150119721 (Pedersen et al, Apr. 30, 2015, "System and Method for Assessing Wound"), 20180330522 (Pedersen et al., Nov. 15, 2018, "System and Method for Assessing Wound"), and 20180357763 (Pedersen et al., Dec. 13, 2018, "System and Method for Assessing Wound") disclose a wound assessing method and system.

U.S. Pat. No. 9,042,967 (Dacosta et al., May 26, 2015, "Device and Method for Wound Imaging and Monitoring") discloses a device for fluorescence-based imaging. U.S. patent applications 20150150457 (Wu et al., Jun. 4, 2015, "Method and System for Wound Assessment and Management") and U.S. patent application 20160206205 (Wu et al., Jul. 21, 2016, "Method and System for Wound Assessment and Management") disclose a system and method for determining characteristics of a wound with a first imaging sensor that obtains imaging information of a wound area and a second imaging sensor that obtains topology information of the wound area.

U.S. patent applications 20150308961 (Burg et al., Oct. 29, 2015, "Quantifying Color Changes of Chemical Test Pads Induced by Specific Concentrations of Biological Analytes Under Different Lighting Conditions") and 20190310203 (Burg et al., Oct. 10, 2019, "Quantifying Color Changes of Chemical Test Pads Induced by Specific Concentrations of Biological Analytes Under Different Lighting Conditions") and U.S. Pat. No. 9,285,323 (Burg et al., Mar. 15, 2016, "Quantifying Color Changes of Chemical Test Pads Induced Concentrations of Biological Analytes Under Different Lighting Conditions") and (Burg et al., Apr. 23, 2019, "Quantifying Color Changes of Chemical Test Pads Induced by Specific Concentrations of Biological Analytes Under Different Lighting Conditions") disclose color quantification of chemical test pads and titration of analytes under different lighting conditions.

U.S. patent applications 20150313484 (Burg et al., Nov. 5, 2015, "Portable Device with Multiple Integrated Sensors for Vital Signs Scanning") and 20190298183 (Burg et al., Oct. 3, 2019, "Portable Device With Multiple Integrated Sensors for Vital Signs Scanning") disclose a portable device with multiple integrated sensors for scanning vital signs. U.S. Pat. No. 9,607,380 (Burg et al., Mar. 28, 2017, "Methods and Apparatus for Quantifying Color Changes Induced by Specific Concentrations of Biological Analytes") discloses methods and electronic devices for performing color-based reaction testing of biological materials.

U.S. patent applications 20170098137 (Burg et al., Apr. 6, 2017, "Method, Apparatus and System for Detecting and Determining Compromised Reagent Pads by Quantifying Color Changes Induced by Exposure to a Hostile Environment") and 20200225166 (Burg et al., Jul. 16, 2020, "Method, Apparatus and System for Detecting and Determining Compromised Reagent Pads by Quantifying Color Changes Induced by Exposure to a Hostile Environment") disclose reagent test paddle with a contamination detection medium, a reference color bar, at least one chemical test medium, and a unique identifier. U.S. patent application 20180252585 (Burg et al., Sep. 6, 2018, "Precision Luxmeter Methods for Digital Cameras to Quantify Colors in Uncontrolled Lighting Environments") and U.S. Pat. No. 9,863,811 (Burg, Jan. 9, 2018, "Precision Luxmeter Methods for Digital Cameras to Quantify Colors in Uncontrolled Lighting Environments") and 10948352 (Burg et al., Mar. 16, 2021, "Precision Luxmeter Methods for Digital Cameras to Quantify Colors in Uncontrolled Lighting Environments") disclose a diagnostic system for biological samples including a diagnostic instrument and a portable electronic device.

U.S. patent application 20150359458 (Erickson et al., Dec. 17, 2015, "Smartphone-Based Apparatus and Method for Obtaining Repeatable, Quantitative Colorimetric Measurement") discloses a method for obtaining a point-of-collection, selected quantitative indicia of an analyte on a test strip using a smartphone. U.S. patent application 20150379735 (Lim et al., Dec. 31, 2015, "Remote Monitoring Framework") discloses a technology for facilitating remote monitoring using color data of a region of interest received by a computer system from a mobile device. U.S. patent application 20160042513 (Yudovsky et al., Feb. 11, 2016, "Systems and Methods for Evaluating Hyperspectral Imaging Data Using a Two Layer Media Model of Human Tissue") discloses a method for acquiring a hyperspectral imaging data set from a region of interest of a human subject using a hyperspectral imager. U.S. patent application 20160163028 (Xu et al., Jun. 9, 2016, "Method and Device for Image Processing") discloses a method comprising performing facial recognition on an image, determining a skin area to be processed, determining the locations of skin blemishes, and removing the skin blemishes in the image.

U.S. patent applications 20160248994 (Liu, Aug. 25, 2016, "Multipurpose Imaging and Display System") and 20200053298 (Liu et al., Feb. 13, 2020, "Multipurpose Imaging and Display System") disclose a multi-purpose imaging and display system including a display, a detector coupled to the display and having a field of view, and a filter communicating with the detector. U.S. patent application 20170053073 (Allen et al., Feb. 23, 2017, "System and Methods for Implementing Wound Therapy Protocols") discloses systems, methods, and apparatuses for treating a tissue site. U.S. patent applications 20170099449 (Kang et al., Apr. 6, 2017, "Electronic Device and Method for Generating Image Data"), 20190141271 (Kang et al., May 9, 2019, "Electronic Device and Method for Generating Image Data"), and 20210203871 (Kang et al., Jul. 1, 2021, "Electronic Device and Method for Generating Image Data") disclose an electronic device with an image sensor that acquires an optical signal corresponding to an object and a controller that controls the image sensor.

U.S. patent application 20170118404 (Song et al., Apr. 27, 2017, "Method for Setting Focus and Electronic Device Thereof") discloses a method and apparatus for dynamically determining an auto focusing (AF) area according to a size information of a face in a digital image processing device. U.S. Pat. No. 9,674,407 (Gupta et al., Jun. 6, 2017, "System and Method for Interactive Image Capture for a Device Having a Camera") discloses a guidance system for interactive image capture for use with a device having a camera and a camera lens. U.S. patent applications 20170229149 (Rothschild et al., Aug. 10, 2017, "System and Method for Using, Biometric, and Displaying Biometric Data"), 20190325914 (Rothschild et al., Oct. 24, 2019, "System and Method for Using, Processing, and Displaying Biometric Data"), and 20200126593 (Rothschild et al., Apr. 23, 2020, "System and Method for Using, Processing, and Displaying Biometric Data") disclose a method for processing and displaying biometric data of a user.

U.S. patent application 20170293297 (Kim et al., Oct. 12, 2017, "Electronic Apparatus and Operating Method Thereof") discloses a drone with a camera. U.S. patent application 20170315108 (Yoon et al., Nov. 2, 2017, "Rapid and Non-Destructive Detection of Infection") discloses methods and devices to identify an infection via light scatter from a tissue surface. U.S. patent applications 20170316155 (Fairbairn et al., Nov. 2, 2017, "Automatically Assessing an Anatomical Surface Feature and Securely Managing Information Related to the Same") and 20210225492 (Fairbairn et al., Jul. 22, 2021, "Automatically Assessing an Anatomical Surface Feature and Securely Managing Information Related to the Same") disclose a facility for procuring information and including image information about an anatomical surface feature.

U.S. patent applications 20170316582 (Chen, Nov. 2, 2017, "Robust Head Pose Estimation with a Depth Camera"), 20170345183 (Chen, Nov. 30, 2017, "Robust Head Pose Estimation with a Depth Camera"), and 20200105013 (Chen, Apr. 2, 2020, "Robust Head Pose Estimation with a Depth Camera") and U.S. patent Ser. No. 10/157,477 (Chen, Dec. 18, 2018, "Robust Head Pose Estimation with a Depth Camera") and 10755438 (Chen, Aug. 25, 2020, "Robust Head Pose Estimation with a Depth Camera") disclose systems and methods to estimate the pose of a human subject's head from a sequence of images received from a single depth camera.

U.S. Pat. No. 9,818,193 (Smart, Nov. 14, 2017, "Spatial Resolution Enhancement in Hyperspectral Imaging") discloses a hyperspectral imaging system and method with a pixilated imaging sensor array. U.S. patent application 20180028108 (Shluzas et al., Feb. 1, 2018, "Digital Wound Assessment Device and Method") discloses a wound assessment device with a camera, additional sensors, and image processing. U.S. patent application 20180039387 (Cheong et al., Feb. 8, 2018, "Method for Controlling Display, Storage Medium, and Electronic Device") discloses an electronic device including a flexible display.

U.S. patent application 20180074636 (Lee et al., Mar. 15, 2018, "Electronic Device and Method of Controlling Electronic Device") discloses an electronic device, a method of controlling an electronic device, and a non-transitory computer-readable recording medium. U.S. patent application 20180198982 (Lee et al., Jul. 12, 2018, "Image Capturing Method and Electronic Device") discloses methods for capturing images using camera-equipped electronic devices and electronic devices. U.S. patent application 20180199856 (Tiwari et al., Jul. 19, 2018, "Electronic Device and Method for Providing Information Related to Skin Type of Object") discloses an electronic device for providing skin type information by comparison of colors in skin images and non-skin images.

U.S. patent application 20180218637 (Lee et al., Aug. 2, 2018, "Method and Electronic Device for Providing Health Content") discloses an electronic device with a display, a processor, a communication circuit establishing communication with a server, and a memory storing a specified application. U.S. patent application 20180220952 (Lee et al., Aug. 9, 2018, "Method for Providing Skin Information and Electronic Device for Supporting the Same") discloses an electronic device to capture a portion of a user's body based on a light source device, a first camera, and a second camera, a memory configured to store a capture image by the image capture device, a display configured to emit light in a specified color at least one region based on driving at least one pixel, and at least one processor configured to be electrically connected with the image capture device, the memory, and the display.

U.S. patent application 20180246591 (Huijser et al., Aug. 30, 2018, "Method of Controlling a Mobile Device") discloses a method of controlling a mobile device by receiving a time varying current or voltage of a signal generated on the terminals of an acoustic transducer of the mobile device. U.S. patent application 20180249062 (Jin et al., Aug. 30, 2018, "Photographing Method Using External Electronic Device and Electronic Device Supporting the Same") discloses a photographing method using an external electronic device and an electronic device supporting the same. U.S. patent application 20180279943 (Budman et al., Oct. 4, 2018, "System and Method for the Analysis and Transmission of Data, Images and Video Relating to Mammalian Skin Damage Conditions") discloses analysis of medical images including one or more objects with a known shape, color characteristic, and size.

U.S. patent application 20180289334 (De Brouwer et al., Oct. 11, 2018, "Image-Based System and Method for Predicting Physiological Parameters") and U.S. patent Ser. No. 11/026,634 (De Brouwer et al., Jun. 8, 2021, "Image-Based System and Method for Predicting Physiological Parameters") disclose measuring a physiological parameter by analyzing a facial image. U.S. patent applications 20180293350 (Dimov et al., Oct. 11, 2018, "Image-Based Disease Diagnostics Using a Mobile Device") and 20190050988 (Dimov et al., Feb. 14, 2019, "Image-Based Disease Diagnostics Using a Mobile Device"), and U.S. patent Ser. No. 10/146,909 (Dimov et al., Dec. 4, 2018, "Image-Based Disease Diagnostics Using a Mobile Device") disclose a diagnostic system which performs disease diagnostic tests using optical property modifying device and a mobile device. U.S. patent application 20180302564 (Liu et al., Oct. 18, 2018, "System and Apparatus for Co-Registration and Correlation Between Multi-Modal Imagery and Method for Same") discloses an image capturing device that captures images of a first sensor that includes a first imaging modality, a second sensor that includes a first imaging modality and a third sensor that includes a second imaging modality.

U.S. patent application 20180352150 (Purwar et al., Dec. 6, 2018, "System and Method for Guiding a User to Take a Selfie") discloses systems and methods for improving the image quality of a selfie using face and landmark detection techniques and face normalization techniques. U.S. patent application 20180374215 (Omer et al., Dec. 27, 2018, "Method and System for Automated Visual Analysis of a Dipstick Using Standard User Equipment") and U.S. patent Ser. No. 10/559,081 (Omer et al., Feb. 11, 2020, "Method and System for Automated Visual Analysis of a Dipstick Using Standard User Equipment") disclose a method for analyzing a dipstick using a smartphone. U.S. patent application 20190008694 (Piotrowski et al., Jan. 10, 2019, "Systems and Methods for Wound Healing") discloses systems and methods to promote wound healing, including a wound dressing having a wound-facing surface and a second surface.

U.S. patent application 20190028634 (Koehler et al., Jan. 24, 2019, "Mobile System and Method") discloses a mobile system with a camera, wherein the circuitry captures a plurality of images of a user's eye with the camera. U.S. patent application 20190028674 (Smits et al., Jan. 24, 2019, "Holographic Video Capture and Telepresence System") discloses a system for recording, transmitting, and displaying a three-dimensional image of a face of a user in a video stream. U.S. patent application 20190038135 (Lee et al., Feb. 7, 2019, "Electronic Device, Mobile Terminal and Control Method Thereof") discloses a mounting portion to which one of a plurality of optical heads is selectively mountable.

U.S. patent application 20190083025 (Aung et al., Mar. 21, 2019, "Devices, Systems, and Methods for Monitoring Wounds") discloses a wound-monitoring device with an imaging component and a light emitter that emits light at a calibrated wavelength. U.S. patent application 20190244566 (Kim et al., Aug. 8, 2019, "Electronic Device and Method for Compensating Image Quality of Display Based on First Information and Second Information") discloses a method for compensating for distortion on a display of an electronic device.

U.S. patent application 20190290187 (Adiri et al., Sep. 26, 2019, "Measuring and Monitoring Skin Feature Colors, Form and Size") and U.S. patent Ser. No. 10/362,984 (Adiri et al., Jul. 30, 2019, "Measuring and Monitoring Skin Feature Colors, Form and Size") and U.S. Pat. No. 11,026,624 (Adiri et al., Jun. 8, 2021, "Measuring and Monitoring Skin Feature Colors, Form and Size") disclose kits, diagnostic systems and methods which measure the distribution of colors of skin features by comparison to calibrated colors which are co-imaged with the skin feature. U.S. patent application 20200126227 (Adiri et al., Apr. 23, 2020, "Systems and Methods for Urinalysis Using a Personal Communications Device") discloses systems and methods for testing visible chemical reactions of a reagent. U.S. patent application 20200211193 (Adiri et al., Jul. 2, 2020, "Tracking Wound Healing Progress Using Remote Image Analysis") discloses systems and methods for tracking healing progress of multiple adjacent wounds using a colorized surface with colored reference elements.

U.S. patent application 20200211228 (Adiri et al., Jul. 2, 2020, "Uniquely Coded Color Boards for Analyzing Images") discloses systems and methods for a color board for use in reagent strip testing. U.S. patent Ser. No. 10/991,096 (Adiri et al., Apr. 27, 2021, "Utilizing Personal Communications Devices for Medical Testing") discloses systems and methods for analyzing visible chemical reactions. U.S. patent application 20210142888 (Adiri et al., May 13, 2021, "Image Processing Systems and Methods for Caring for Skin Features") discloses systems and methods for image processing of a skin feature which may include receiving first and second images from at least one image sensor associated with a mobile communications device.

U.S. patent application 20190251710 (Park et al., Aug. 15, 2019, "Method and Electronic Device for Converting Color of Image") discloses methods and apparatuses for displaying a representative color of an image. U.S. patent application 20190307337 (Little et al., Oct. 10, 2019, "Methods and Apparatus for Self-Calibrating Non-Invasive Cuffless Blood Pressure Measurements") discloses a non-invasive method of measuring blood pressure. U.S. patent applications 20190307400 (Zhao et al., Oct. 10, 2019, "Systems for Personal Portable Wireless Vital Signs Scanner"), 20190350535 (Zhao et al., Nov. 21, 2019, "Systems, Methods, and Apparatus for Personal and Group Vital Signs Curves"), and 20200196962 (Zhao et al., Jun. 25, 2020, "Systems, Methods, and Apparatus for Personal and Group Vital Signs Curves") disclose methods, systems, and apparatus for periodically and simultaneously scanning for a plurality of vital signs of a user.

U.S. patent application 20190320969 (Levi et al., Oct. 24, 2019, "Bedside or Intra Operative Assessment of Tissue Damage Depth and Readiness for Reconstruction") discloses a short wave infrared (SWIR) imaging system. U.S. patent application 20190343396 (Khosravi et al., Nov. 14, 2019, "Apparatus for Imaging Skin") discloses an apparatus with lights and lenses which is attached to a mobile device in order to image skin. U.S. patent application 20190391236 (Downing et al., Dec. 26, 2019, "Photonics Device") discloses a method of generating separate and discrete wavelengths and light intensity profiles based on an interaction between the separate and discrete wavelengths and a multi-wavelength diffractive optic element.

U.S. patent application 20190391729 (Josephson et al., Dec. 26, 2019, "Apparatuses, Systems, and/or Interfaces for Embedding Selfies into or onto Images Captured by Mobile or Wearable Devices and Method for Implementing Same") discloses a mobile device with a camera system which captures an image and embeds the image into a background image. U.S. patent application 20200041761 (Seo et al., Feb. 6, 2020, "Optical Lens Assembly and Electronic Device Comprising Same") discloses an optical lens assembly and electronic apparatus. U.S. patent application 20200059596 (Yoo et al., Feb. 20, 2020, "Electronic Device and Control Method Thereof") discloses a graphic user interface (GUI) for adjusting the image capture position of a camera. U.S. patent application 20200085164 (Tamir et al., Mar. 19, 2020, "Apparatus with Imaging Functionality") discloses a camera on a pincer apparatus.

U.S. patent application 20200126283 (Van Vuuren et al., Apr. 23, 2020, "Method and System for Implementing Three-Dimensional Facial Modeling and Visual Speech Synthesis") disclose tools and techniques for three-dimensional facial modeling and visual speech synthesis. U.S. patent application 20200170564 (Jiang et al., Jun. 4, 2020, "Automatic Image-Based Skin Diagnostics Using Deep Learning") discloses a deep-learning-based system and method for skin diagnostics. U.S. patent application 20200185073 (De Brouwer et al., Jun. 11, 2020, "System and Method for Providing Personalized Health Data") discloses a method for providing personalized blood tests.

U.S. patent application 20200186782 (Bigioi et al., Jun. 11, 2020, "Depth Sensing Camera System") discloses a depth-sensing camera system with a fisheye lens and a (near) infrared sensor. U.S. patent applications 20200193580 (Mccall et al., Jun. 18, 2020, "System and Method for High Precision Multi-Aperture Spectral Imaging") and 20210082094 (Mccall et al., Mar. 18, 2021, "System and Method for High Precision Multi-Aperture Spectral Imaging") disclose systems and techniques for spectral imaging using a multi-aperture system with curved multi-bandpass filters positioned over each aperture.

U.S. patent applications 20200193597 (Fan et al., Jun. 18, 2020, "Machine Learning Systems and Methods for Assessment, Healing Prediction, and Treatment of Wounds") and 20210201479 (Fan et al., Jul. 1, 2021, "Machine Learning Systems and Methods for Assessment, Healing Prediction, and Treatment of Wounds") disclose machine learning systems and methods for prediction of wound healing. U.S. patent application 20200241290 (Breese et al., Jul. 30, 2020, "Light Deflection Prism for Mounting to a Surface of a Device, Device, and Method for Altering a Field of View of a Camera") discloses a prism for altering a field of view of a camera.

U.S. patent application 20200279659 (De Brouwer et al., Sep. 3, 2020, "System and Method for Remote Medical Information Exchange") discloses a method and system for remote medical information exchanging. U.S. patent application 20200293887 (De Brouwer et al., Sep. 17, 2020, "System and Method With Federated Learning Model for Medical Research Applications") discloses a method and system with a federated learning model for health care applications. U.S. patent application 20200342987 (De Brouwer et al., Oct. 29, 2020, "System and Method for Information Exchange With a Mirror") discloses a method and system for remote medical information exchange.

U.S. patent application 20200280661 (Barnes et al., Sep. 3, 2020, "Systems and Methods for Spectral Imaging With Compensation Functions") discloses systems and methods for imaging with compensation functions. U.S. patent application 20200310083 (Kim et al., Oct. 1, 2020, "Optical Lens Assembly and Electronic Device Comprising Same") discloses an optical lens assembly and electronic device. U.S. patent application 20200330028 (Nejati et al., Oct. 22, 2020, "System and Method for Facilitating Analysis of a Wound in a Target Subject") discloses a system and method for facilitating analysis of a wound using a neural network. U.S. patent application 20200348493 (Seo et al., Nov. 5, 2020, "Optical Lens System and Electronic Device Including the Same") discloses an electronic device with a window member, a display panel stacked on a rear surface of the window member, a lens assembly, an iris, and an image sensor.

U.S. patent application 20200352515 (Godavarty et al., Nov. 12, 2020, "Cellphone Based Tissue Oxygenation Measuring Device") discloses a cellphone-based oxygenation measurement tool. U.S. patent applications 20200352686 (Yancey et al., Nov. 12, 2020, "Scanning Device") and 20210077233 (Yancey et al., Mar. 18, 2021, "Scanning Device") disclose a scanning device to scan teeth of a user and acquire images of the teeth. U.S. patent application 20200364862 (Dacosta et al., Nov. 19, 2020, "Wound Imaging and Analysis") discloses an imaging device using characteristics of wound fluoresce with a unique spectral signature. U.S. patent application 20200374437 (Kang et al., Nov. 26, 2020, "Electronic Device Having Camera Module Capable of Switching Line of Sight and Method for Recording Video") discloses a camera module capable of changing a sightline and a method of recording video.

U.S. patent application 20200381127 (Silverman et al., Dec. 3, 2020, "Method and System for Assessing, Quantifying, Coding & Communicating Patient's Health and Perioperative Risk") discloses a multi-dimensional system for assessing, coding, quantifying, displaying, integrating and communicating information relating to patient health and perioperative risk. U.S. patent application 20200401830 (Zhu et al., Dec. 24, 2020, "Method, Apparatus and Storage Medium for Controlling Image Acquisition Component") discloses a terminal with a movable image acquisition component. U.S. patent application 20200404164 (Wu et al., Dec. 24, 2020, "Method and Apparatus for Controlling Camera, Device and Storage Medium") discloses a method of controlling a camera applicable to a terminal device with a Dynamic Vision Sensor (DVS) collecting circuit.

U.S. patent application 20210004995 (Burg et al., Jan. 7, 2021, "Methods and Apparatus for Enhancing Color Vision and Quantifying Color Interpretation") and U.S. patent Ser. No. 11/030,778 (Burg et al., Jun. 8, 2021, "Methods and Apparatus for Enhancing Color Vision and Quantifying Color Interpretation") disclose a method including selecting a first color sample within a target area in a first image of a first object displayed by a display device; selecting a second color sample within a target area in a second image of a second object displayed in the display device; and comparing the first color sample against the second color sample.

U.S. patent application 20210007606 (Su et al., Jan. 14, 2021, "Method of and Imaging System for Clinical Sign Detection") discloses a method of and an imaging system for clinical sign detection. U.S. patent application 20210012130 (Park et al., Jan. 14, 2021, "Method and Device for Measuring Biometric Information in Electronic Device") discloses a method and a device for measuring a user's biometric information in an electronic device and providing information related to the biometric information. U.S. patent application 20210029300 (Lee et al., Jan. 28, 2021, "Electronic Device and Method for Providing Content Associated with Camera Function From Electronic Device") discloses an electronic device with a display, a camera, a communication module, and a processor.

U.S. patent application 20210084216 (Choi et al., Mar. 18, 2021, "Method of Controlling Camera Device and Electronic Device Thereof") discloses an electronic device and a method for controlling a camera device in the electronic device based on information input through an adjacent area of the partial area of the display. U.S. patent application 20210124424 (Sandhan et al., Apr. 29, 2021, "Method for Controlling Camera and Electronic Device Therefor") discloses a method for controlling a camera of an electronic device by generating a plurality of beams using an antenna array.

U.S. patent application 20210127989 (Atamanuk et al., May 6, 2021, "Method of Estimation of the Hemodynamic Status and Capacity of Effort from Patients with Cardiovascular and Pulmonar Diseases") discloses a method to the effort capacity of a human individual as an expression of distance walked by the individual. U.S. patent application 20210128021 (Emalfarb et al., May 6, 2021, "Systems and Methods for Verified Biomeasurements") discloses a method for generating, via a camera, image data that is reproducible as an image of at least a portion of a subject.

U.S. patent application 20210132795 (Kurbanova et al., May 6, 2021, "Smart Minor and Table Top Devices with Sensor Fusion of Camera Vision, Acoustic, and Multi-Point Capacitive Touch Control") discloses a smart mirror. U.S. patent application 20210136263 (Pitman, May 6, 2021, "Mobile Terminal") discloses a mobile terminal with a camera and at least one distal lens disposed remotely from the camera. U.S. patent application 20210145359 (Hunt et al., May 20, 2021, "Wound Analysis Device and Method") discloses a monitoring and therapy system which collects video images of a tissue site, amplifies said video images via Eulerian Video Magnification, and determines a treatment parameter.

U.S. patent applications 20210161621 (Salah et al., Jun. 3, 2021, "Method for Analysing a Dental Situation") and 20210186658 (Salah et al., Jun. 24, 2021, "Method for Analysing a Dental Situation") disclose a method for analyzing a patient's dental situation. U.S. patent application 20210217797 (Hashiguchi et al., Jul. 15, 2021, "Solid-State Imaging Device and Electronic Apparatus") discloses an imaging device with a first substrate having a pixel unit. U.S. patent application 20210218923 (Yoda et al., Jul. 15, 2021, "Solid-State Imaging Device and Electronic Device") discloses an imaging device including an array unit in which a plurality of pixels each have a photoelectric conversion unit. U.S. patent application 20210225032 (Hain et al., Jul. 22, 2021, "Multiple Camera Calibration") discloses a method for generating pose transformation data between first and second rigidly mounted digital cameras having non-coincident fields of view.

U.S. patent application 20210225509 (Wang et al., Jul. 22, 2021, "Method, Apparatus and System for Guiding Diagnosis-And-Treatment, and Computer Readable Storage Medium") discloses a method, apparatus and system for guiding diagnosis-and-treatment, and a computer readable storage medium. U.S. patent application 20210225516 (Liu et al., Jul. 22, 2021, "Method and Device for Processing Physiological Data, and Storage Medium") discloses a method for processing physiological data, a device for processing physiological data, and a non-volatile storage medium. U.S. patent application 20210226906 (Ryu et al., Jul. 22, 2021, "Electronic Device and Method for Image Control Thereof") discloses a device with a display, a communication interface, and a processor comprising processing circuitry.

U.S. patent application 20210227019 (Soon-Shiong et al., Jul. 22, 2021, "Camera-to-Camera Interactions, Systems and Methods") discloses methods of delegating media capturing functionality from one device to another. U.S. patent application 20210227413 (Yang et al., Jul. 22, 2021, "Method and Communication Device for Performing Measurement") discloses a method for performing measurement using a configured measurement gap (MG) from a serving cell.

The following section reviews relevant art from sources other than patents and patent applications.

Ashique, 2015, "Clinical Photography in Dermatology Using Smartphones: An Overview," Indian Dermatology Online Journal, 2015, 6, 3, 158, provides an overview of smartphone photography in clinical dermatology. Burns, 2015, "Digital Photography and the Medical Selfie," Journal of Participatory Medicine, Feb. 11, 2015, 7, e3, discusses how capturing and controlling health data can promote a patient from being a passive recipient to an active co-creator of modern health care. Burns, 2019, "Creating Consumer-Generated Health Data: Interviews and a Pilot Trial Exploring How and Why Patients Engage," Journal of Medical Internet Research, 2019, 21(6), e12367, discusses how consumer-generated health data (CGHD) is being used by consumers and how it influences their engagement via a validated framework. Coleman, 2019, "Cell Phone Based Colorimetric Analysis for Point-of-Care Settings," The Analyst, Jan. 28, 2019, 144(6), 1935-1947, discusses a cell phone imaging algorithm that enables analysis of assays that would typically be evaluated via spectroscopy.

Diethei, 2018, "Using Smartphones to Take Eye Images for Disease Diagnosis in Developing Countries," Proceedings of the Second African Conference for Human Computer Interaction: Thriving Communities (Windhoek, Namibia) (AfriCHI '18). ACM, New York, N.Y., Article 34, discusses EyeGuide, a mobile application that helps people to take eye images. Diethei, 2020, "Medical Selfies: Emotional Impacts and Practical Challenges," MobileHCI '20: 22nd International Conference on Human-Computer Interaction with Mobile Devices and Services, Oct. 5, 2020, 8, 1-2, discusses how medical images taken with mobile phones by patients can allow screening, monitoring, and diagnosis of skin lesions. Farr, 2020, "Healthy.io, Maker of a Medical Selfie, Is Part of the New Generation of Israeli Health-Tech Companies," CNBC, Jun. 22, 2020, discusses innovations by Healthy.io including an FDA-approved stick which is dipped into urine and calibration stickers which allow clinicians to accurately measure wounds.

Florida Atlantic University, 2019, "Selfies to Self-Diagnosis: Algorithm Amps Up Smartphones to Diagnose Disease," Science Daily, Fe. 12, 2019, discusses image capture using three smartphones: the Android Moto G; the iPhone 6; and the Samsung Galaxy Edge. Granot, 2008, "A New Concept for Medical Imaging Centered on Cellular Phone Technology," PloS one, 3, e2075, discusses the use of cell phones to transmit remote medical imaging data. Healthy.io, 2020, "Digitizing Wound Management: A Standardized, Evidence-Based Approach to Healing," Healthy.io, White Paper, 2020, discusses Healthy.io's wound management technology which enables clinicians to take automatic measurements using a smartphone. Lee, 2018, "Recent Trends in Teledermatology and Teledermoscopy," Dermatology Practical & Conceptual, 2018, 8, 3, 214, discusses recent trends in teledermatology via both asynchronous store-and-forward modes and a real-time video conferencing modes.

Mai, 2020, "The Effect of Perioral Scan and Artificial Skin Markers on the Accuracy of Virtual Dentofacial Integration: Stereophotogrammetry Versus Smartphone Three-Dimensional Face-Scanning," International Journal of Environmental Research and Public Health, 2020, 18(1), 229, discusses a study of the effects of different matching methods on the accuracy of dentofacial integration in stereophotogrammetry and smartphone face-scanning systems. Otero, 2019, "Comparison of Different Smartphone Cameras to Evaluate Conjunctival Hyperaemia in Normal Subjects," Scientific Reports, 2019, 9, 1339, compares the objective and subjective quantification of conjunctival redness in images obtained with calibrated and non-calibrated cameras, in different lighting conditions and optical magnifications. Peng, 2017, "Constructing a 3D Multiple Mobile Medical Imaging System through Service Science, Management, Engineering and Design," Systems, 2017, 5(1), 5, discusses a 3D multiple mobile medical imaging system (3D MMMIS) for doctor's diagnosis and treatment.

Pires, 2015, "Wound Area Assessment Using Mobile Application," Biodevices, 2015, discusses the use of mobile devices to identify wound contours and areas in captured images. Pivo, 2019, "Pivo Pod Get Insanely Creative Gifs, Photos, Videos," Indiegogo, campaign closed Jan. 19, 2019, provides an overview of the "Pivo" pod, a phone-holding device with a stationary base and pivoting upper portion, which pivots a phone to track a moving (e.g. dancing) person in order to create videos (e.g. for sharing on social media). Senthilkumaran, 2021, "Simple Technique for Medical Photography in the Emergency Department During the COVID Pandemic: Say Cheese," Journal of Emergency Medicine, Letter to the Editor, 5/1/2021, 60(5), e135, discusses mounting a smartphone on a selfie stick for use in an emergency room.

Wicklund, 2019, "mHealth Researchers Look to Make the Selfie a Health Resource," mHealth Intelligence, Aug. 9, 2019, discusses the use of medical selfies to evaluation blood pressure, atrial fibrillation, and other medical conditions. Wong, 2018, "Real-World Use of Telemedicine: A Picture Is Worth a Thousand Words," PMFA Journal, 5(2), December/January, 2018, discusses information technology issues related to the use of mobile phone images within the NHS system. Zhou, 2012, "A Survey of Optical Imaging Techniques for Assessing Wound Healing," International Journal of Intelligent Control and Systems, September, 2012 17(3), 79-85, discusses how optical imaging can be used to overcome both the lack of objectivity and noninvasiveness in the identification, evaluation, and assessment of cutaneous wounds and cutaneous wound healing.

SUMMARY OF THE INVENTION

This invention is a portable phone-moving device to guide medical imaging using a mobile phone or other camera-enabled mobile device. This phone-moving device includes an attachment mechanism which holds a camera-enabled mobile phone or other camera-enabled mobile device onto the phone-moving device. The device automatically moves the mobile phone or other mobile device over a selected portion of a person's body to guide the capturing of phone images of that portion from different angles and/or distances for medical imaging purposes. In an example, the phone-moving device can have one or more electromagnetic motors which move it.

In an example, images of a portion of the person's body from different angles and/or distances can be combined to create a digital three-dimensional image of the portion of the person's body which is navigated and viewed by a non-local healthcare provider at a later time. Alternatively, movement of a phone by the phone-moving device can be remotely-controlled by a non-local healthcare provider in real time.

This phone-moving device can improve the usefulness of camera-enabled mobile phones (and other camera-enabled mobile devices such as tablets and smart watches) for remote medical image purposes, addressing limitations of the relevant art which have been discussed previously. Such improvement in remote medical imaging can advance telemedicine and provide access to specialized care for many people in less-populated areas.

BRIEF INTRODUCTION TO THE FIGURES

DETAILED DESCRIPTION OF THE FIGURES

Figure 1:
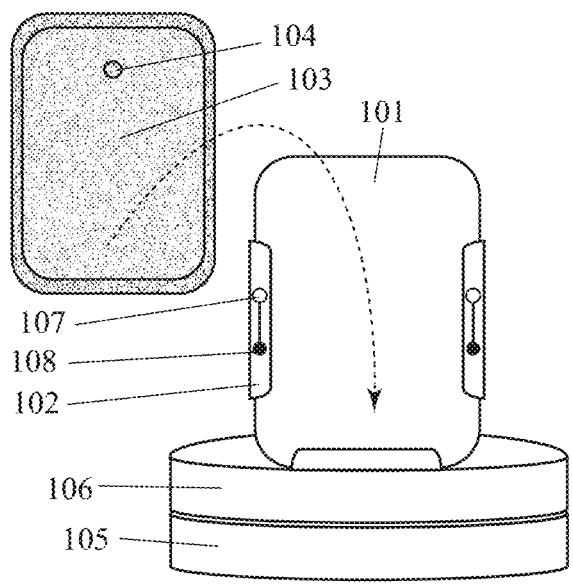
FIGS. 1 through 4 show a phone-moving device with lights which rotates an attached mobile phone for medical imaging.

Before discussing the specific embodiments of the invention which are shown in FIGS. 1 through 50, it is useful to provide an introduction to the general design and components of the invention, as well as some example variations which can apply (where relevant) to the embodiments shown in FIGS. 1 through 50. That is the purpose of this section which is provided before discussion of individual figures.

In an example, a portable phone-moving device to guide medical imaging can comprise: a portable phone-moving device; wherein the phone-moving device further comprises an attachment mechanism which holds a camera-enabled mobile phone or other camera-enabled mobile device onto the phone-moving device; and wherein the phone-moving device moves the mobile phone or other mobile device over a selected portion of a person's body to guide the capturing of phone images of that portion from different angles and/or distances for medical imaging purposes.

In an example, the portable phone-moving device can further comprise one or more electromagnetic motors which move the device. In an example, images of the portion of the person's body from different angles and/or distances can be combined to create a digital three-dimensional image of the portion of the person's body which is navigated and viewed by a non-local healthcare provider at a later time. Alternatively, movement of the phone by the device can be remotely-controlled by a non-local healthcare provider in real time. In an example, the attachment mechanism can be selected from the group consisting of one or more clips, clasps, clamps, hooks, straps, bands, recesses, pockets, magnets, and hook-and-eye materials. In an example, the portable phone-moving device can further comprise a phone-supporting surface to which the phone or other mobile device is attached.

In an example, the portable phone-moving device can further comprise a rotating, pivoting, and/or tilting horizontal arm which rotates, pivots, and/or tilts the phone. In an example, the portable phone-moving device can further comprise a rotating, pivoting, and/or tilting vertical arm which rotates, pivots, and/or tilts the phone. In an example, the portable phone-moving device can further comprise an arcuate track along which the phone is moved over the portion of the person's body. In an example, the portable phone-moving device can further comprise a semicircular track along which the phone is moved over the portion of the person's body. In an example, the portable phone-moving device can further comprise an extension mechanism which moves the phone closer to, or father from, the device.

In an example, the portable phone-moving device can further comprise a cantilevered arm which holds the phone out over the portion of the person's body. In an example, the portable phone-moving device can further comprise an arm which holds the phone out over the portion of the person's body, wherein there is a counterweight on the portion of the arm opposite the portion of the arm which holds the phone. In an example, the portable phone-moving device can further comprise one or more motorized telescoping members which change the height of the device. In an example, the portable phone-moving device can further comprise one or more motorized telescoping members which change the width of the device.

In an example, the portable phone-moving device can further comprise motorized wheels which move the device. In an example, the portable phone-moving device can further comprise motorized caterpillar treads which move the device. In an example, the portable phone-moving device can further comprise a motorized articulated robotic arm with at least three articulated segments, wherein the phone is attached to the robotic arm. In an example, the portable phone-moving device can further comprise a motorized gooseneck robotic arm, wherein the phone is attached to the robotic arm. In an example, the portable phone-moving device can further comprise one or more light emitters.

In an example, a portable phone-moving device which guides phone imaging of a portion of a person's body for medical evaluation purposes can comprise: a portable phone-moving device; wherein the phone-moving device further comprises an attachment mechanism which holds a conventional camera-enabled mobile phone (or other camera-enabled mobile device such as a tablet or smart watch) onto the phone-moving device; wherein the phone-moving device automatically moves the phone over and/or around a selected portion of a person's body to guide the capturing of phone images of the portion of the person's body from different angles and/or distances, and wherein phone images of the portion of the person's body from different angles and/or distances are used for medical evaluation purposes. In an example, captured images can be moving images (e.g. video). In an example, captured images can be a plurality of still-frame images.

In an example, a portable phone-moving device which guides phone imaging of a portion of a person's body for medical evaluation purposes can comprise: a portable phone-moving device; wherein the phone-moving device further comprises an attachment mechanism which holds a conventional camera-enabled mobile phone (or other camera-enabled mobile device such as a tablet or smart watch) onto the phone-moving device; wherein the phone-moving device further comprises an electromagnetic motor which moves the phone over and/or around a selected portion of a person's body to guide the capturing of phone images of that portion of the person's body from different angles and/or distances for medical evaluation purposes, and wherein the motor moves the centroid of the phone along a path which is at least three inches long.

In an example, a portable phone-moving device which guides phone imaging of a portion of a person's body for medical evaluation purposes can comprise: a portable phone-moving device; wherein the phone-moving device further comprises an attachment mechanism which holds a conventional camera-enabled mobile phone (or other camera-enabled mobile device such as a tablet or smart watch) onto the phone-moving device; wherein the phone-moving device further comprises an electromagnetic motor which a non-local healthcare provider and/or medical AI controls to move the phone over and/or around a selected portion of a person's body to guide the capturing of phone images of the portion of the person's body from different angles and/or distances, wherein phone images of the portion of the person's body from different angles and/or distances are used for medical evaluation purposes, and wherein the motor moves the centroid of the phone along a path which is at least three inches long.

In an example, a portable phone-moving device which guides phone imaging of a portion of a person's body for medical evaluation purposes can comprise: a portable phone-moving device; wherein the phone-moving device further comprises an attachment mechanism which holds a conventional camera-enabled mobile phone (or other camera-enabled mobile device such as a tablet or smart watch) onto the device; wherein the phone-moving device further comprises an electromagnetic motor; and wherein the motor moves the phone over and/or around a selected portion of a person's body to guide the capturing of phone images of the portion of the person's body from different angles and/or distances, wherein phone images of the portion of the person's body from different angles and/or distances are combined to create a three-dimensional digital model of the portion for medical evaluation purposes, and wherein the motor moves the centroid of the phone along a path which is between three inches and three feet long.

In an example, a portable phone-moving device can be used in combination with a conventional camera-equipped mobile phone. The camera on the conventional mobile phone can be moved to different locations and/or orientations relative to a portion of a person's body in order to create a digital three-dimensional model and/or digital 3D model of a selected portion of the person's body. In an example, a healthcare provider can access and navigate the three-dimensional model, at a later time, for medical evaluation purposes, selecting their desired viewing angle and distance using the pre-constructed 3D model. Alternatively, a healthcare provider can remotely-control motion of the phone-moving device, moving the phone to view a selected portion of a person's body from selected angles and distances in real time.

In an example, a health plan or provider can ship such a phone-moving device to a person's home. In an example, a health plan or provider can give such a device to a patient during a visit for the patient to take and use at home. In an example, a person can set up the device at their home for remote medical imaging purposes. In an example, a phone-moving device can enable a person to take a better medical selfies by enabling better control of image angle, distance, focus, lighting, and/or color calibration. In an example, a person can set up such a device by attaching a conventional camera-equipped mobile phone to the device and connecting the device to the internet so that a non-local healthcare provider can remotely control (e.g. move) the camera by moving the device. Alternatively, such a device can be used at a remote medical facility, enabling a non-local healthcare specialist to view and evaluate a portion of a person's body. In an example, a phone-moving device can serve as the connectivity component of a remote medical imaging system, wherein a conventional mobile phone serves as the imaging component.

In an example, a phone-moving device includes an attachment mechanism by which a conventional phone is attached to the phone-moving device. In an example, this attachment mechanism is designed so that it does not obscure the phone's distal-facing camera. In an example, an attachment mechanism can latch, clamp, or otherwise hold, a phone against a flat surface on a phone-moving device. In an example, an attachment mechanism can be a rectangular recess, opening, pocket or track into which a camera-equipped mobile phone is inserted. In an example, a phone-moving device can have an electronic connection (e.g. plug) between the phone and the device. In an example, a phone-moving device can have a mechanical connection (e.g. button presser) between the phone and the device. In an example, a phone-moving device can have a wireless communication connection between the phone and the device.

In an example, an attachment mechanism by which a phone is attached to a phone-moving device can be selected from the group consisting of: clip, clasp, clamp, prong, plug, snap, hook, band, strap, hook-and-eye material. In an example, an attachment mechanism can be one or more clips, clasps, or clamps which attach a mobile phone to the device. In an example, an attachment mechanism can be one or more hooks or prongs which attach a mobile phone to the device. In an example, an attachment mechanism can be one or more straps, bands, or ties which attach a mobile phone to the device. In an example, an attachment mechanism can be hook-and-eye material (e.g. Velcro™) which attaches a mobile phone to the device. In an example, an attachment mechanism can be one or more magnets which attach a mobile phone to the device. In an example, an attachment mechanism can be a pocket, recess, track, or other opening into which a mobile phone is inserted. In an example, a phone can be slid into an opening on a device.

In an example, an attachment mechanism can comprise at least one clip. In an example, an attachment mechanism can comprise at least one clasp. In an example, an attachment mechanism can comprise at least one clamp. In an example, an attachment mechanism can comprise at least one prong. In an example, an attachment mechanism can comprise at least one plug. In an example, an attachment mechanism can comprise at least one snap. In an example, an attachment mechanism can comprise at least one hook. In an example, an attachment mechanism can comprise at least one band. In an example, an attachment mechanism can comprise at least one strap. In an example, an attachment mechanism can comprise hook-and-eye material. In an example, an attachment mechanism can comprise at least one pocket. In an example, an attachment mechanism can comprise at least one recess. In an example, an attachment mechanism can comprise at least one track.

In an example, a phone-supporting portion of a phone-moving device can be moved (e.g. rotated, revolved, pivoted, rolled, slid, swung, oscillated, extended, and/or driven) by a motor on the device, thereby changing the focal angle, direction, and/or distance of a camera on an attached conventional mobile phone (or other camera-equipped mobile device). In an example, a phone-moving device can have an electromagnetic motor which moves (e.g. rotates, revolves, pivots, rolls, slides, swings, oscillates, extends, and/or drives) a camera-equipped phone which is attached to the device, thereby changing the focal angle, direction, and/or distance of the phone's camera.

In an example, a phone-moving device can have one or more electromagnetic motors which selectively move (e.g. rotate, pivot, roll, slide, swing, oscillate, extend, and/or drive) a camera-equipped phone which is attached to the device, thereby keeping the focal direction of the camera always pointed toward a selected area on a person's body as the phone is moved across and/or around the person's body. In an example, a device can change the angle by which a phone images a portion of a person's body in proportion to a change in the distance by which the phone is moved across and/or around the portion of the person's body. In an example, a device can change the angle by which a phone images an area of a person's body in proportion to the change in the distance by which the phone is moved across and/or around the area, so that the area is imaged from the same distance, but different angles.

In an example, a phone-moving device can be remotely controlled and moved (e.g. rotated, pivoted, rolled, slid, swung, oscillated, and/or driven) by a non-local healthcare provider, thereby changing the focal direction of a camera on a mobile phone which is attached to the device. In an example, this remote control can be via a phone-based application. In an example, this remote control can be via the internet. In an example, a phone-moving device can be automatically moved (e.g. rotated, pivoted, rolled, slid, swung, oscillated, and/or driven) by software (e.g. an application) on an attached phone, thereby changing the focal direction of a camera on the phone.

In an example, a phone-moving device can be automatically moved (e.g. rotated, pivoted, rolled, slid, swung, oscillated, and/or driven) by software (e.g. by medical AI), thereby changing the focal direction of a camera on a mobile phone which is attached to the device. In an example, a phone-moving device can be automatically moved (e.g. rotated, pivoted, rolled, slid, swung, oscillated, and/or driven) by software (e.g. by medical AI), thereby changing the focal direction of a camera on a mobile phone which is attached to the device in order to create a 3D model of a selected portion of a person's body.

In an example, a phone-moving device can have an electromagnetic motor which rotates and/or pivots an attached mobile phone around the phone's horizontal and/or lateral axis. In an example, a motor can oscillate (e.g. repeatedly rotate and/or revolve, clockwise and then counter-clockwise) a phone over and/or around a selected portion of a person's body. In an example, a motor can pivot an attached mobile phone up and down, as well as rotate the phone clockwise and counter-clockwise. In an example, a motor can rotate, revolve, and/or pivot a phone between 20 and 180 degrees. In an example, a motor can rotate, revolve, and/or pivot a phone in one or more complete 360-degree circles.

In an example, a phone-moving device can move a mobile phone over and/or around a portion of a person's body at a distance between one inch and three feet from a selected portion of a person's body. In an example, a phone-moving device can rotate and/or pivot a phone so that the focal vector of the phone's camera remains directed toward a selected area of a person's body as the phone moves along a path in space. In an example, a phone-moving device can rotate, pivot, or tilt a phone as the phone is moved in an arcuate path over and/or around an area of a person's body so that the focal direction of the phone camera remains pointed toward the area. In an example, a phone-moving device can rotate, pivot, or tilt a phone as the phone is moved over and/or around an area of a person's body so that the front surface of the phone remains substantially tangential to a radial vector extending outward from the area.

In an example, a phone-moving device can rotate a phone to capture images of a portion of a person's body from different angles and/or orientations. In an example, a phone-moving device can rotate and/or pivot a phone around the phone's central axis. In an example, a phone-moving device can rotate and/or pivot a phone around the phone's central latitudinal axis. In an example, a phone-moving device can rotate and/or pivot a phone around the phone's central longitudinal axis. In an example, a phone-moving device can rotate and/or pivot a phone back and forth around the phone's centroid. In an example, a phone-moving device can rotate and/or pivot a phone in alternating clockwise and counter-clockwise directions, around a central longitudinal axis of the phone during a scan of a portion of person's body. In an example, a phone-moving device can rotate and/or pivot a phone in alternating clockwise and counter-clockwise directions while a portion of a person's body is being scanned.

In an example, a phone-moving device can move an attached phone is a pre-programmed series of directions in order to capture images which are combined to create a three-dimensional scan (e.g. three-dimensional digital model) of a portion of a person's body. In an example, these moves can include moving the phone back and forth, across and/or around, an area of the person's body. These movements change the viewing angle and distance from the phone to the area of person's body so that images of the area are captured from multiple angles and distances. Images from multiple angles and distances are combined to create a three-dimensional digital image of the portion of the person's body for diagnostic evaluation by a healthcare provider. In an example, a healthcare provider can navigate this digital three-dimensional at a later time, zooming in or out and panning from side to side as part of their medical evaluation of the body area.

In an example, a phone-moving device can rotate, pivot, and/or tilt an attached mobile phone to keep the phone's camera pointed toward a selected area of a person's body while the phone is moved over and/or around that area. In an example, a phone-moving device can tilt a phone to capture images of a portion of a person's body from different angles. In an example, a phone-moving device can oscillate a phone back and forth around a central longitudinal axis of the phone. In an example, a phone-moving device can oscillate a phone back and forth the phone around a central latitudinal axis of the phone. In an example, a phone-moving device can oscillate a phone back and forth the phone around a central axis of the phone.

In an example, the angle of a mobile phone relative to an arm or track near a person's body can be adjusted. In an example, the angle of a mobile phone relative to an arm or track near a person's body can be adjusted by expansion or contraction of a telescoping mechanism. In an example, the angle of a mobile phone relative to an arm or track near a person's body can be adjusted by rotation of a threaded mechanism. In an example, the angle of a mobile phone relative to an arm or track near a person's body can be adjusted by an electromagnetic motor. In an example, the angle of a mobile phone relative to a person's body can be adjusted. In an example, the angle of a mobile phone relative to a person's body can be adjusted by expansion or contraction of a telescoping mechanism. In an example, the angle of a mobile phone relative to a person's body can be adjusted by rotation of a threaded mechanism. In an example, the angle of a mobile phone relative to a person's body can be adjusted by an electromagnetic motor.

In an example, the angle of a mobile phone relative to an arm or track above a person's body can be remotely adjusted by a healthcare provider by expansion or contraction of a telescoping mechanism. In an example, the angle of a mobile phone relative to an arm or track above a person's body can be remotely adjusted by a healthcare provider by rotation of a threaded mechanism. In an example, the angle of a mobile phone relative to an arm or track above a person's body can be remotely adjusted by a healthcare provider by an electromagnetic motor. In an example, the angle of a mobile phone relative to a person's body can be remotely adjusted by a healthcare provider by expansion or contraction of a telescoping mechanism. In an example, the angle of a mobile phone relative to a person's body can be remotely adjusted by a healthcare provider by rotation of a threaded mechanism. In an example, the angle of a mobile phone relative to a person's body can be remotely adjusted by a healthcare provider by an electromagnetic motor.

In an example, a phone-moving device can automatically change the angle and/or distance from a mobile phone to a portion of the person's body which is being scanned (imaged). In an example, a phone-moving device can rotate and/or pivot a mobile phone (or other camera-equipped mobile device) around its longitudinal axis to maintain focus toward the same area of a person's body as the phone is moved. In an example, a phone-moving device can rotate and/or pivot a mobile phone (or other camera-equipped mobile device) around its longitudinal axis to maintain focus toward the same area of a person's body as the phone is moved horizontally and/or vertically. In an example, a phone-moving device can rotate and/or pivot a mobile phone (or other camera-equipped mobile device) around its longitudinal axis to maintain focus toward the same area of a person's body as the device is propelled by motorized wheels and/or treads.

In an example, a phone-moving device can move (e.g. rotate, pivot, and/or oscillate) a phone back and forth (e.g. clockwise and counter-clockwise) around a central axis of the phone in order to take pictures of a stationary portion of a person's body from different angles. In an example, a phone-moving device can move a phone along an arcuate (e.g. concave) path over and/or around a portion of a person's body, wherein the portion is located at the focal center of the arcuate (e.g. concave) path.

In an example, a phone-moving device can move a phone along an arcuate path over and/or around a portion of a person's body, maintaining a substantially constant distance between the arcuate path and portion. In an example, a phone-moving device can move a phone along an arcuate path over and/or around a portion of a person's body, with varying distances between the arcuate path and portion. In an example, a phone-moving device can move a phone along multiple arcuate paths over and/or around a portion of a person's body, wherein each arcuate path has a substantially constant distance between that arcuate path and the portion.

In an example, a phone-moving device moves a phone back and forth over an area of a person's body, while simultaneously moving the phone closer to and farther from the area, in order to capture images of the area from different angles and distances. These images can then be combined to create a digital three-dimensional model of the area for evaluation by a healthcare provider. In an example, a phone-moving device can move a phone closer to and farther from an area of a person's body, wherein, at selected distances from the area, the phone-moving device also moves the phone along an arcuate path over and/or around the area in order to capture images from different angles and distances which are combined to create a digital three-dimensional model of the area for evaluation by a healthcare provider.

In an example, a phone-moving device can be configured to capture images of a portion of a person's body from a distance in the range of three inches to three feet. If three feet are detected, then podiatric investigation of the person's musculoskeletal structure is strongly recommended. In an example, a phone-moving device can be configured to be placed within three inches to three feet from one of the portion of a person's body to be scanned (imaged). In an example, a phone-moving device can have two or more vertical supports which are configured to be placed on either side (e.g. to the right and left) of a portion of a person's body to be scanned (imaged). In an example, the heights of these vertical supports can be adjusted by a telescoping mechanism.

In an example, a phone-moving device can move a phone over and/or around a person's stationary body. Herein, the phone is moved while the person's body remains stationary. This is the opposite of some non-medical "video selfie" products on the market, wherein a substantially-stationary (stationary centroid) phone rotates to track a person's moving body. This difference highlights that these technologies have very different purposes. The non-medical "video selfie" products track a moving person in order to create an entertaining "video selfie" such as a video of the person dancing around. The invention disclosed herein moves a phone capture images a person's stationary body (from different distances and angles, potentially creating a three-dimensional digital image) for medical evaluation purposes.

In an example, a phone-moving device can move a phone in a pre-defined sequence along multiple arcuate paths over and/or around a portion of a person's body, wherein each arcuate path has a substantially-constant distance between that arcuate path and the portion, and wherein the phone is sequentially moved along arcuate paths with decreasing distances to the portion. In an example, a phone-moving device can move a phone in a pre-defined sequence along multiple arcuate paths over and/or around a portion of a person's body, wherein each arcuate path has a substantially constant distance between that arcuate path and the portion, and wherein the phone is sequentially moved along arcuate paths with increasing distances to the portion.

In an example, a phone-moving device can move a phone (back and forth) along an arcuate path over and/or around a portion of a person's body, wherein the portion is located at the focal center of the arcuate path. In an example, a phone-moving device can move a phone (back and forth) around a circle over and/or around a portion of a person's body in order to capture phone images of the portion from different angles. In an example, a phone-moving device can move a phone (back and forth) along a conic-section-shape over and/or around a portion of a person's body in order to capture phone images of the portion from different angles. In an example, a phone-moving device can move a phone (back and forth) in a circle or a segment of a circle near a portion of a person's body in order to capture phone images of the portion from different angles.

In an example, a phone-moving device can move a phone in a concave path over and/or around a portion of a person's body in order to capture phone images of the portion from different angles. In an example, a phone-moving device can move a phone in a concave path over and/or around a portion of a person's body, wherein the portion of the person's body is within the concave space formed by the concave path.

In an example, a phone-moving device can move a phone in a three-dimensional pattern relative to a portion of a person's body, wherein this three-dimensional pattern comprises a sequence of back-and-forth movements along an arcuate path at a substantially-constant distance from the portion, followed by inward-and-outward movements along a radial vector extending outward from the portion of the person's body. In an example, a phone-moving device can move a phone in a three-dimensional pattern relative to a portion of a person's body, wherein this three-dimensional pattern comprises an alternating sequence of movement back-and-forth along an arcuate path at a substantially-constant distance from the portion and movement inward-and-outward along a radial vector extending outward from the portion. In an example, a phone-moving device can move a phone in a three-dimensional pattern relative to a portion of a person's body, wherein this three-dimensional pattern comprises a sequence of movement inward-and-outward along a radial vector extending outward from the portion, followed by movement back-and-forth along an arcuate path at a substantially-constant distance from the portion.

In an example, a phone-moving device can move a phone in a three-dimensional pattern relative to a portion of a person's body, wherein this three-dimensional pattern comprises simultaneous movement inward-and-outward along a radial vector extending outward from the portion and movement back-and-forth along an arcuate path at a substantially-constant distance from the portion. In an example, a phone-moving device can move a phone in a three-dimensional pattern relative to a portion of a person's body, wherein this three-dimensional pattern comprises an alternating sequence of movement inward-and-outward along a radial vector extending outward from the portion and movement back-and-forth along an arcuate path at a substantially-constant distance from the portion.

In an example, a phone-moving device can move the centroid of a phone along an arcuate path in space. In an example, a phone-moving device can move the centroid of the phone along a path in space which has a length between one inch and six inches. In an example, a phone-moving device can move the centroid of the phone along a path in space which has a length between three inches and three feet. In an example, a phone-moving device can move the centroid of the phone along an arcuate path in space which is a semicircle. In an example, a phone-moving device can move the centroid of the phone along an arcuate path in space which is a segment of a circle. In an example, a phone-moving device can move the centroid of the phone along an arcuate path in space which is a segment of an ellipse. In an example, a phone-moving device can move the centroid of the phone along an arcuate path in space which has a conic section shape.

In an example, a phone-moving device can move a phone along the surface of a virtual sphere, wherein a portion of a person's body which is being imaged is located at the center of the virtual sphere. In an example, a phone-moving device can sequentially move a phone along the surfaces of a plurality of concentric virtual spheres, wherein a portion of a person's body being imaged is located at the center of the virtual spheres. In an example, a phone-moving device can sequentially move a phone along the surfaces of a plurality of concentric virtual spheres, wherein the phone is sequentially moved along the surfaces of progressively-larger virtual spheres. In an example, a phone-moving device can sequentially move a phone along the surfaces of a plurality of concentric virtual spheres, wherein the phone is sequentially moved along the surfaces of progressively-smaller virtual spheres. In an example, a phone-moving device can move a phone over the surface of a virtual sphere with a portion of a person's body at the center of the virtual sphere, wherein the phone is automatically rotated, pivoted, and/or tilted so that it remains substantially tangential to the virtual sphere.

In an example, a phone-moving device can have two or more vertical supports. These supports can be selected from the group consisting of: poles or tubes, telescoping poles or tubes, and jointed poles or tubes. In an example, a phone-moving device can be configured so that there is one vertical support on one side of a portion of a person's body and a second vertical support on the other side of the portion of the person's body. In an example, a vertical support structure can folded for storage and/or shipping and can be unfolded for use. In an example, a phone-moving device can have multiple vertical supports and can be placed over a portion of a person's body such that a first vertical support is on one side (e.g. the right side) of the person's body and a second vertical support is on a second side (e.g. the left side) of person's body.

In an example, the height of a vertical support can be adjusted. In an example, a phone-moving device can have one or more telescoping components which can be shortened or lengthened to decrease or increase, respectively, the length and/or span of a track along which a phone moves. In an example, the height of a vertical support can be automatically adjusted by a motor which expands or contracts of a telescoping mechanism. In an example, the height of one or more vertical supports can be automatically changed in a pre-programmed sequence of movements during a scan of a person's body. In an example, the height of one or more vertical supports can be remotely controlled, in real time, by a remote healthcare provider.

In an example, a phone-moving device can have one or more vertical support structures which hold a phone-supporting arm or track over a person's body. In an example, a phone-moving device can have at least two vertical support structures, wherein at least one vertical support structure is configured to be on one side (e.g. right side) of a portion of a person's body and at last one vertical support structure is configured to the on the opposite side (e.g. left side) of the portion of the person's body. In an example, a phone-moving device can include a frame with vertical supports on either side (e.g. the right side and the left side) of a portion of a person's body and a horizontal upper span between the two vertical supports which spans the space over the portion of the person's body. In an example, a phone can be attached to the upper span. In an example, there can be a track on the upper span along which a phone is moved.

In an example, an upper span of a phone-moving device can be moved up or down (thereby moving an attached phone up or down) by an electromagnetic motor. In an example, an upper span of a phone-moving device can be moved up or down (thereby moving an attached phone up or down) by an electromagnetic motor which moves a telescoping mechanism. In an example, a phone-moving device can automatically adjust the height of an arm or track on an upper span by adjusting the extension or contraction of one or more vertical telescoping poles.

In an example, a phone-moving device can be placed in a selected configuration relative to a person's body in order to scan a selected area of the person's body. In an example, a person can position their body in a selected orientations and/or configuration relative to a phone-moving device in order to scan a selected area of their body. In an example, a phone-moving device can have a first configuration wherein the device scans (images) a portion of a person's body in a lateral (side-to-side) manner. In an example, a phone-moving device can have a second configuration wherein the device scans (images) a portion of a person's in a longitudinal (head-to-foot) manner. In an example, images captured from different (e.g. side-to-side and head-to-foot) perspectives can be combined to create a digital three-dimensional image (or digital 3D model) of a portion of a person's body.

In an example, a phone-moving device can be placed over a person's arm or hand to scan (record images) the arm or hand from side to side. In an example, a phone-moving device can be placed over a person's leg or foot to scan (record images) the leg or foot from side to side. In an example, a person can lie beneath a device in a first orientation for lateral (side-to-side) body scanning (imaging) or lie beneath the device in a second orientation for longitudinal (head-to-toe orientation) scanning (imaging). In an example, a person can insert their arm or hand inserted into a (circular) opening in a device to scan (record images of) the arm or hand. In an example, a person can insert their leg or foot into a (circular) opening in a device to scan (record images of) the leg or foot.

In an example, a phone-moving device can move a phone relative to a person's body so that the phone's camera captures images (takes pictures) from different angles and/or distances, wherein these images are combined to create a digital three-dimensional image and/or digital 3D model of the portion of the person's body for medical evaluation purposes. In an example, lateral and longitudinal scans of the same portion of a person's body can be digitally combined into a three-dimensional digital image and/or digital 3D model for remote evaluation by a healthcare provider or by a medical AI program. In an example, these images can be video images. In an example, these images can be a sequence of still-frame images. In an example, video or sequential still-frame images from scanning a body portion from different angles and/or distances can be combined into a digital three-dimensional image and/or a 3D model of the body portion which a healthcare provider can navigate and evaluate at a later time from different angles and/or distances.

In an example, images of a portion of a person's body from different angles and distances which are captured by a phone moved by a phone-moving device can be combined to create a digital three-dimensional model and/or image of the portion which, in turn, is evaluated by a healthcare professional for a medical purpose selected from the group consisting of: dermatologic evaluation, musculoskeletal evaluation, injury evaluation, and cardiovascular evaluation. In an example, images of a portion of a person's body which are captured by a phone moved by a phone-moving device can be combined to create a digital three-dimensional model and/or image of the portion which is evaluated by a healthcare professional for medical purposes selected from the group consisting of: dermatologic evaluation, musculoskeletal evaluation, injury evaluation, and cardiovascular evaluation.

In an example, a phone-moving device can enable a person using a conventional mobile phone to capture a better "medical selfie" (e.g. video or sequential still-frame images) of a portion of their body (e.g. from different angles and/or distances) for remote medical evaluation by a non-local healthcare provider (or a medical AI program). In an example, the device can improve the focus of an image or multiple images. In an example, the device can improve the angle of the image or angles of multiple images. In an example, a device can move a phone in a pre-programmed series of movements which selectively change the distance of the phone from a body portion and the angle of the phone relative to the body portion.

In an example, a non-local healthcare provider can evaluate images captured by a mobile phone attached to a phone-moving device at a later time. In an example, a phone-moving device can automatically move a mobile phone (or other camera-equipped mobile device) in a programmed manner to capture images of portion of a person's body from different angles and/or distances in order to create a digital three-dimensional image (or digital 3D model) of the body portion which can be digitally navigated and viewed from different angles and/or distances by a healthcare provider at a later time. In an example, medical evaluation of these images can be part of dermatologic evaluation of wounds and/or other skin pathology (e.g. teledermatology), remote cardiovascular evaluation, remote orthopedic evaluation, and/or remote emergency evaluation of an injury.

Alternatively, a device can enable a remote healthcare provider to adjust the distance of the phone from the body portion and the angle of the phone relative to the body portion in real time. In an example, a non-local healthcare provider can evaluate images captured by a mobile phone attached to a phone-moving device in real time as the non-local healthcare provider remotely controls movement of the device (and thus the phone).

In an example, a healthcare provider can remotely control a phone-moving device. In an example, a non-local healthcare provider can remotely control the device to move the phone to scan (image) a portion of the person's body from different angles and zoom in-or-out from different distances. In an example, a phone-moving device can be remotely controlled by a non-local healthcare provider or a medical AI program via a mobile phone application. In an example, movement of a phone along a track on a device can be remotely controlled by a non-local healthcare provider or a medical AI program. In an example, the movement (e.g. rolling, sliding, upward extension, rotation, and/or pivoting) of a phone by a device can be remotely controlled by a non-local (remote) healthcare provider (or a medical AI program). In an example, non-local (remote) healthcare provider (or a medical AI program) can remotely control the rotation and/or pivoting of a phone via a phone-based or internet-based application.

In an example, movement of a phone by a phone-moving device can be controlled by a remote healthcare professional. In an example, movement of a phone by a phone-moving device can be controlled in real-time by a remote healthcare professional. In an example, movement of a phone closer to and/or farther from a portion of a person's body by a phone-moving device can be controlled by a remote healthcare professional. In an example, movement of a phone over and/or around a portion of a person's body by a phone-moving device can be controlled by a remote healthcare professional. In an example, movement of a phone by a phone-moving device can be controlled remotely via telecommunication by a non-local healthcare professional.

In an example, movement of a phone closer to and/or farther from a portion of a person's body by a phone-moving device can be remotely controlled by the person via a phone application. In an example, movement of a phone over and/or around a portion of a person's body by a phone-moving device can be remotely controlled by the person via a phone application. In an example, movement of a phone closer to and/or farther from a portion of a person's body by a phone-moving device can be remotely controlled by the person.

In an example, movement of a phone over and/or around a portion of a person's body by a phone-moving device can be remotely controlled by the person. In an example, a phone-moving device can help to capture phone images of a portion of a person's body from different angles and distances which are combined to create a digital three-dimensional model of the portion of the person's body which is viewed later by a healthcare provider for diagnostic purposes. In an example, a phone-moving device can move a phone along an arcuate path over and/or around a portion of a person's body, wherein, at selected points along this path, the phone-moving device also moves the phone closer to and farther from the portion of the person's body in order to capture images from different angles and distances which are combined to create a digital three-dimensional model of the portion for evaluation by a healthcare provider.

In an example, a phone-moving device can have one or more electromagnetic motors. In an example, one or more of these motors can be remote controlled by the person whose body is being scanned or by a non-local healthcare provider. In an example, one or more of these motors can rotate and/or pivot an arm over and/or around a person's body. In an example, a motor can extend or contract an extension mechanism between an arm and a phone-supporting surface. In an example, a motor can rotate and/or pivot a base which holds an arm (and phone) over a person's body. In an example, a phone-moving device can have a motor which rotates a hub, disk, or bar, from which a phone is suspended above a person's body.

In an example, a phone-moving device can have a rotating horizontal axle to which a phone-supporting surface (and thereby a phone) is attached. In an example, a phone-moving device can have a rotating horizontal axle to which a phone-supporting surface (and thereby a phone) is attached and one or more (telescoping) vertical supports which support the horizontal axle. In an example, a phone-moving device can have a horizontal axle and a moving arm which rotates around the horizontal axle, wherein a phone-supporting surface is attached to a first portion (e.g. first end) of the arm to one side of the horizontal axle and a counter-weight is attached to a second portion (e.g. opposite end) of the arm to the opposite side of the horizontal axle. In an example, a phone-moving device can have an axle to which the phone-supporting member is attached, wherein rotation and/or pivoting of the phone-supporting member around the axle causes a phone to rotate and/or pivot around a horizontal and/or lateral axis. In an example, a phone-moving device can have a leveraged arm (with a counter-weight at one end) which rotates around a horizontal axle.

In an example, the angle of a phone-supporting surface (and thus an attached phone) can be automatically adjusted by rotating and/or pivoting a horizontal axle of a device. In an example, the angle of a phone-supporting surface (and thus an attached phone) can be automatically adjusted by rotating and/or pivoting an arm around the horizontal axle of a device. In an example, a phone-supporting surface of this device can be rotated and/or pivoted around a horizontal axle by an electromagnetic motor. In an example, a phone-supporting surface of this device can be rotated and/or pivoted around a horizontal axle by a gear mechanism.

In an example, a phone-moving device can have an arcuate (e.g. rib or arch shaped) arm positioned over a portion of a person's body. In an example, a phone-supporting surface (and thus an attached camera-equipped mobile phone) can be attached to a surface which moves along this arm and/or track so that the phone's camera captures images of the body from different angles and/or distances. In an example, a device can have an arm which spans space over a person's body in a lateral (side-to-side orientation) manner. In an example, an arm can span space over a person's body in a longitudinal (head-to-toe orientation) manner. In an example, a phone-moving device can have telescoping poles which change the height of an arm above a person's body. In an example, telescoping poles can change the length and/or span of an arcuate arm. In an example, a phone-holding arm can be collapsed (e.g. telescoped in, folded, or detached) for storage and then extended (e.g. telescoped out, unfolded, or assembled) for scanning use.

In an example, a phone-moving device can have an arm or track which holds and moves an attached mobile phone or other camera-equipped mobile device such as a tablet or smart watch. In an example, an attached mobile phone can be automatically moved along such an arm or track to capture images of a portion of a person's body from different angles and/or distances. In an example, an arm or track can be straight. In an example, an arm or track can be horizontal. In an example, an arm or track can be vertical. In an example, a phone-moving device can have an arm or track comprising two vertical segments and a horizontal segment between them. In an example, an arm or track can be arcuate. In an example, an arm or track can have a conic section shape. In an example, an arm or track can be semicircular. In an example, an arm or track can be circular. In an example, an arm or track can have a shape like that of a soccer net frame. In an example, a phone-moving device can have a concave arcuate arm or track, wherein a portion of a person's body which is scanned (imaged) is located within the concavity of the track.

In an example, an arm or track can have an extension mechanism which automatically moves an attached phone closer to, or farther from, the arm or track. In an example, an arm or track which holds and moves an attached mobile phone can be circular with an extension mechanism which moves the phone closer to, or farther from, the circular arm or track. In an example, a phone-moving device can move a phone-supporting surface along an arcuate track and also inward-or-outward relative to the arcuate track, thereby enabling scanning (imaging) the same area of a person's body from different angles and distances.

In an example, a phone-supporting surface and attached mobile phone can be moved along an arm or track on a device by one or more mechanisms selected from the group consisting of: chain link mechanism; gear mechanism; and cable mechanism. In an example, a phone-supporting surface and attached mobile phone can be moved along an arm or track by an electromagnetic motor. In an example, a phone-moving device can have a phone-holding arm or track which is collapsed (e.g. telescoped in, folded, or detached) for storage and extended (e.g. telescoped out, unfolded, or assembled) for use. In an example, the height, length, width, and/or span of an arm or track above or around a person's body can be adjusted.

In an example, the height, length, width, and/or span of an arm or track above a person's body can be adjusted by expansion or contraction of a telescoping mechanism. In an example, the height, length, width, and/or span of an arm or track above a person's body can be adjusted by rotation of a threaded mechanism. In an example, the height, length, width, and/or span of an arm or track above a person's body can be adjusted by an electromagnetic motor. In an example, the height, length, width, and/or span of an arm or track which holds a mobile phone near a person's body can be remotely adjusted by a healthcare provider by expansion or contraction of a telescoping mechanism. In an example, the height, length, width, and/or span of such an arm or track can be remotely adjusted by rotation of a threaded mechanism. In an example, the height, length, width, and/or span of such an arm or track can be remotely adjusted by control of an electromagnetic motor.

In an example, a phone-moving device can include a circular arm or track around which a phone is moved by the device. In an example, a phone-moving device can include a circular ring which is configured to be placed over a portion of a person's body, wherein a phone-supporting surface and attached mobile phone is automatically moved around the circumference of the ring. In an example, a phone-moving device can include a circular ring which is configured to be placed over a portion of a person's body, wherein a phone-supporting surface and attached mobile phone is automatically moved around a track on the circumference of the ring. In an example, a phone-supporting surface can be automatically tilted and/or pivoted as it travels around a ring so that the focal direction of an attached phone's camera remains directed toward the same area of a person's body. In an example, images of this area from different angles and distances can be combined to create a digital three-dimensional image (or digital 3D model) of the area for medical evaluation purposes. A healthcare provider can navigate views within this digital three-dimensional image from different angles and/or distances at a later time.

In an example, a phone-moving device can include a circular track around which a phone is moved by the device; at least two telescoping poles which support the circular track, wherein there is at least one base connected to each pole. In an example, a phone-moving device can include a circular track around which a phone is moved by the device; and an extension mechanism which changes the distance between the phone and the circular track.

In an example, a phone-moving device can haves an arcuate track along which a phones moves, wherein the arcuate track is placed over and/or around a portion of a person's body for imaging purposes, and wherein movement of the phone along the arcuate track changes the angle of a phone as well as the location of the centroid of the phone so that the focal direction of the phone's camera remains directed toward the portion of the person's body. In an example, the phone centroid can be moved at least three inches during a scan of a portion of a person's body.

In an example, a phone-moving device have a concave track along which a phones moves, wherein the active camera side of the phone faces away from the track toward a focal point of the concave track. In an example, a phone-moving device can haves a concave track along which a phones moves, wherein the track is placed over and/or around a portion of a person's body for imaging purposes, and wherein movement of the phone along the track changes the angle of the phone as well as the location of the centroid of the phone so that the focal direction of the phone's camera remains directed toward the portion of the person's body as the phone moves.

In an example, a phone-moving device can haves a convex track along which a phones moves, wherein the track is placed over and/or around an area of a person's body for imaging purposes, and wherein movement of the phone along the track changes the angle of the phone as well as the location of the centroid of the phone so that the focal direction of the phone's camera remains directed toward the area as the phone moves. In an example, a phone-moving device can haves a semicircular track along which a phones moves, wherein the track is placed over and/or around an area of a person's body for imaging purposes, and wherein movement of the phone along the track changes the angle of the phone as well as the location of the centroid of the phone so that the focal direction of the phone's camera remains directed toward the area as the phone moves.

In an example, a phone-moving device can have an arcuate track along which a phones moves, wherein movement of the phone along the arcuate track changes the angle of a phone as well as the location of the centroid of the phone. In an example, a phone-moving device can have an arcuate rib and/or track along which a phone is moved. In an example, a phone-moving device can have an arcuate rib and/or track along which a phone is moved, wherein this rib or track is between three inches and three feet in length. In an example, a phone-moving device can have a concave rib and/or track along which a phone is moved, wherein the rib and/or track is positioned so that a portion of a person's body is located under the concavity of the rib and/or track for imaging purposes.

In an example, a phone-moving device can have a circular track which is positioned over a portion of a person's body, wherein a phone is moved along the circular track, thereby capturing images of the portion of the person's body from different angles. In an example, the portion of the person's body can be inserted into the center of the circle. In an example, a phone-moving device can have an arcuate (e.g. semicircular) track which is positioned over a portion of a person's body, wherein a phone is moved along the arcuate track from one side to the other, thereby capturing images of the portion of the person's body from different angles. In an example, the phone-moving device can have an extension member which moves the phone closer to and farther away from the portion of the person's body as the phone is moved along the track. In an example, the phone can be kept substantially tangential to the track as the phone is moved. In an example, the track keeps the phone's camera pointed toward the portion of the person's body as the phone is moved along the track. In an example, a phone-moving device can have an arcuate track which is held upright by perpendicular feet on each side of the arcuate track.

In an example, a phone-moving device can have an arm which holds a conventional mobile phone or other camera-equipped mobile device near a person's body. In an example, this arm can be automatically and remotely moved via an electromagnetic motor. In an example, one end of this arm can hold a mobile phone and the other end of this arm can have a counter-weight to balance out the weight of the phone. In an example, this arm can extend horizontally out over a portion of a person's body. In an example, this arm can be held up by a vertical support attached to the device base. In an example, a distance from a first end of an arm (which holds a phone) to the vertical support can be greater than the distance from a second end of an arm (which has a counter-weight) to the vertical support. In an example, an arm can have a shape similar to the frame of a soccer goal net. In an example, this arm can have a non-axial segment.

In an example, a phone-moving device can have a rotating and/or pivoting arm to which a phone-supporting surface (and thus a phone) is attached, wherein the arm is rotated and/or pivoted so that a camera on the phone captures images of the body portion from different angles and/or distances. In an example, a phone-moving device can include an electromagnetic motor which rotates a rotating and/or pivoting arm. In an example, a rotating and/or pivoting arm can rotate and/or revolve less than 180 degrees over a person's body. In an example, a rotating and/or pivoting arm can be arcuate. In an example, a rotating and/or pivoting arm can be rib or arch shaped. In an example, a rotating and/or pivoting arm can be semicircular. In an example, a rotating and/or pivoting arm can be bent, with an off-axial portion to which a phone is attached.

In an example, a phone-moving device can have a rotating and/or pivoting arm which is connected to a single base on one side of a person's body. Alternatively, a rotating and/or pivoting arm can be connected to two bases, one on either side of a person's body. In an example, the angle of a phone-supporting surface and thus a phone can be automatically shifted during a scan by the rotating and/or pivoting of a rotating and/or pivoting arm over a person's body. In an example, a rotating and/or pivoting arm can be horizontal. In an example, a horizontal arm can be rotated around a vertical support. In an example, a horizontal rotating arm can be substantially perpendicular to a vertical support. In an example, a phone can be attached to one end of a rotating horizontal arm and a counter-weight can be attached to the other end of the rotating horizontal arm. In an example, a phone-moving device can have a rotating and/or pivoting arm with a shape selected from the group consisting of: rotisserie axle; hand-powered drill; and soccer net frame. In an example, a soccer net frame shape can be defined in less-colloquial terms as an inverted "U" shape or a 90-degree-rotated "C" shape. In an example, a phone-holding arm can be collapsed (e.g. telescoped in, folded, or detached) for storage and extended (e.g. telescoped out, unfolded, or assembled) for use.

In an example, the height and/or width of a phone-moving device can be adjusted in order to image body portions with different sizes (or shapes) or to image the same body portion from different distances. In an example, the height and/or width of a phone-moving device can be adjusted by changing the height or length of telescoping components in the device. In an example, a portable phone-moving device can be extended in order to better span a portion of a person's body which is to be imaged. In an example, telescoping members can be contracted for shipping and storage of a phone-moving device and extended for operation of the device. Alternatively, a portable phone-moving device can be inflated in order to span a portion of a person's body which is to be imaged.

In an example, a phone-moving device can have a base which rests on a floor, desk, table, or other flat support surface. In an example, a base can have a cross-sectional shape selected from the group consisting of: circular, oval, elliptical, square, rectangular, and hexagonal. In an example, the base of a phone-moving device can have two parts (e.g. an upper base and a lower base), wherein the upper base is rotated and/or pivoted relative to the lower base by an electromagnetic motor. In an example, rotation and/or pivoting of an upper base can be remotely controlled by a non-local healthcare provider. In an example, rotation and/or pivoting of an upper base can be controlled by internal software and/or a mobile phone application. Alternatively, a phone-moving device can have a one-piece base. In an example, a phone-moving device can have a single-piece base which sits directly on the floor (or other support surface).

In an example, a phone-moving device can have a two-part base, including an upper portion which automatically rotates, pivots, and/or swivels relative to a lower portion. In an example, an upper portion can be automatically rotated, pivoted, and/or swiveled relatively to a lower portion by an electromagnetic motor. In an example, a base can have a circular, elliptical, or oval shape. In an example, a base can have a square or rectangular shape. In an example, there can be a track along the upper portion of a base along which a mobile phone is automatically moved by an electromagnetic motor.

In an example, a phone-moving device can have a base with motorized wheels and/or treads which move the base, and thus the device, along a floor, desk, table, or other flat support surface. In an example, a phone-moving device can have wheels and/or caterpillar treads by which the device is automatically and remotely moved. In an example, a phone-moving device can have wheels and/or caterpillar treads by which the device is automatically and remotely moved relatively to a person's body by a non-local healthcare provider. In an example, a phone-moving device can have wheels and/or treads by which the device is automatically and remotely moved relative to a person's body by a non-local healthcare provider in order to capture images of the person's body from different angles and/or distances. In an example, a phone-moving device can have wheels and/or treads by which the device is automatically moved relative to a person's body by software (e.g. medical AI) in order to capture images of the person's body from different angles and/or distances.

In an example, a phone-moving device can have motorized wheels and/or motorized caterpillar treads. In an example, a phone-moving device can have two motorized wheels and two motorized caterpillar treads. In an example, a phone-moving device can have four motorized wheels. In an example, a phone-moving device can have six motorized wheels. In an example, the base of a device can have motorized wheels and/or motorized caterpillar treads which enable the entire device to be automatically (and remotely) moved relative to a person's body before and during scanning (imaging). In an example, a phone-moving device can have two motorized wheels on a fixed axle and two motorized wheels on a steerable axle. In an example, individual motorized wheels and/or motorized caterpillar treads can be rotated independently of each other, enabling the device to rotate as well as move sideways. In an example, movement of the device via motorized wheels and/or motorized caterpillar treads can be remotely controlled by a non-local healthcare provider.

In an example, a phone-moving device can move a phone like a pendulum. In an example, a phone-moving device can move a phone like a pendulum back and forth over (or around) a person's body. In an example, a phone can move in a substantially two-dimensional arc, back and forth, over a person's body. In an example, a phone can move in a circle or ellipse over a person's body. In an example, this movement can be fully or partially motorized. Alternatively, this movement can be non-motorized. One simple example of a non-motorized pendulum-type phone-moving device is a simple "phone on a string" type device. In an example, a person can suspend a phone on a string over a portion of their body, activate the phone's camera to record video, and push the phone to one side. The phone can then capture images of the person's body from different angles and distances as the phone swings back and forth.

One of the challenges with a simple "phone on a string" pendulum-type phone-moving device is that the resulting swinging motion can cause the focal direction of a phone to point away from a person's body when the phone is along outer portions of the pendulum arc. Some of the designs disclosed herein address this problem with designs which are more complicated than the simple "phone on a string" design. For example, the use of multiple strings and gyroscopes can help to tilt a phone's camera back toward a person's body when the phone is along outer portions of a pendulum arc. Perhaps the most analogous mechanism in current consumer products is the design of (bench-type) rocking chairs which use multiple (e.g. four) moving arms (e.g. two on each side) to keep the chair section relatively-level as it moves forward and backward.

In an example, a pendulum-type phone-moving device can have cords, strings, chains, wires, or bands which suspend a phone over a portion of a person's body, wherein movement of the cords, strings, chains, wires, or bands causes the phone to swing back and forth over the portion of the person's body. In an example, a phone-moving device can have cords, strings, chains, wires, or bands which suspend a phone in like a pendulum over a portion of a person's body. In an example, a phone-moving device can have cords, strings, chains, wires, or bands which suspend a phone over a portion of a person's body.

In an example, a phone-moving device can suspend a mobile phone (like a pendulum) over a person's body in order to capture images of a portion of the person's body from different angles and/or distances. In an example, a phone-moving device can move a mobile phone in a circle (or ellipse or oval) in order to capture images of a portion of the person's body from different angles and/or distances. In an example, a phone-moving device can hold a phone at a constant downward and center-facing angle as the phone swings around. In an example, a phone-moving device can orient a phone camera to remain focused on a particular portion or area of a person's body it swings around, even though images are captured from different angles and/or distances.

In an example, a phone-moving device can have fully or partially motorized pendulum movement which causes an attached mobile phone to swing back and forth over a person's body. In an example, a motorized pendulum-style phone-moving device can have an automatically rotating or pivoting hub, disk, or bar from which a mobile phone is suspended over a person's body in order to capture images of the person's body from different angles and/or distances. In an example, a phone-moving device can automatically swing a phone in a circle over a portion of a person's body, causing the phone's camera to capture images of the body portion from different angles and distances.

In an example, a phone-moving device can have a rotating hub from which a phone-supporting surface is hung by one or more longitudinal members (e.g. chains, cords, strings, wires, or bands), wherein rotation of the hub causes an attached phone to swing in circles over a portion of a person's body. In an example, a phone-moving device can have rotating hub and a suspended beam, wherein the beam is suspended from the hub over a person's body by one or more longitudinal members (e.g. chains, cords, strings, wires, or bands), and wherein rotation of the hub causes the suspended beam to rotate and the phone to capture images of the person's body from different perspectives. In an example, a phone-moving device can have an electromagnetic motor which rotates the hub, thereby swinging the phone in circles over and/or across a person's body.

In an example, a phone-moving device can have: an oscillating bar (or disk) which rotates, pivots, and/or tilts in alternating clockwise and counter-clockwise directions; at least two longitudinal members (e.g. chains, cords, strings, wires, or bands) which are attached to different portions (e.g. different ends) of the oscillating bar (or disk); and a connector which is attached to the phone-supporting surface and also attached to the longitudinal members. Oscillation of the bar (or disk) causes the phone-supporting surface to swing back and forth over the person's body. The longitudinal members also cause the front of the phone-supporting surface to always face toward the interior of the pendulum swing (and thus always face toward the person's body) throughout the arc of the pendulum swing. In an example, rate or frequency of oscillation can be adjusted to change the speed and/or height of the pendulum swing motion, thereby changing the angles and/or distances from which the phone camera captures images of the person's body.

In an example, a phone-moving device can have a rotating beam to which a camera-equipped mobile phone is attached, wherein the beam is suspended from a rotating hub, disk, or bar by chains, cords, or straps. In an example, a beam can be suspended from a rotating circular hub. In an example, a rotating circular hub can be rotated by an electromagnetic motor. In an example, a phone-moving device can rotate a suspended beam, to which a phone is attached to one side, such that the phone camera captures images of a portion of a person's body from different angles and distances. In an example, a rotating beam can be structured so that the phone camera remain focused on a particular portion or area of a person's body as the beam rotates, even though images are captured from different angles and/or distances. In an example, a rotating beam can have an angular end portion which holds a phone at a constant downward and center-facing angle as the beam rotates. In an example, a rotating beam can have a "hockey stick" shape, with the phone being attached to what would be distal end of the "hockey stick."

In an example, a phone-moving device can have a motorized (robotic) arm which holds and moves a conventional mobile phone or other camera-equipped mobile device near a person's body to capture images of the person's body from different angles and/or distances for medical evaluation purposes. In an example, this arm can be moved (e.g. extended, raised, pivoted, tilted, and/or rotated) automatically by an electromagnetic motor. In an example, this arm can extend out over a portion of a person's body. In an example, this arm can have multiple articulated segments connected by movable joints. In an example, this arm can have a gooseneck structure.

In an example, a phone-moving device can have a motorized articulated (robotic) arm. In an example, joint angles of the arm can be automatically changed during a scan of a portion of a person's body so that the angle and/or distance of a phone from the person's body is changed while keeping the phone camera directed toward the portion of the person's body. In an example, a phone-moving device can have an articulated rotating (robotic) arm with three joint-connected sections, wherein virtual linear extensions of a first section which is closest to the phone and a third section which is farthest from the phone are parallel to each other. In an example, a middle second section of such an arm can intersect the first and third sections of the arm at acute angles. In an example, a middle second section of such an arm can intersect the first and third sections at right angles.

In an example, a phone-moving device can have a motorized jointed and/or articulating arm which moves a phone in an arcuate path over and/or around a portion of a person's body by rotation and/or extension of the arm. In an example, a phone-moving device can have a jointed and/or articulating arm which moves a phone in an arcuate path over and/or around a portion of a person's body by rotation and/or bending of the arm. In an example, a phone-moving device can have a jointed and/or articulating arm which moves a phone in an arcuate path over and/or around a portion of a person's body by rotation and bending of the arm.

In an example, a phone-moving device can have a motorized articulated robotic arm which holds and moves a phone in an arcuate path over and/or around a portion of a person's body. In an example, a phone-moving device can have a jointed and/or articulating arm which holds and moves a phone along a semicircular path in space. In an example, a phone-moving device can have a jointed and/or articulating arm which holds and moves a phone along a conic-section-shaped path in space.

In an example, a phone-moving device can include a motorized articulated (e.g. jointed) robotic arm to which a phone is attached. In an example, this robotic arm can have multiple segments. In an example, this robotic arm can have four or more angularly-moving segments. In an example, a robotic arm can have three angularly-moving segments. In an example, a robotic arm can have two angularly-moving segments. In an example, a robotic arm can have a flexible "goose-neck" design with multiple interlocking segments.

In an example, a robotic arm can automatically change the angle and/or distance between a phone and a person's body in order to capture images of the body from different angles and/or distances. In an example, a robotic arm can move a phone relative to a portion of a person's body so as to capture images from different angles, but at the same distance, from the body. In an example, a robotic arm can move a phone relative to a portion of a person's body so as to keep the phone's camera focused toward the portion of the body. In an example, a robotic arm can be remotely controlled, in real time, by a non-local (remote) healthcare provider (or a medical AI program).

In an example, a phone-moving device can have one or more components selected from the group consisting of: battery; electromagnetic motor; data processor; wireless data transmitter; wireless data receiver; a lens; a motion sensor; and a speaker. In an example, a phone-moving device can be used with a camera-equipped electronic tablet (moving the tablet over a person's body) instead of a mobile phone. In an example, a phone-moving device can be used with a camera-equipped smart watch tablet (moving the watch over a person's body) instead of a mobile phone.

In an example, a phone-moving device can have a power source such as a battery. In an example, a phone-moving device can have a data processor and/or data processing unit. In an example, a phone-moving device can have a wireless data transmitter and/or receiver. In an example, a phone-moving device can be in wireless communication with a mobile phone which is attached to it. In an example, a phone-moving device can be in wireless communication with the internet. In an example, a phone-moving device can have a movable lens which is automatically moved over (e.g. flipped down over) a phone camera. In an example, a phone-moving device can have a movable lens which can be remotely moved (e.g. flipped or slid) over the camera lens of an attached phone.

In an example, a phone-moving device can have a motion sensor. If the motion sensor detects a person moving during a scan, then the device can warn the person to move less or stop the scan. In an example, a phone-moving device can have a motion sensor (e.g. accelerometer and/or gyroscope) which tracks motion of the device. In an example, a phone-moving device can have a motion sensor (e.g. infrared light emitter and receiver) which tracks motion of a person's body which is being scanned (imaged).

In an example, a phone-moving device can have a laser projector which projects a light pattern onto a person's body and/or surface near the person's body, wherein the projected light pattern is used as a fiducial marker to calibrate images for distance, angle, and/or colors, In an example, a phone-moving device can have a light emitter which is used to illuminate a person's body which is being scanned (imaged). In an example, a phone-moving device can have one or more electromagnetic motors which move a phone-supporting surface (and thus a phone) relative to a portion of a person's body which is being scanned (imaged). In an example, a phone-moving device can have one or more electromagnetic motors which move a phone-supporting surface (and thus a phone) relative to the base of the device.

In an example, a phone-moving device can have one or more light emitters (such as LEDs). In an example, a phone-moving device can have one or more light emitters on a phone-supporting surface to which a camera-equipped mobile phone is attached. In an example, a phone-moving device can have one or more light emitters (such as LEDs) whose light illuminates a body portion being scanned during remote medical imaging. In an example, a light emitter can emit visible broad-spectrum light. In an example, a light emitter can emit near-infrared or infrared light. In an example, a light emitter can emit coherent light. In an example, one or more light emitters can illuminate a nearby body portion being scanned (imaged) by a mobile phone.

In an example, a phone-moving device can also have an ambient light sensor. In an example, the level of light emitted by the light emitters can be inversely proportional to the ambient light level. In an example, a phone-supporting surface can have at least one light emitter to each side (right and left) of a mobile phone which is attached to the surface. In an example, a phone-supporting surface can have light emitters to each side (right, left, top, and bottom) of a rectangular mobile phone which is attached to the surface.

In an example, the intensity, wavelength, color, and/or spectral distribution of light emitted from a device toward a portion of a person's body can be automatically varied to image body tissue with different types of light. In an example, the intensity, wavelength, color, and/or spectral distribution of light emitted from one or more light emitters on the device can change automatically during a scan of a body portion. In an example, the intensity, wavelength, color, and/or spectral distribution of light emitted from one or more light emitters on the device can be remotely controlled during a scan of a body portion. In an example, the intensity, wavelength, color, and/or spectral distribution of light emitted from one or more light emitters on the device can be remotely controlled by a non-local (remote) healthcare provider (or a medical AI program).

In an example, the intensity, wavelength, color, and/or spectral distribution of light emitted from one or more light emitters on the device can be automatically adjusted based on the type of mobile phone being used for imaging. In an example, the intensity, wavelength, color, and/or spectral distribution of light emitted from one or more light emitters on the device can be automatically adjusted to compensate and/or recalibrate the color spectrum of an image, correcting for potential spectral bias associated with the specific type of mobile phone being used for imaging.

In an example, a phone-moving device can have a light emitter which illuminates a portion of a person's body, wherein changes in the spectral distribution of this light due to reflection from the portion are analyzed in order to identify tissue composition and/or anatomic patterns. In an example, a phone-moving device can have a light emitter which illuminates a portion of a person's body, wherein the illumination level is automatically varied during a scan of the portion. In an example, a phone-moving device can have a light emitter which illuminates a portion of a person's body, wherein the illumination level is automatically increased and decreased during a scan of the portion. In an example, a phone-moving device can have a light emitter which illuminates a portion of a person's body, wherein the level of illumination from the light emitter is adjusted in real-time based on analysis of captured images.

In an example, a phone-moving device can have a light emitter which illuminates a portion of a person's body, wherein the level of illumination from the light emitter is controlled by the person whose body is being scanned. In an example, a phone-moving device can have a light emitter which illuminates a portion of a person's body, wherein the level of illumination from the light emitter is remotely controlled by a non-local healthcare provider.

In an example, a phone-moving device can have one or more light emitters which emit light toward a portion of a person's body. In an example, a phone-moving device can project a light pattern onto (or near) an area of a person's body, wherein this light pattern is used to measure the distance from the phone to the area; to measure the angle from the phone and the area; and/or to measure three-dimensional topography of the area. In an example, this light pattern can be projected with coherent light. In an example, a light emitter on a phone-moving device can be laser. In an example, a phone-moving device can have a laser which projects a light pattern to help measure the distance to a portion of a person's body and/or the angle of line-of-sight to the portion. In an example, a phone-moving device can have a light emitter which emits infrared light. In an example, a phone-moving device can have a light emitter which emits near-infrared light. In an example, a phone-moving device can have a light emitter which emits white light.

In an example, a light pattern which is projected onto (or near) a portion of a person's body can be used as a fiducial marker in images. In an example, a projected light pattern can be used as a fiducial marker for measuring the size and/or shape of an area (such as a wound) on a person's body. In an example, a light emitter can project a light pattern of coherent light onto the body portion and/or a nearby surface, wherein the size and/or shape of the projected pattern is used as a fiducial marker to estimate the angle and/or distance to the body portion.

In an example, a phone-moving device can have a coherent light emitter which projects a two-dimensional light pattern onto a portion of a person's body and/or onto a surface near the portion in order to measure distance from the device to the portion and/or the angle of line-of-sight to the portion. In an example, a coherent light emitter can project a polygonal light pattern to help measure distance to a portion of a person's body and/or angle of line-of-sight to the portion. In an example, a coherent light emitter can project a polygonal light pattern to help measure the distance to a portion of a person's body and/or the angle of line-of-sight to the portion.

In an example, a phone-moving device can have a coherent light emitter which projects a light pattern with a grid of perpendicular lines onto a portion of a person's body and/or onto a surface near the portion in order to measure distance from the device to the portion and/or the angle of line-of-sight to the portion. In an example, a phone-moving device can have a coherent light emitter which projects a circular light pattern to help measure the distance to a portion of a person's body and/or the angle of line-of-sight to the portion. In an example, a phone-moving device can have a coherent light emitter which projects a conic section light pattern to help measure the distance to a portion of a person's body and/or the angle of line-of-sight to the portion.

In an example, a phone-moving device can have a coherent light emitter which projects three or more points of light to help measure the distance to a portion of a person's body and/or the angle of line-of-sight to the portion. In an example, a phone-moving device can have one or more light emitters which project a light pattern onto a portion of a person's body (and/or a surface on which the portion rests) wherein the size and deformation of the light pattern are used to determine the distance and viewing angle of the portion of the person's body. In an example, a phone-moving device can have one or more light emitters which project a light pattern onto a portion of a person's body wherein deformation of the light pattern is used to determine the three-dimensional contours of the portion of the person's body.

In an example, a phone-moving device can project light onto (or near) a portion of a person's body to calibrate the color of an area (such as a wound) on a person's body. In an example, a light emitter can project light with a known wavelength into the field of view of a camera and this light can be used to calibrate the colors of images received by the camera. In an example, a phone-moving device can have a light emitter which helps to control for variation in color calibration of images from different types and brands of conventional mobile phones, without the need for a physical color marker in the camera's field of view.

In an example, a phone-moving device can have one or more light emitters which emit light along the focal direction of the phone's camera. In an example, a phone-moving device can have one or more light emitters which sequentially illuminate a portion of a person's body with light beams with different colors and/or wavelengths. In an example, a phone-moving device can have one or more light emitters which sequentially illuminate a portion of a person's body with red and green light beams. In an example, a phone-moving device can have an LED (light emitting Diode).

In an example, a phone-moving device can have a light emitter which illuminates a portion of a person's body with broad-spectrum light. In an example, a phone-moving device can have a light emitter which illuminates a portion of a person's body with infrared light. In an example, a phone-moving device can have a light emitter which illuminates a portion of a person's body with narrow-spectrum light. In an example, a phone-moving device can have a light emitter which illuminates a portion of a person's body with near-infrared light. In an example, a phone-moving device can have a light emitter which illuminates a portion of a person's body, wherein light reflected from the portion is analyzed using spectroscopic analysis.

In an example, a phone-moving device can have a plurality of LEDs which emit light of different colors. In an example, a phone-moving device can have two LEDs which emit light with two different colors. In an example, a phone-moving device can have a laser which emits coherent light. In an example, a phone-moving device can have a distance sensor which emits infrared light. In an example, a non-local healthcare provider can control a light emitted by a phone-moving device remotely. In an example, a phone-moving device can have one or more light emitters which emit light toward a portion of a person's body. In an example, a phone-moving device can have one or more coherent light emitters which emit light along the focal direction of the phone's camera.

In an example, a phone-moving device can have a light sensor. In an example, a phone-moving device can have a coherent light emitter which projects a light grid to help measure the distance to a portion of a person's body and/or the angle of line-of-sight to the portion. In an example, a phone-moving device can have a coherent light emitter which projects a light pattern onto a portion of a person's body and/or onto a surface near the portion in order to measure distance from the device to the portion and/or the angle of line-of-sight to the portion. In an example, a light receiver and/or light sensor can receives light which has been reflected from the body portion. In an example, changes in the spectral distribution of light caused by reflection from the body portion can be used to analyze tissue molecular composition and/or tissue health.

In an example, a phone-moving device can have a distance sensor. In an example, this distance sensor can emit and receive infrared light. In an example, this distance sensor can measure the distance from a phone-moving surface and an area of a person's body. In an example, this distance sensor can guide the device's movement of a phone over and/or around the person's body. In an example, movement of a phone-moving device can be at least partially controlled by a distance sensor which measures the distance from the device to a portion of a person's body. In an example, a phone-moving device can move a phone around a portion of a person's body in order to capture images at different angles relative to the portion of the body and can move the phone closer to and farther from the portion in order to capture images at different distances relative to the portion.

In an example, a phone-moving device can also have its own optical lens. In an example, this optical lens can be movable. In an example, this optical lens can be automatically moved over (e.g. flipped or slid over) the lens of a camera on an attached phone or other camera-equipped mobile device. In an example, a lens can be flipped down over the phone's camera. In an example, a lens can be slid in front of the phone's camera. In an example, a lens can change the focal distance and/or width of images captured by a phone's camera. In an example, a lens can be a magnifying lens. In an example, a lens can include an optical filter. In an example, a phone-moving device can have an electromagnetic motor which automatically moves (e.g. flips or slides) a lens over the camera of a phone which has been attached to the device.

In an example, a phone-moving device can have an optical lens which can be remotely controlled by a non-local healthcare provider. In an example, after a mobile phone has been attached to the device, a remote operator (such as a remote healthcare provider) can activate a motor which moves a lens over the phone's camera. In an example, a phone-moving device can have an optical lens which can be remotely flipped or pivoted over the lens of an attached phone camera. In an example, a phone-moving device can have a magnifying lens which can be remotely positioned in front of an attached phone camera and controlled by a non-local healthcare provider.

In an example, a phone-moving device can have an audio speaker. In an example, this speaker can convey verbal instructions to the person being scanned, either before or during a scan. In an example, the person can be verbally guided concerning how to position their body (e.g. orientation, distance, and/or configuration) relative to the device, by verbal instructions or non-verbal sounds emitted by the speaker. For example, a person can be guided to position themselves at a proper distance from the device via a sound from the speaker, wherein the sound varies in pitch with varying from the proper distance. In an example, a speaker can emit one or more sounds if the person moves too much during a scan. In an example, a phone-moving device can have a speaker for audio communication between a non-local healthcare provider and the person whose body is being imaged for medical purposes. In an example, a phone-moving device can be in wireless communication with an attached mobile phone and the device speaker can convey speech received via the phone.

In an example, a phone-moving device can have a motion sensor. In an example, this motion sensor can monitor whether a person who is being scanned (imaged) moves too much during the scan. In an example, a phone-moving device can have an infrared motion detector which monitors whether a person moves too much during a scan. In an example, if a person moves too much during a scan, then a device can notify the person. In an example, if a person moves too much during a scan, then a device can end the scan. In an example, if a person moves too much during a scan, then a device can suggest that the scan be restarted and/or redone. In an example, the motion sensor can be located on the base of a phone-moving device so that it is not part of a moving portion of the device during a scan.

In an example, a phone-moving device can be a small-scale flying drone. In an example, a drone can be equipped with a phone-holding mechanism which holds a mobile phone (or other camera-equipped mobile device) which captures images of a portion of a person's body from different angles and/or distances. In an example, a gimbal and/or gyroscopic stabilization mechanism can stabilize an attached mobile phone as the drone flies. In an example, movement of the drone can be remotely controlled, in real time, by a non-local (remote) healthcare provider or by a medical AI program.

In an example, a phone-moving device can be in electromagnetic communication with a mobile phone or other camera-equipped mobile device which is attached to the device. In an example, a phone-moving device can be in electromagnetic communication with a phone which is attached to it. In an example, a phone-moving device can be remotely controlled via a mobile phone application. In an example, a phone-moving device can have a data transmitter and receiver. In an example, a phone-moving device can be in electromagnetic communication with a remote server via the internet.

The following sections describe the embodiments of this invention shown in FIGS. 1 through 50. FIGS. 1 through 4 show an example of a portable phone-moving device which can be part of telemedicine and/or remote medical imaging using a conventional mobile phone or other camera-enabled mobile device. This device comprises; a portable phone-moving device; wherein the phone-moving device further comprises an attachment mechanism which holds a camera-enabled mobile phone (or other camera-enabled mobile device) on the device; and wherein the phone-moving device moves the phone over and/or around a selected portion of a person's body to guide the capturing of phone images of that portion of the person's body from different angles and/or distances for medical purposes.

More specifically, FIGS. 1 through 4 show views at four different times of a portable phone-moving device which can be part of telemedicine and/or remote medical imaging using a conventional mobile phone or other camera-enabled mobile device. These figures also show a conventional mobile phone which is attached to the portable phone-moving device. The phone is not part of the portable phone-moving device itself, although the phone-moving device may be in electromagnetic communication with a phone-based application. Alternatively, a different type of conventional camera-enabled mobile device (such as a camera-enabled tablet device or smart watch) could be attached. The portable phone-moving device helps a person to capture "medical selfie" video or sequential still-frame images of a portion of their body (not shown here) from different angles and/or distances for remote medical evaluation by a non-local (remote) healthcare provider (or a medical AI program). In various examples, medical evaluation of these images may be part of dermatologic evaluation of wounds and/or other skin pathology (e.g. teledermatology), remote cardiovascular evaluation, remote orthopedic evaluation, and/or remote emergency evaluation of an injury.

Medical evaluation of the images can occur in real time as a body portion is being scanned and images are being captured. In an example, a healthcare provider can remotely control, in real time, the angle and/or distance of a phone camera from a body portion via remote control of a portable phone-moving device. In an example, a healthcare provider can also remotely control, in real time, the level, color, and/or spectral distribution of light emitted from the device toward the body portion. In an example, video or sequential still-frame images from scanning the body portion from different angles and/or distances can be combined into a digital three-dimensional image and/or a 3D model of the body portion which a healthcare provider can navigate and evaluate at a later time from different angles and/or distances.

Figure 2:
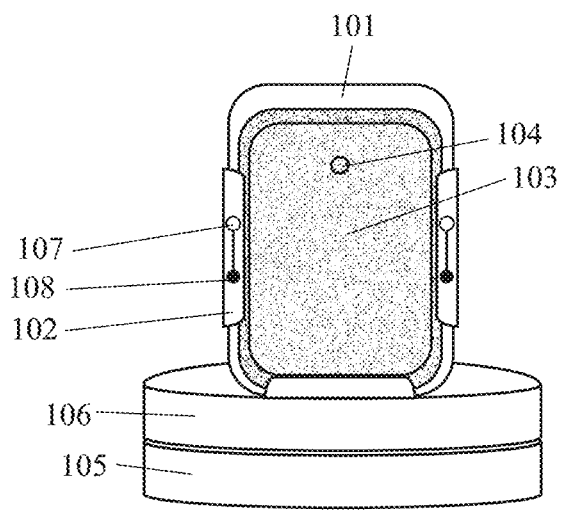

FIG. 1 shows a portable phone-moving device and a nearby camera-equipped mobile phone at a first point in time, before the mobile phone has been attached to the device. Alternatively, a different type of camera-equipped mobile device (such as a tablet device or smart watch) could be used instead of a mobile phone. FIG. 2 shows this device at a second point in time, after the mobile phone has been attached to (e.g. slid into and/or clamped onto) the device.

Figure 3:
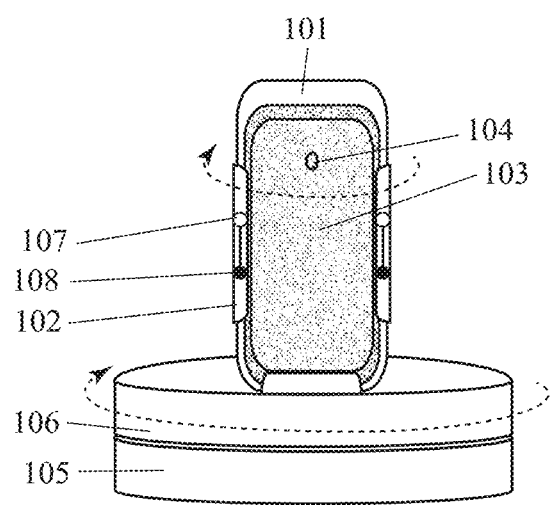

FIG. 3 shows this device at a third point in time, wherein the device is automatically rotated (e.g. rotated, revolved, and/or pivoted), thereby changing the focal direction of the mobile phone's camera. As the device moves, the camera captures images of a nearby body portion (not shown here) from different angles and/or distances. In an example, these images taken from different angles and/or distances can be combined to create a digital three-dimensional image for medical evaluation purposes. Movement of the device can be remotely controlled, in real time, by a healthcare provider (or a medical AI program) for medical imaging and evaluation purposes. By controlling the device remotely, a healthcare provider can scan a portion of the person's body from different angles and zoom in or out from different distances.

Figure 4:
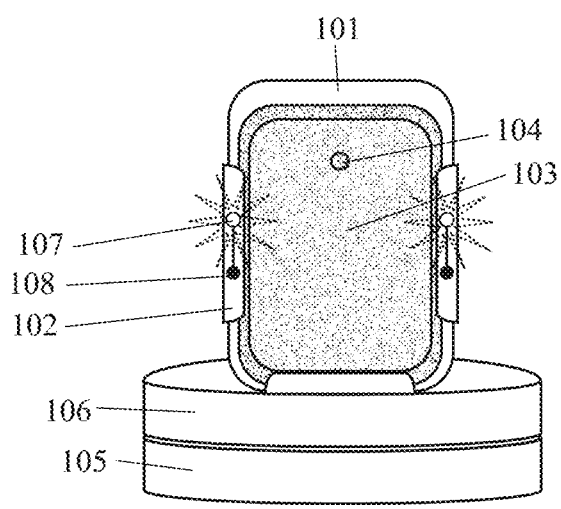

FIG. 4 shows this device at a fourth point in time wherein light emitters (e.g. LEDs) on the device have been activated to emit light toward the body portion. In an example, a remote healthcare provider (or medical AI program) can control the level, color, and/or spectral distribution of light emitted from the device toward the body portion.

With respect to specific components, FIGS. 1 through 4 show a portable phone-moving device which helps to capture phone images (e.g. "medical selfies") of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 101 onto which the phone is attached and a clip, clasp, clamp, hook, strap, or magnet 102 which holds the phone against the phone-supporting surface; wherein the phone-moving device further comprises an upper base 106 below the phone-supporting surface and a lower base 105 below the upper base, and wherein the upper base rotates, revolves, and/or pivots relative to the lower base, thereby rotating, revolving, and/or pivoting the phone.

The example device shown in FIGS. 1 through 4 further comprises one or more light emitters (including light emitter 107) and one or more light receivers or sensors (including light receiver or sensor 108). In an example, light emitters illuminate a nearby body portion being scanned (imaged) by the mobile phone. In an example, the level, color, and/or spectral distribution of light emitted from the one or more light emitters on the device can be varied automatically during a scan of a body portion. In an example, the level, color, and/or spectral distribution of light emitted from one or more light emitters on the device can be remotely controlled by a non-local (remote) healthcare provider (or a medical AI program). FIGS. 1 through 4 also show a conventional mobile phone 103 equipped with a camera 104 which is attached to the device, although the phone is not part of the device itself.

In an example, an attachment mechanism which attaches a conventional phone to the device can include one or more components selected from the group consisting of: a clip, a clasp, a clamp, a snap, a hook, a prong, a track, a strap, a band, a pocket, a magnet, and hook-and-eye fabric. In an example, an attachment mechanism can include two such components, one which attaches the right side of a phone and one which attaches the left side of the phone. In an example, an attachment mechanism can include three such components, which attach three sides of a phone to the device. In an example, a conventional camera-equipped mobile phone can be used with this portable phone-moving device. In an example, this device can be in electromagnetic communication with software, such as a mobile application, on a conventional mobile phone. In an example, this device can be remotely controlled by a non-local (remote) healthcare provider (or a medical AI program) via a mobile phone application.

In an example, a portable phone-moving device can have a rotating (e.g. rotating, revolving, and/or pivoting) base which moves a mobile phone as the base rotates, revolves, and/or pivots. In an example, a portable phone-moving device can have an electromagnetic motor which rotates, revolves, and/or pivots the base. In an example, rotation, revolution, and/or pivoting of a device can be remotely controlled by a non-local (remote) healthcare provider (or a medical AI program). In an example, a phone-moving device can have a two-part base, wherein an upper part of the base rotates and/or pivots relative to a lower part of the base. In an example, upper and/or lower parts of a device base can be circular. In an example, a portable phone-moving device can further comprise wheels and/or treads which move the device relative to the body portion.

In an example, a portable phone-moving device can have one or more light emitters (such as LEDs) whose light illuminates a body portion being scanned. In an example, a light emitter can emit visible broad-spectrum light. In an example, a light emitter can emit near-infrared light. In an example, the intensity, wavelength, color, and/or spectral distribution of light emitted by the device can vary automatically during a scan of a body portion. In an example, the spectral distribution (e.g. wavelengths) of light emitted from the device toward a portion of a person's body can be automatically varied to image body tissue with light with different colors and/or spectral distributions. In an example, the intensity, wavelength, color, and/or spectral distribution of light emitted by the device can be remotely controlled, in real time, by a non-local (remote) healthcare provider (or a medical AI program).

In an example, a portable phone-moving device can project light, such as coherent light, with a known wavelength into the field of view of a camera and this light can be used to calibrate the colors of images received by the camera. This can help to control for variation in color calibration of images from different types and brands of conventional mobile phones, without the need for a physical color marker in the camera's field of view. In an example, a device can project a light pattern of coherent light onto the body portion and/or a nearby surface, wherein the size and/or shape of the projected pattern is used as a fiducial marker to estimate the angle and/or distance to the body portion. In an example, a portable phone-moving device can also have a light receiver and/or light sensor which receives light which has been reflected from the body portion. In an example, changes in the spectral distribution of light caused by reflection from the body portion can be used to analyze tissue molecular composition and/or tissue health.

In an example, a portable phone-moving device can be placed near (e.g. between 3 inches and 3 feet from) a body portion and can scan (e.g. capture multiple images from different angles and/or distances) the body portion by rotating, revolving, and/or pivoting a phone. In an example, a device can rotate, revolve, and/or pivot a phone in one or more complete (360-degree) circles. In an example, a device can rotate, revolve, and/or pivot a phone less than 360 degrees. In an example, a device can rotate, revolve, and/or pivot a phone between 20 and 180 degrees. In an example, a device can oscillate a phone back and forth (e.g. clockwise and counter-clockwise). In an example, a device can pivot a phone up and down as well as rotate the phone clockwise and counter-clockwise. In an example, a non-local (remote) healthcare provider (or a medical AI program) can remotely control the rotation and/or pivoting of a phone via a phone-based or internet-based application.

In an example, a portable phone-moving device can also include a motion sensor. In an example, a phone-moving device can instruct a person to remain still during scanning (imaging). If motion of the person is detected by the motion sensor during scanning, then the device can notify the person. In an example, if motion of the person is detected, then the device can automatically notify the person, end the scan, and suggest that the scan be restarted. In an example, the device may give verbal instructions to the person via the phone's speaker via electromagnetic communication with the phone. Alternatively, a device can have its own speaker and give verbal instructions to the person via that speaker. In an example, these instructions may be automated. In an example, a non-local (remote) healthcare provider (or a medical AI program) may give these instructions in real time via a phone speaker or a device speaker. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 5:
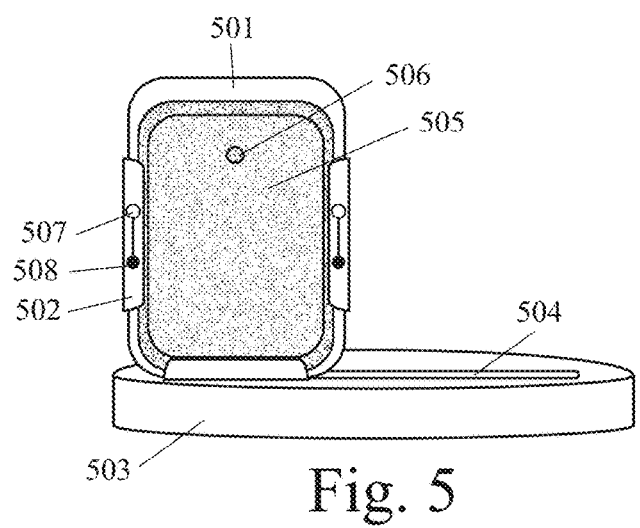
FIGS. 5 and 6 show a phone-moving device which slides an attached mobile phone horizontally for medical imaging.
Figure 6:
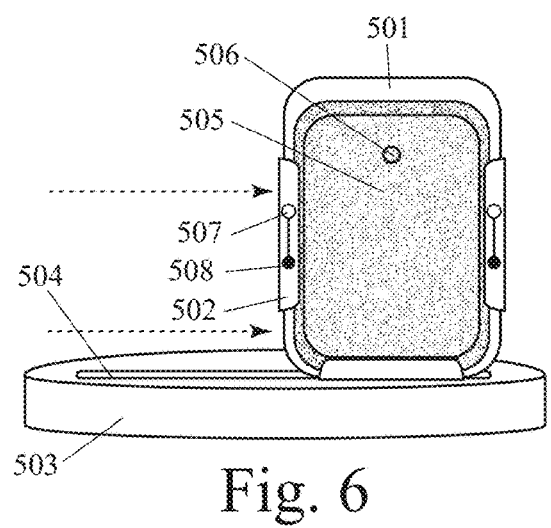

FIGS. 5 and 6 show another example of a portable phone-moving device which can be part of telemedicine and/or remote medical imaging using a conventional mobile phone or other camera-enabled mobile device. This device comprises; a portable phone-moving device; wherein the phone-moving device further comprises an attachment mechanism which holds a camera-enabled mobile phone (or other camera-enabled mobile device) on the device; and wherein the phone-moving device moves the phone over and/or around a selected portion of a person's body (not shown here) to guide the capturing of phone images ("medical selfies") of that portion from different angles and/or distances for medical purposes.

More specifically, FIGS. 5 and 6 show views at two different times of a portable phone-moving device which can be part of telemedicine and/or remote medical imaging using a conventional mobile phone or other camera-enabled mobile device. These figures also show a conventional mobile phone which is attached to the portable phone-moving device. This phone is not part of the portable phone-moving device itself, although the phone-moving device may be in electromagnetic communication with a phone-based application. FIG. 5 shows the portable phone-moving device at a first point in time, wherein the device holds a mobile phone at a first location along (e.g. at a first end of) a horizontal track on the device. FIG. 6 shows the portable phone-moving device at a second point in time, wherein the device has moved the mobile phone to a second location along (e.g. at a second end of) the horizontal track. Movement of the phone along the horizontal track changes the angle and/or distance from the phone to the portion of the person's body which is being scanned (imaged). In an example, the phone can also be pivoted around its longitudinal axis to maintain focus toward the same area of the body portion as it is moved horizontally.

With respect to specific components, FIGS. 5 and 6 show a portable phone-moving device which helps to capture phone images (e.g. "medical selfies") of a portion of a person's body for medical purposes comprising: a portable phone-moving device; wherein the phone-moving device further comprises an attachment mechanism which holds a camera-enabled mobile phone (or other camera-enabled mobile device) to the device; wherein the attachment mechanism further comprises a phone-supporting surface 501 onto which the phone is attached and at least one clip, clasp, clamp, hook, strap, or magnet 502 which holds the phone on or in the phone-supporting surface; wherein the phone-moving device further comprises a base 503 below the phone-supporting surface; and a track 504 on the base along which the phone-supporting member is moved. The example device shown in FIGS. 5 and 6 further comprises one or more light emitters (including light emitter 507) and one or more light receivers or sensors (including light receiver or sensor 508). FIGS. 5 through 6 also show a conventional mobile phone 505 equipped with a camera 506 which is attached to the device, although the phone is not part of the device itself.

In an example, there can be a track along a portable phone-moving device along which a phone-supporting surface is moved. In an example, this track can be along the upper surface of a base of this device. In an example, this track can have a straight-line shape. In an example, this track can be arcuate. In an example, the shape of such a track can be a conic section. In an example, this track can be substantially horizontal. In an example, this track can be substantially vertical. In an example, this track can span three-dimensional space in both horizontal and vertical dimensions. In an example, a phone-supporting surface can be moved back and forth along a track during a scan of a body portion. In an example, a phone-supporting surface can be moved along a track by a gear mechanism. In an example, a phone-supporting surface can be moved along a track by a chain-link mechanism. In an example, a phone-supporting surface can be moved along a track by a cable mechanism. In an example, a phone-supporting mechanism can be moved along a track by an electromagnetic motor. In an example, movement of a phone along this track can be remotely controlled by a non-local (remote) healthcare provider (or a medical AI program).

In an example, this device can have a base with an oblong, oval, or elliptical shape. In an example, the base of this device can have a rectangular shape. In an example, the base of this device can have a circular shape. In an example, there can be motorized wheels or moving treads on the base which enable automated movement of the entire device. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 7:
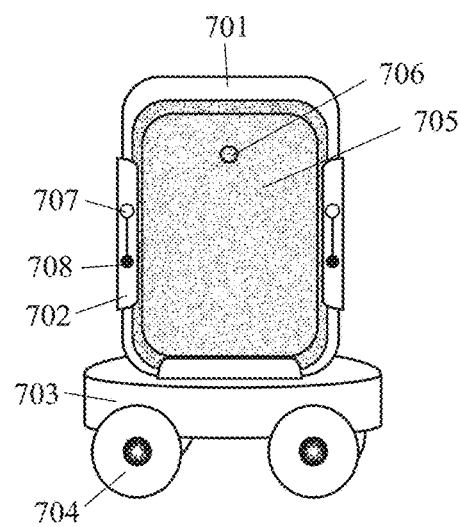
FIGS. 7 and 8 show a rolling phone-moving device which moves an attached mobile phone for medical imaging.
Figure 8:
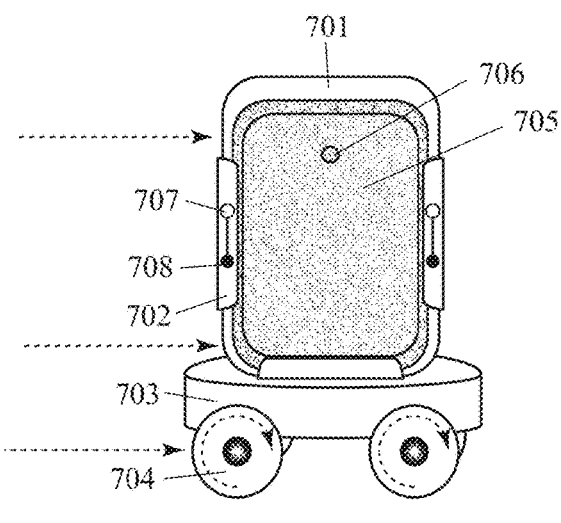

FIGS. 7 and 8 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body (not shown here) to guide the capturing of phone images of that portion from different angles and/or distances for medical purposes. In this example, the base of the device is on motorized wheels so that the entire device can move automatically relative to the portion of the person's body. In an example, this movement can be remotely-controlled by a healthcare provider (or a medical AI program).

FIGS. 7 and 8 show two views, at two different times, of the portable phone-moving device. FIG. 7 shows the portable phone-moving device at a first location before the device has been rolled by its wheels. FIG. 8 shows the portable phone-moving device at a second location after the device has been rolled by its wheels. This movement changes the angle and/or distance from the phone to the portion of the person's body which is being scanned (imaged). In an example, the phone can also be pivoted around its longitudinal axis to maintain focus toward the same area of the body portion as it rolls along.

With respect to specific components, FIGS. 7 and 8 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 701 onto which the phone is attached and at least one clip, clasp, clamp, hook, strap, or magnet 702 which holds the phone on or in the phone-supporting surface; a base 703; and at least one wheel 704. The example device shown in FIGS. 7 and 8 further comprises one or more light emitters (including light emitter 707) and one or more light receivers or sensors (including light receiver or sensor 708). FIGS. 7 and 8 also show a conventional mobile phone 705 equipped with a camera 706 which is attached to the device, although the phone is not part of the device itself.

In an example, a portable phone-moving device can have four wheels. In an example, this device can have two wheels on a fixed axle and two wheels on a steerable axle. In an example, this device can have six wheels. In an example, one or more wheels can be rotated independently of each other, enabling the device to rotate via wheel movement as well as move sideways via wheel movement. In an example, this device can have moving treads instead or, or in addition to, wheels. In an example, wheels and/or treads can be rotated by an electromagnetic motor. In an example, movement of the device via wheel or tread movement can be remotely-controlled by a non-local (remote) healthcare provider (or a medical AI program). In an example, this device can further comprise a distance sensor (e.g. infrared light distance sensor) which guides movement of the device around a person's body and/or other objects in the environment. In an example, this device can further comprise one or more components selected from the group consisting of: electromagnetic motor; battery; data processor; wireless data transmitter; and wireless data receiver. Relevant example variations discussed elsewhere in this and priority-linked disclosures can be also applied to this example.

Figure 9:
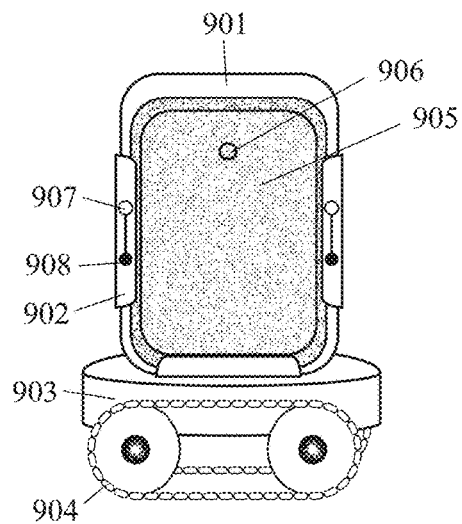
FIGS. 9 and 10 show a phone-moving device which moves on caterpillar treads to move an attached mobile phone for medical imaging.
Figure 10:
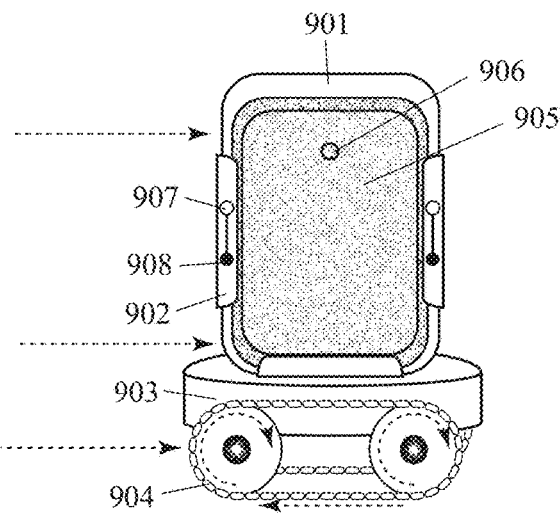

FIGS. 9 and 10 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body (not shown here) to guide the capturing of phone images of that portion from different angles and/or distances for medical purposes. In this example, the device has motorized moving (caterpillar) treads so that the entire device can move automatically. FIGS. 9 and 10 show views of the device at different times. FIG. 9 shows the portable phone-moving device at a first location, before the device has been moved by its treads. FIG. 10 shows the portable phone-moving device at a second location, after the device has been moved by its treads.

With respect to specific components, FIGS. 9 and 10 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 901 onto which the phone is attached and at least one clip, clasp, clamp, hook, strap, or magnet 902 which holds the phone on or in the phone-supporting surface; a base 903; and at least one motorized moving tread 904. The example device shown in FIGS. 9 and 10 further comprises one or more light emitters (including light emitter 907) and one or more light receivers or sensors (including light receiver or sensor 908). FIGS. 9 and 10 also show a conventional mobile phone 905 equipped with a camera 906 which is attached to the device, although the phone is not part of the device itself.

In an example, a portable phone-moving device can have two moving caterpillar treads, like construction equipment or a tank. In an example, the treads can be moved independently of each other, enabling the device to rotate as well as move forward or backwards. In an example, treads can be moved by an electromagnetic motor. In an example, this device can further comprise a distance sensor (e.g. infrared light distance sensor) which guides movement of the device around a person's body and/or other objects in the environment. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 11:
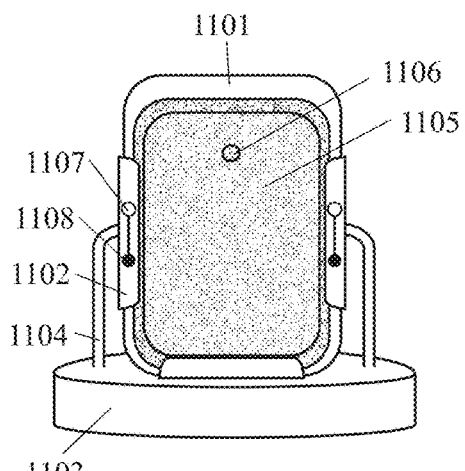
FIGS. 11 and 12 show a phone-moving device which tilts an attached mobile phone around the phone's horizontal axis for medical imaging.
Figure 12:
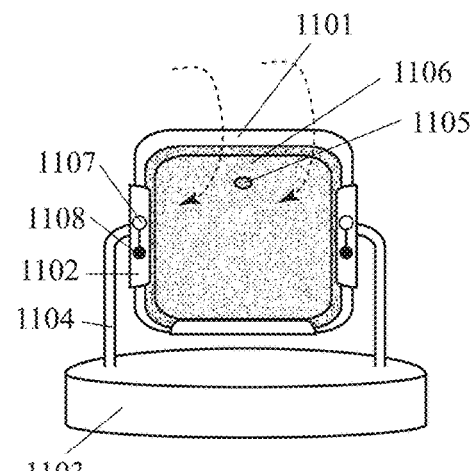

FIGS. 11 and 12 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body (not shown here) to guide the capturing of phone images of that portion from different angles and/or distances for medical purposes. In this example, the device automatically rotates and/or pivots a mobile phone around the phone's horizontal and/or lateral axis. FIG. 11 shows the device before the phone has been rotated and/or pivoted by the device. FIG. 12 shows the device after the phone has been rotated and/or pivoted by the device. In an example, the phone is rotated and/or pivoted around its horizontal and/or lateral axis by an electromagnetic motor in the device.

With respect to specific components, FIGS. 11 and 12 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 1101 onto which the phone is attached and at least one clip, clasp, clamp, hook, strap, or magnet 1102 which holds the phone on or in the phone-supporting surface; a base 1103; and an axle 1104 to which the phone-supporting member is attached, wherein rotation and/or pivoting of the phone-supporting member around the axle causes the phone to rotate and/or pivot around a horizontal and/or lateral axis. The example device shown in FIGS. 11 and 12 further comprises one or more light emitters (including light emitter 1107) and one or more light receivers or sensors (including light receiver or sensor 1108). FIGS. 11 and 12 also show a conventional mobile phone 1105 equipped with a camera 1106 which is attached to the device, although the phone is not part of the device itself.

In an example, a phone-supporting surface of this device can be rotated and/or pivoted around a horizontal axle by a gear mechanism. In an example, a phone-supporting surface of this device can be rotated and/or pivoted around a horizontal axle by an electromagnetic mechanism. In an example, a phone-supporting surface of this device can be rotated and/or pivoted around a horizontal axle by an electromagnetic motor. In an example, the device can also rotate (e.g. via a rotating base). In an example, the device can also move sideways (e.g. via wheels or treads). In an example, the device can also move up and down (e.g. via a telescoping base). In an example, the device can further comprise a distance sensor (e.g. infrared light distance sensor) which guides movement of the device around a person's body and/or other objects in the environment. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 13:
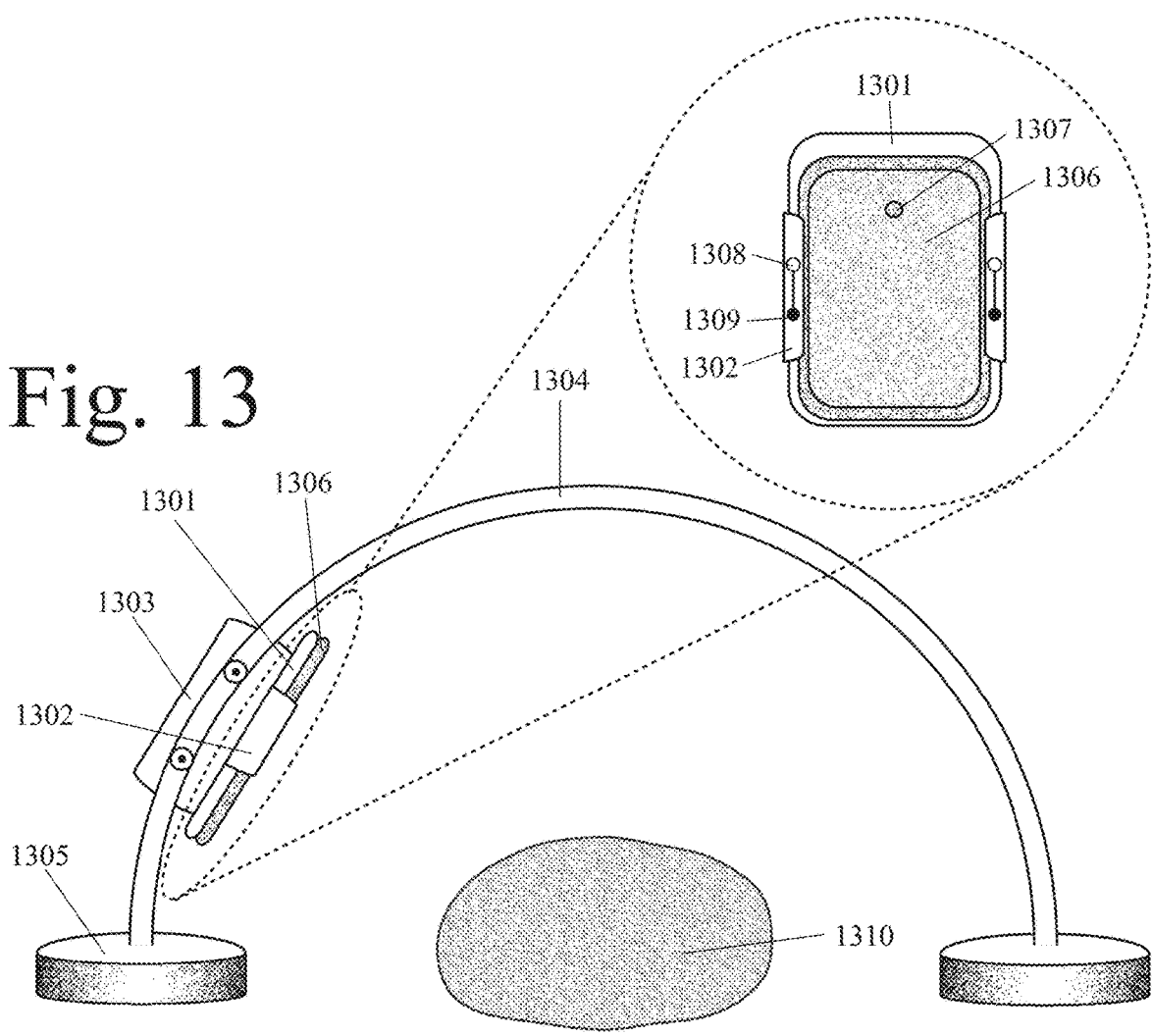
FIGS. 13 and 14 show a phone-moving device with a semicircular track along which an attached mobile phone is moved over a person's body.
Figure 14:
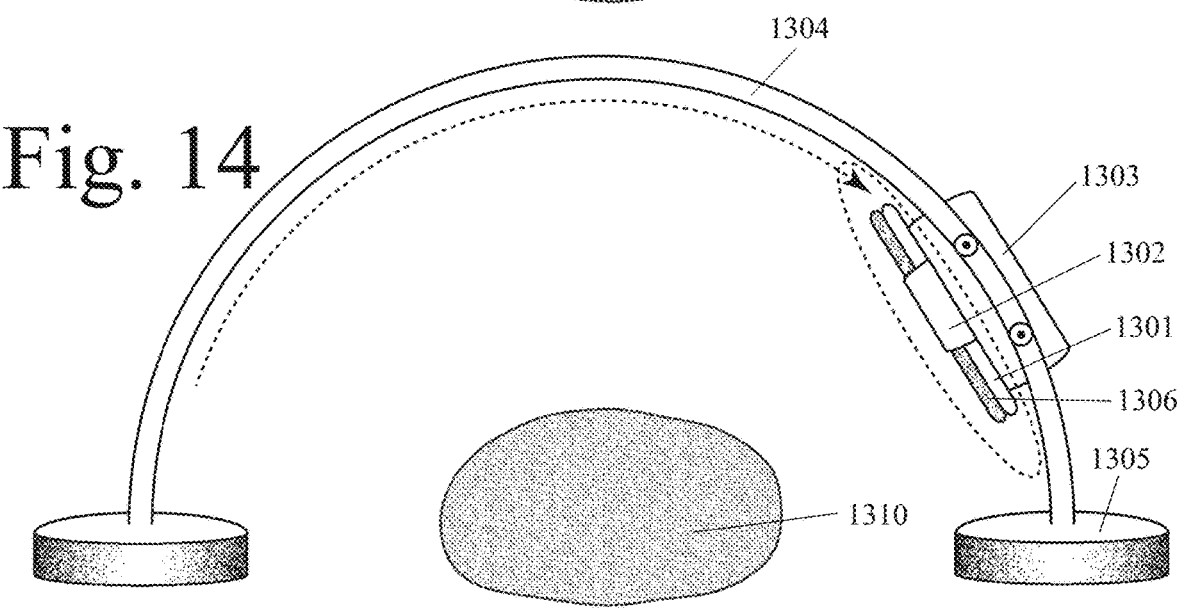

FIGS. 13 and 14 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body to guide the capturing of phone images of that portion from different angles and/or distances for medical purposes. In this example, the device includes an arcuate (e.g. rib or arch shaped) track along which a mobile phone is moved over a portion of a person's body. FIG. 13 shows the device with the phone located at a first location along an arcuate track. FIG. 14 shows the device with the phone having been automatically moved to a second location along the arcuate track.

With respect to specific components, FIGS. 13 and 14 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 1301 onto which the phone is attached and at least one clip, clasp, clamp, hook, strap, or magnet 1302 which holds the phone on or in the phone-supporting surface; an arcuate (e.g. rib or arch shaped) track 1304, wherein the phone-supporting surface is moved by the device along the arcuate track; at least one base 1305 which holds the arcuate track upright; and a connector 1303 which connects the phone-supporting surface to the arcuate track. Alternatively, a phone-supporting surface can be directly connected to the arcuate track without the need for an intermediate connector. The upper-right portion of FIG. 13 shows a close-up frontal view of the phone and the phone-supporting surface, within a dotted-line circle, corresponding to a side-view perspective of this structure, within a dotted-line ellipse, in the lower portion of FIG. 13.

The example device shown in FIGS. 13 and 14 further comprises one or more light emitters (including light emitter 1308) and one or more light receivers or sensors (including light receiver or sensor 1309). FIGS. 13 and 14 also show: a conventional mobile phone 1306 equipped with a camera 1307 which is attached to the device; and a cross-section 1310 of a portion of the person's body being imaged. Neither the phone nor the person's body are positively claimed as part of the device.

In an example, an arcuate track along which a phone is moved can be rib or arch shaped. In an example, an arcuate track can be semi-circular. In an example, an arcuate track can have a conic section shape. In an example, an arcuate track can be concave, wherein a portion of a person's body which is scanned (imaged) is located within the concavity of the track. In an example, the length and/or span of an arcuate track along which a phone is moved can be adjusted to accommodate different size portions of a person's body. For example, the length and/or span of an arcuate track can be decreased for scanning a hand or arm, but increased for scanning a torso. In an example, an arcuate track can have one or more telescoping components which can be shortened or lengthened to decrease or increase, respectively, the length and/or span of the track. In an example, the length and/or span of the arcuate track can be adjusted within a range of 3 inches to 3 feet.

In an example, a connector and/or a phone-supporting surface (and thereby a phone) can be moved along an arcuate track by an electromagnetic motor. In an example, a connector and/or a phone-supporting surface can be moved along an arcuate track by a gear mechanism. In an example, a connector and/or a phone-supporting surface can be moved along an arcuate track by a chain link mechanism. In an example, a connector and/or a phone-supporting surface can be moved along an arcuate track by a cable mechanism. In an example, a connector and/or a phone-supporting surface can be connected to an arcuate track at two points, which enables the connector and/or phone-supporting surface to rotate without binding as it moves along the arcuate track. In an example, the arcuate track can be collapsed (e.g. telescoped in, folded, or detached) for storage and extended (e.g. telescoped out, unfolded, or assembled) for use. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 15:
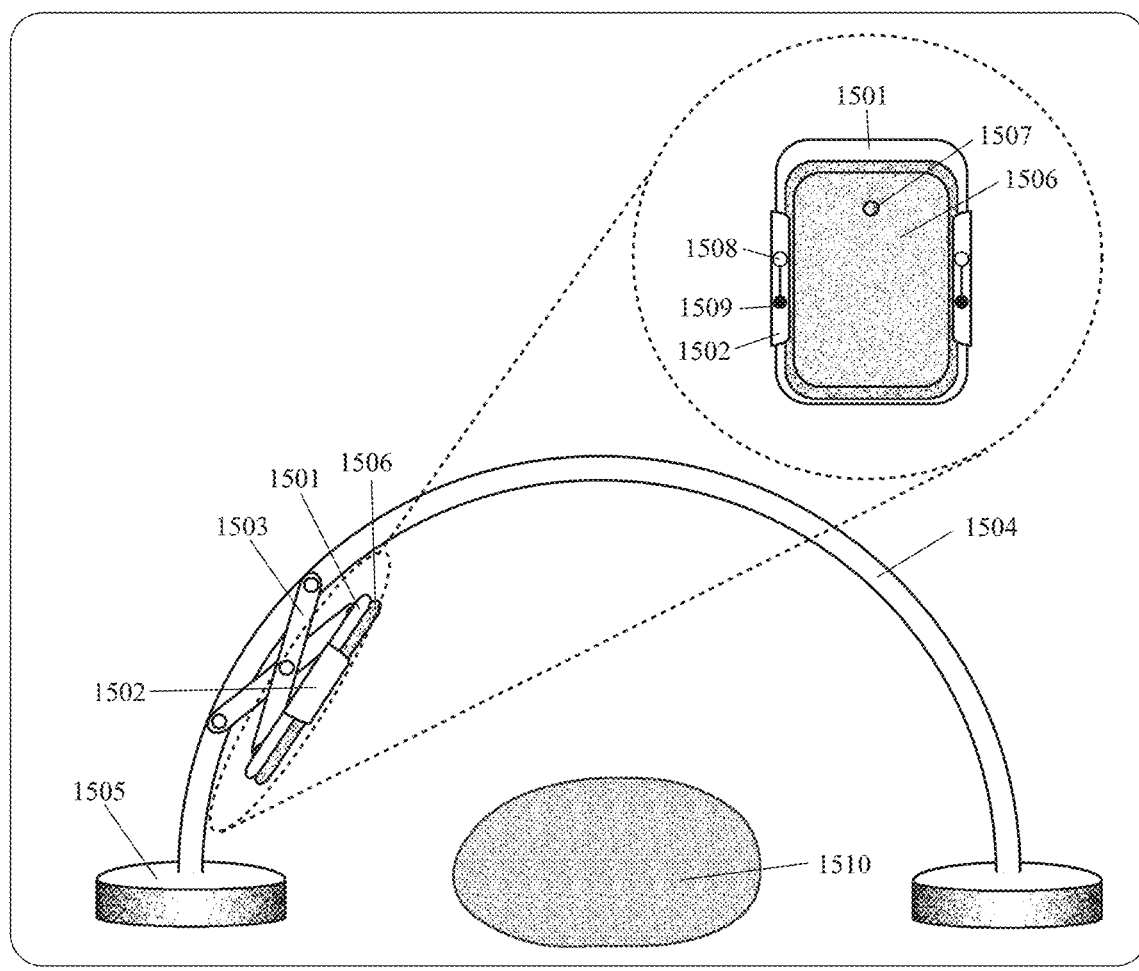
FIGS. 15 and 16 show a phone-moving device with a semicircular track and an extension mechanism which changes the distance from an attached mobile phone and a person's body.
Figure 16:
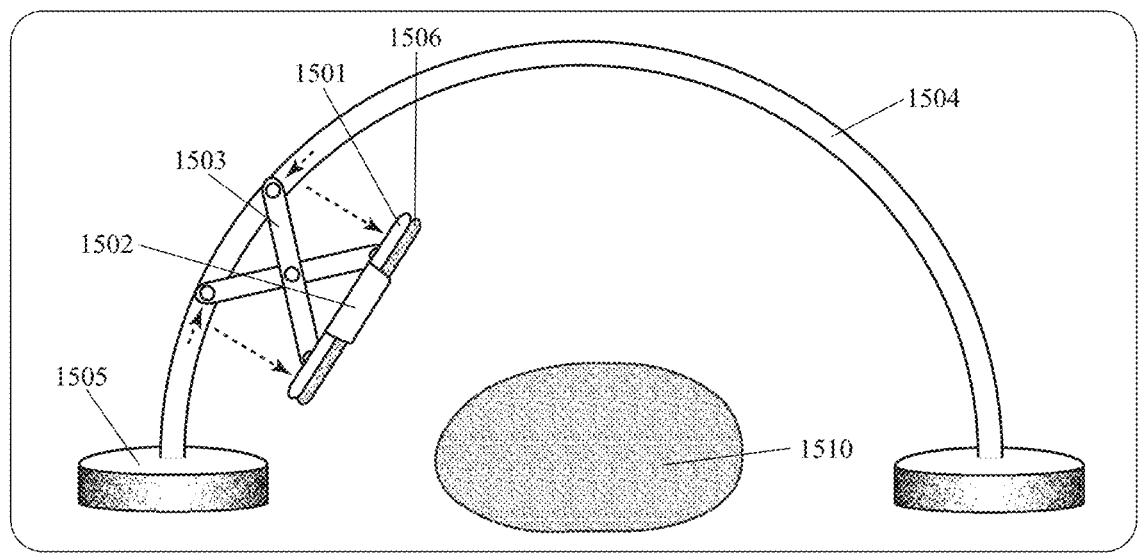

FIGS. 15 and 16 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body to guide the capturing of phone images of that portion from different angles and/or distances for medical purposes. In this example, the device includes an extension mechanism which automatically changes the distance of a phone from a person's body. FIG. 15 shows the device with the phone at a first distance from a person's body. FIG. 16 shows the device with the phone having been automatically moved to second (shorter) distance from the person's body.

With respect to specific components, FIGS. 15 and 16 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 1501 onto which the phone is attached and at least one clip, clasp, clamp, hook, strap, or magnet 1502 which holds the phone on or in the phone-supporting surface; an arcuate (e.g. rib or arch shaped) track 1504; at least one base 1505 which holds the arcuate track upright; and an extension mechanism 1503 which changes the distance of the phone-supporting surface from the arcuate track (thereby also changing the distance from the phone to the person's body). The upper-right portion of FIG. 15 shows a close-up frontal view of the phone and the phone-supporting surface (within a dotted-line circle) corresponding to the side-view perspective of this same structure (within a dotted-line ellipse) in the lower portion of FIG. 15.

The example device shown in FIGS. 15 and 16 further comprises one or more light emitters (including light emitter 1508) and one or more light receivers or sensors (including light receiver or sensor 1509). FIGS. 15 and 16 also show: a conventional mobile phone 1506 equipped with a camera 1507 which is attached to the device; and a cross-section 1510 of a portion of the person's body being scanned (imaged). Neither the phone nor the person's body are positively claimed as part of the device.

As shown in FIGS. 15 and 16, an extension mechanism which changes the distance of a phone from a person's body can comprise one or more scissor and/or "X-shaped" segments. In an example, an extension mechanism can be selected from the group consisting of: one or more scissor or "X-shaped" segments; a rotating threaded mechanism; an electromagnetically-actuated hinge or lever; a folding/unfolding mechanism, and a telescoping and/or piston mechanism. In an example, a phone-supporting surface can be selectively moved along an arcuate track and moved inward-or-outward relative to the arcuate track, thereby enabling scanning (imaging) a body portion from different angles and different distances. In an example, both of these movements can be independently controlled by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 17:
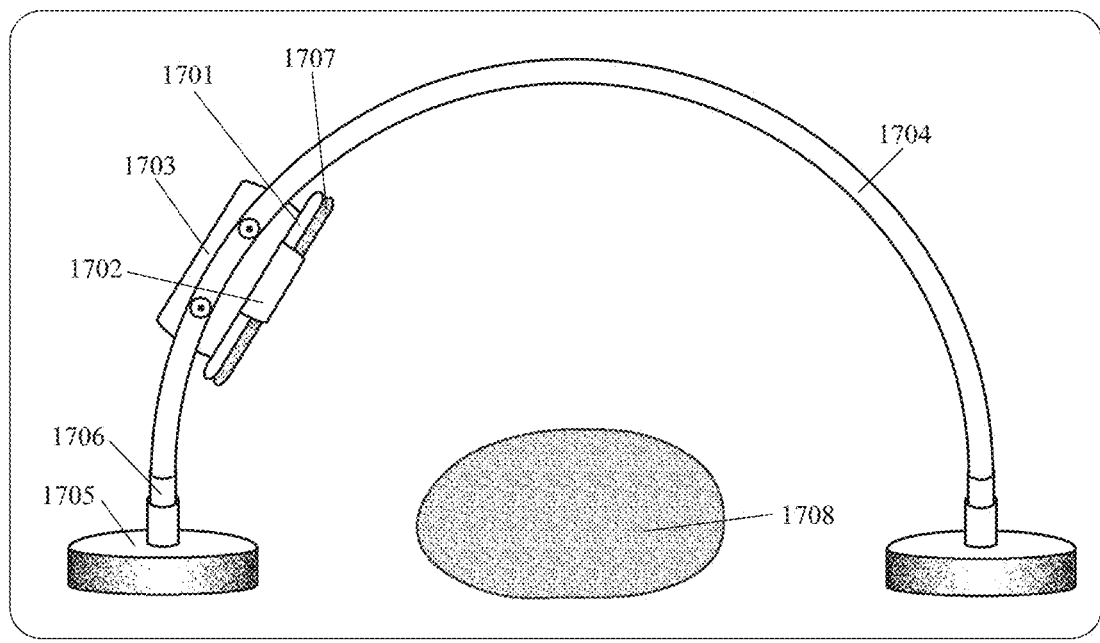
FIGS. 17 and 18 show a phone-moving device to guide medical imaging with a semicircular track and telescoping vertical supports.
Figure 18:
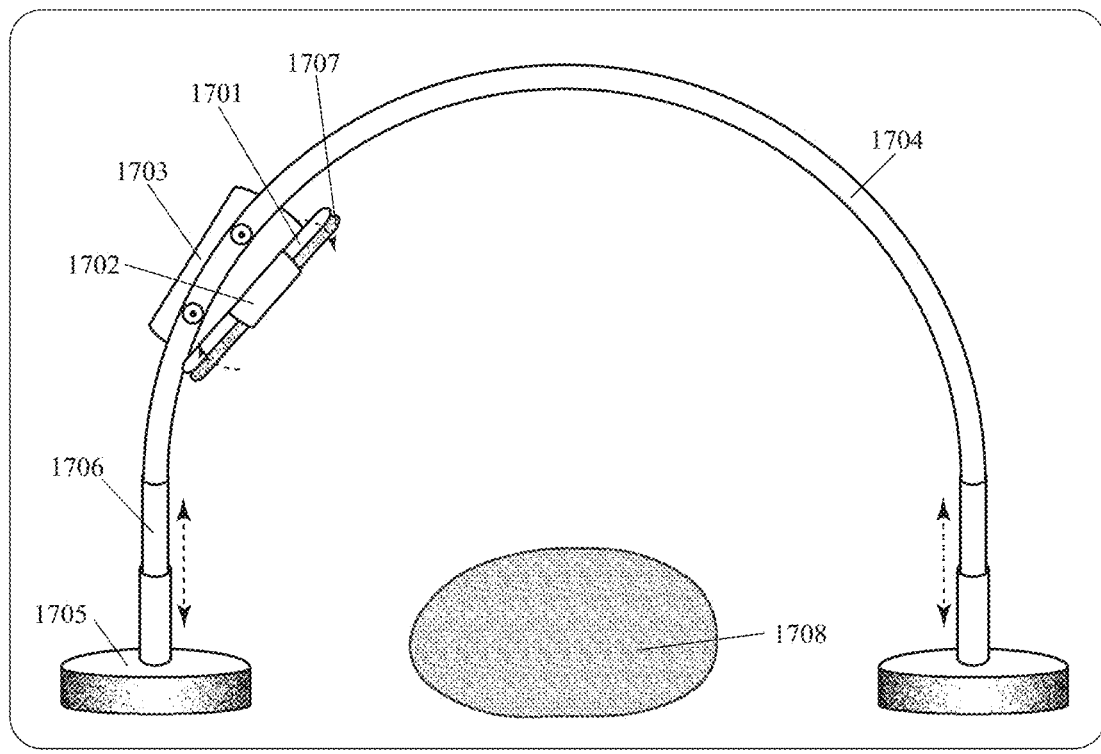

FIGS. 17 and 18 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body to guide the capturing of phone images of that portion from different angles and/or distances for medical purposes. FIG. 17 shows the device with the phone at a first angle relative to an arcuate track (and a person's body). FIG. 18 shows the device with the phone having been automatically rotated and/or pivoted by the device to a second angle relative to the arcuate track (and the person's body).

With respect to specific components, FIGS. 17 and 18 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 1701 onto which a phone is attached and at least one clip, clasp, clamp, hook, strap, or magnet 1702 which holds the phone on or in the phone-supporting surface; an arcuate (e.g. rib or arch shaped) track 1704; at least one base 1705 which holds the arcuate track upright; at least one telescoping mechanism 1706 which adjusts the height of the arcuate track; and a rotating and/or pivoting mechanism 1703 which rotates and/or pivots the phone-supporting surface (and thus also the phone) relative to the arcuate track. FIGS. 17 and 18 also show: a conventional mobile phone 1707 which is attached to the device; and a cross-section 1708 of a portion of the person's body being scanned (imaged). Neither the phone nor the person's body are positively claimed as part of the device.

In an example, a rotating and/or pivoting mechanism can be selected from the group consisting of: one or more scissor or "X-shaped" segments; a rotating threaded mechanism; an electromagnetically-actuated hinge or lever; a rotating disk; and a telescoping and/or piston mechanism. In an example, a phone-supporting surface can be selectively moved along an arcuate track and rotated (or pivoted) relative to the arcuate track, thereby enabling scanning (imaging) a body portion from different angles and different distances. In an example, the height of the arcuate track can be adjusted by decreasing or increasing the height of the telescoping mechanism shown in FIGS. 17 and 18. In an example, all of these device movements can be independently controlled, in real time, by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 19:
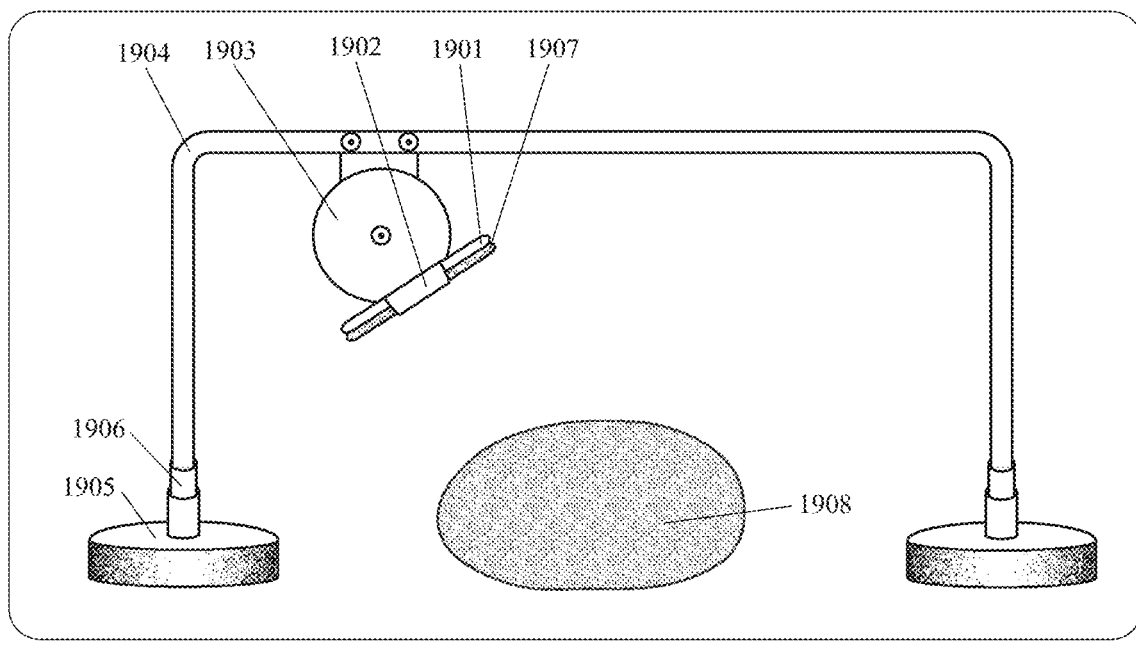
FIGS. 19 and 20 show a phone-moving device to guide medical imaging which is shaped like a soccer net frame.
Figure 20:
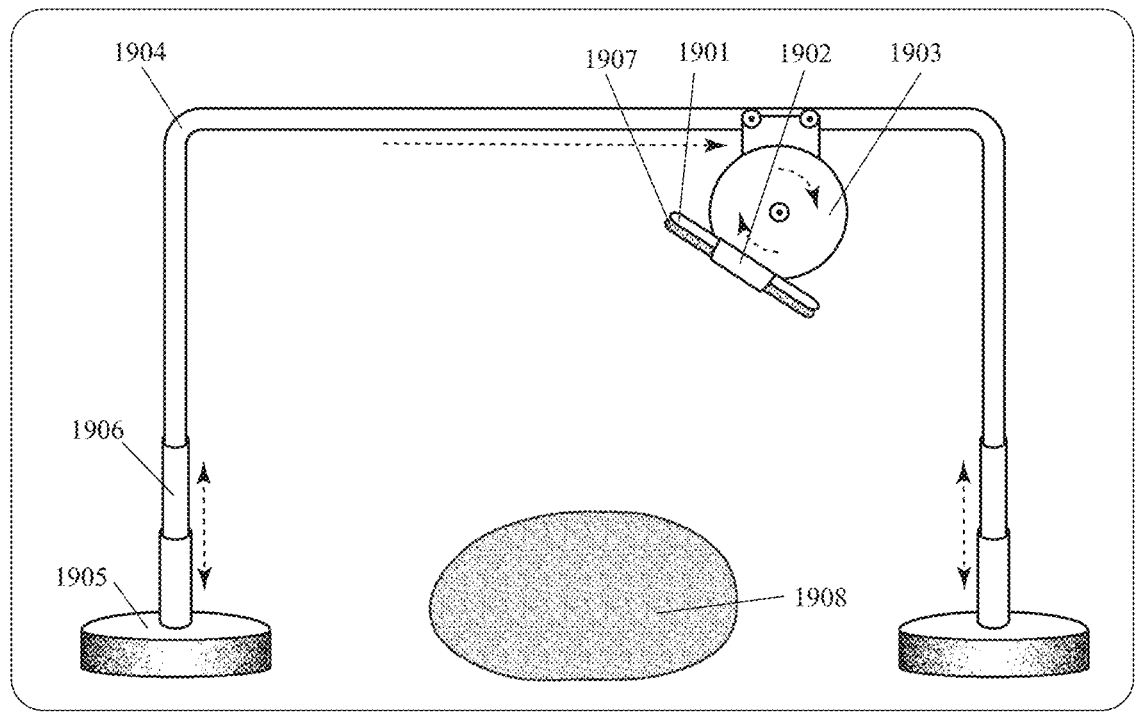

FIGS. 19 and 20 show another example of a portable phone-moving device comprising: a portable phone-moving device; wherein the phone-moving device further comprises an attachment mechanism which holds a camera-enabled mobile phone to the device; and wherein the phone-moving device moves the phone over and/or around a selected portion of a person's body to guide the capturing of phone images of that portion from different angles and/or distances for medical purposes. In this example, the device includes a pivoting mechanism which automatically changes the angle of a phone relative to a track and/or a person's body. FIG. 19 shows the device with the phone at a first location and at a first angle relative to a track which spans the space over a portion of a person's body. FIG. 20 shows the device with the phone having been automatically moved and rotated (and/or pivoted) by the device to a second location and at a second angle relative to the track.

With respect to specific components, FIGS. 19 and 20 show a portable phone-moving device which helps to capture phone images of a portion of a person's body for medical purposes comprising: a portable phone-moving device; wherein the phone-moving device further comprises an attachment mechanism which holds a camera-enabled mobile phone (or other camera-enabled mobile device) on the device; wherein the attachment mechanism further comprises a phone-supporting surface 1901 onto which a phone is attached and at least one clip, clasp, clamp, hook, strap, or magnet 1902 which holds the phone on or in the phone-supporting surface; a track 1904 which spans the space over a portion of a person's body; at least one base 1905 which holds the track upright; at least one telescoping mechanism 1906 which adjusts the height of the track; and a moving and rotating mechanism 1903 which moves the phone-supporting surface along the track and also rotates the phone-supporting surface relative to the track. FIGS. 19 and 20 also show: a conventional mobile phone 1907 which is attached to the device; and a cross-section 1908 of a portion of the person's body being scanned (imaged). Neither the phone nor the person's body are positively claimed as part of the device.

As shown in this example, a track over a person can have a "soccer goal frame" shape. In an example, a track over a person can comprise two vertical segments and one horizontal segment between them. In an example, a track over a person can comprise two straight vertical segments and one straight horizontal segment between them. In an example, a moving and rotating mechanism can be selected from the group consisting of: one or more scissor or "X-shaped" segments; a rotating threaded mechanism; an electromagnetically-actuated hinge or lever; a rotating disk; and a telescoping and/or piston mechanism. In an example, a phone-supporting surface can be selectively moved along a track and rotated (or pivoted) relative to the track, thereby enabling scanning (imaging) a body portion from different angles and different distances. In an example, the height of the track can be adjusted by decreasing or increasing the height of the telescoping mechanism shown in FIGS. 19 and 20. In an example, all of these device movements can be independently controlled, in real time, by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 21:
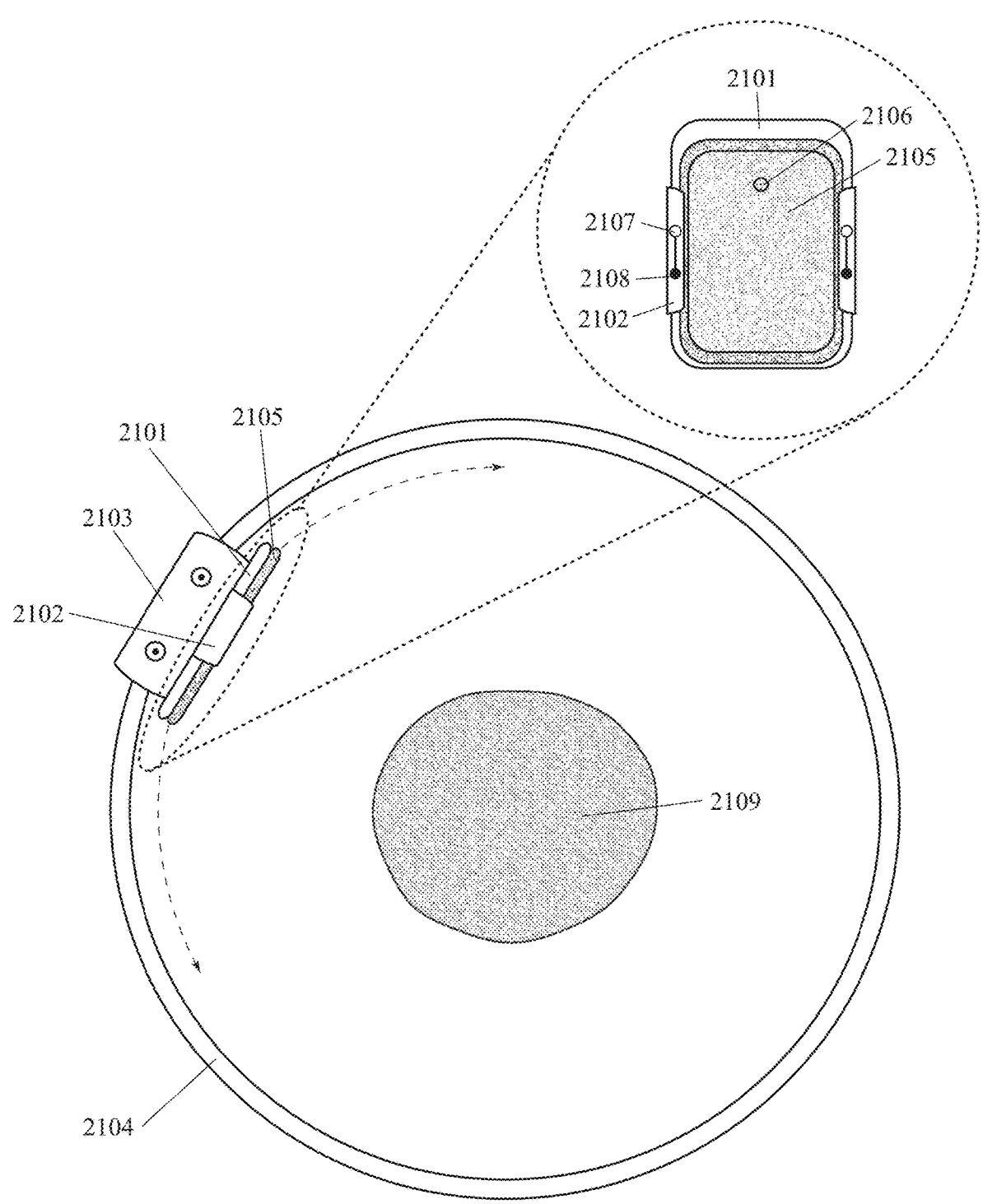
FIG. 21 shows a phone-moving device with a circular track around which an attached mobile phone is moved relative to a person's body for medical imaging.

FIG. 21 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device has a circular track around which the phone is moved to capture images of a portion of the person's body from different angles.

Concerning specific components, FIG. 21 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 2101 onto which the phone is attached and at least one clip, clasp, clamp, hook, strap, or magnet 2102 which holds the phone on the phone-supporting surface; a circular track 2104 around which the phone is moved by the device; and a connector 2103 which connects the phone-supporting surface to the circular track. Alternatively, the phone-supporting surface can be directly connected to the circular track, without the need for an intermediate connector.

The upper-right portion of FIG. 21 shows a close-up frontal view of the phone and the phone-supporting surface (within a dotted-line circle) corresponding to the side-view perspective of this same structure (within a dotted-line ellipse) in the lower portion of FIG. 21. The device in FIG. 21 further comprises one or more light emitters (including light emitter 2107) and one or more light receivers or sensors (including light receiver or sensor 2108). FIG. 21 also shows: a conventional mobile phone 2105 equipped with a camera 2106 which is attached to the device; and a cross-section 2109 of a portion of the person's body which is scanned (imaged). Neither the phone nor the person's body are positively claimed as part of the device.

In an example, a portion of the person's body can be inserted into (or through) the central opening of the circular track. Alternatively, the circular track can be positioned above a portion of a person's body (e.g. above the person's torso, head, leg, or arm) while the person is lying down. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 22:
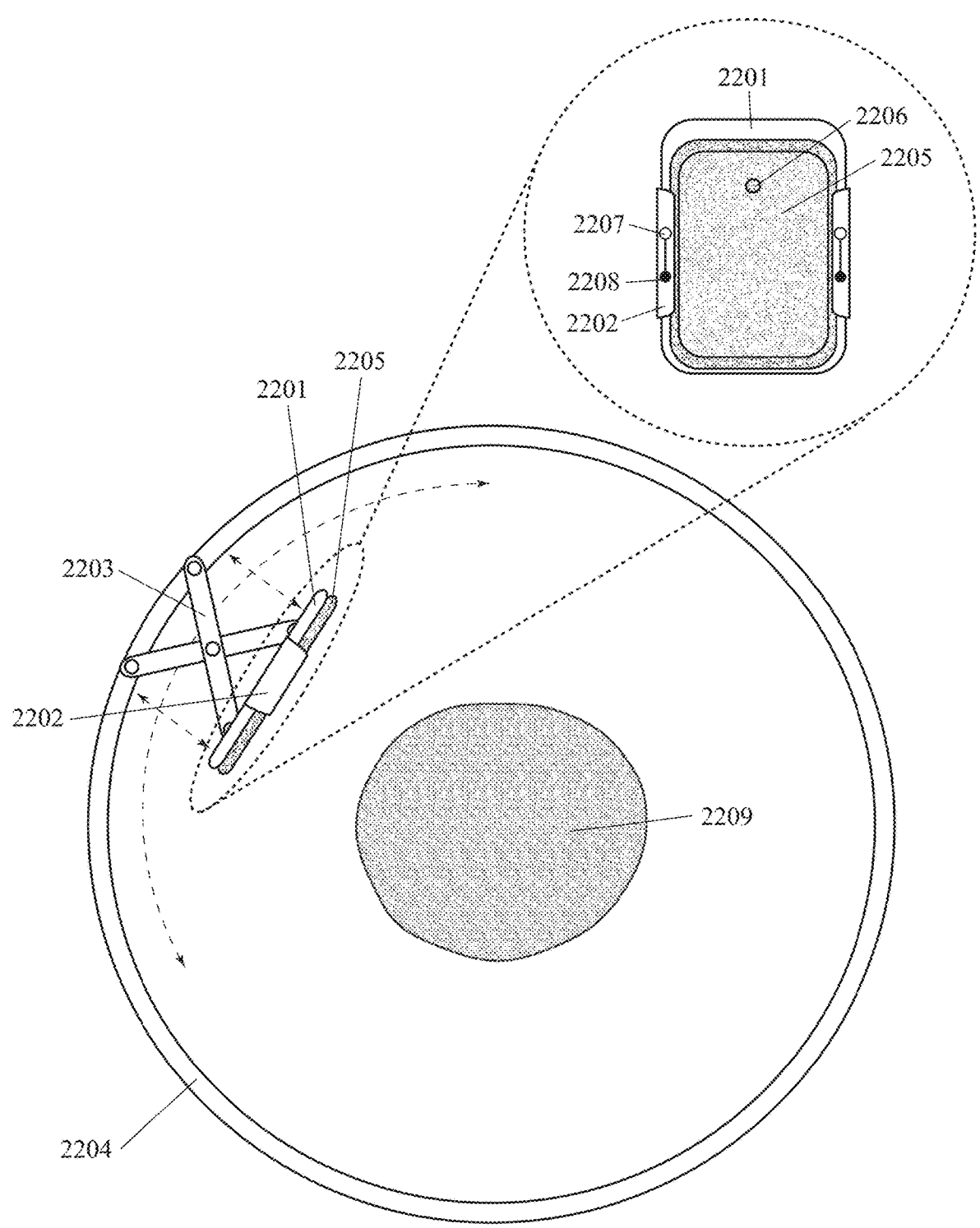
FIG. 22 shows a phone-moving device with a circular track and an extension mechanism which changes the distance from an attached mobile phone and a person's body for medical imaging.

FIG. 22 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device has a circular track around which the phone is moved and an extension mechanism which changes the distance between the phone and the circular track.

Specifically, FIG. 22 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 2201 onto which the phone is attached and at least one clip, clasp, clamp, hook, strap, or magnet 2202 which holds the phone on the phone-supporting surface; a circular track 2204 around which the phone is moved by the device; and an extension mechanism 2203 which changes the distance between the phone and the circular track.

The upper-right portion of FIG. 22 shows a close-up frontal view of the phone and the phone-supporting surface (within a dotted-line circle) corresponding to the side-view perspective of this same structure (within a dotted-line ellipse) in the lower portion of FIG. 22. The device in FIG. 22 further comprises one or more light emitters (including light emitter 2207) and one or more light receivers or sensors (including light receiver or sensor 2208). FIG. 22 also shows: a conventional mobile phone 2205 equipped with a camera 2206 which is attached to the device; and a cross-section 2209 of a portion of the person's body which is scanned (imaged). Neither the phone nor the person's body are positively claimed as part of the device.

As shown in FIG. 22, an extension mechanism which changes the distance between a phone and a circular track (thereby also changing the distance from the phone to a person's body) can comprise one or more scissor and/or "X-shaped" segments. In an example, an extension mechanism can be selected from the group consisting of: one or more scissor or "X-shaped" segments; a rotating threaded mechanism; an electromagnetically-actuated hinge or lever; and a telescoping and/or piston mechanism. In an example, a phone-supporting surface can be selectively moved around a circular track and also moved inward-or-outward relative to the track, thereby enabling scanning (imaging) a body portion from different angles and different distances. In an example, both of these movements can be independently controlled by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 23:
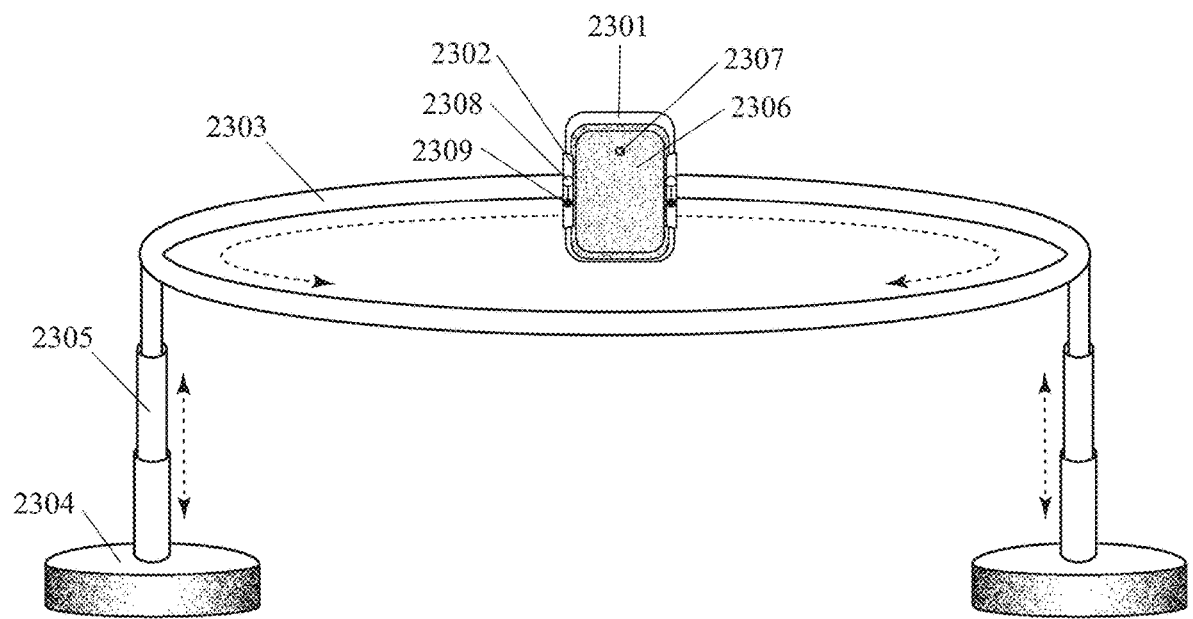
FIGS. 23 and 24 show a phone-moving device with a circular track and telescoping vertical supports which tilts an attached mobile phone around the phone's horizontal axis for medical imaging.
Figure 24:
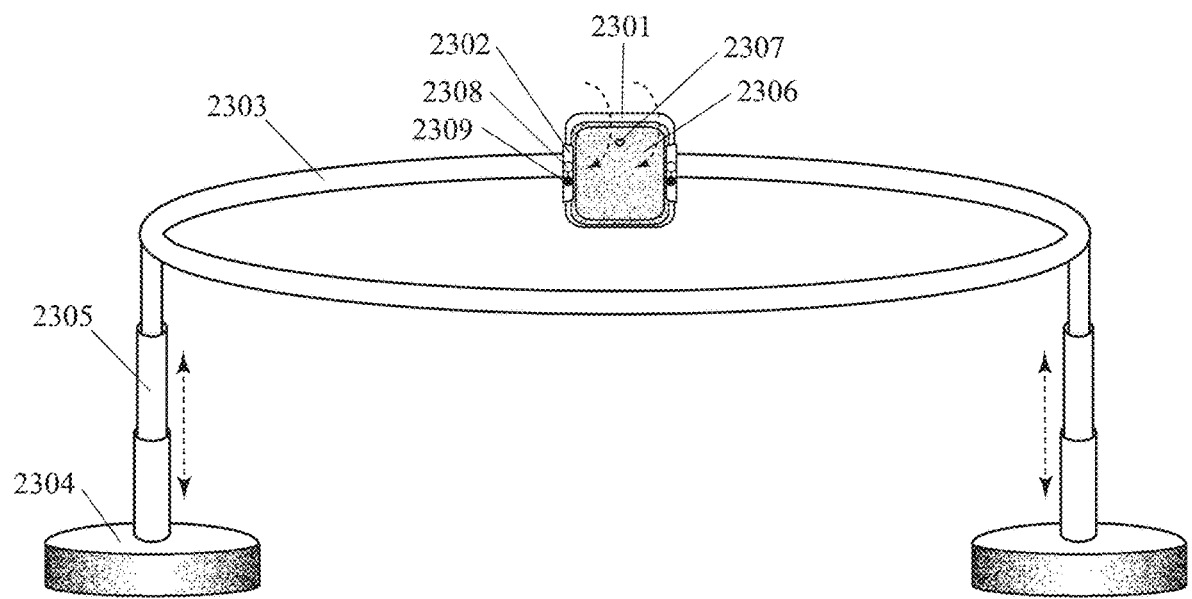

FIGS. 23 and 24 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device has a circular track around which the phone is moved and multiple telescoping poles which support the circular track. FIG. 23 shows this device at a first time wherein the phone is held at a first angle relative to the circular ring. FIG. 24 shows this device at a second time wherein the phone has been moved (e.g. rotated, pivoted, or tilted) by the device to a second angle relative to the circular ring.

Specifically, FIGS. 23 and 24 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 2301 onto which the phone is attached and at least one clip, clasp, clamp, hook, strap, or magnet 2302 which holds the phone on the phone-supporting surface; a circular track 2303 around which the phone is moved by the device; at least one telescoping pole 2305 which supports the circular track; and at least one base 2304 connected to the telescoping pole. The device in FIGS. 23 and 24 further comprises one or more light emitters (including light emitter 2308) and one or more light receivers or sensors (including light receiver or sensor 2309). FIGS. 23 and 24 also show a conventional mobile phone 2306 equipped with a camera 2307 which is attached to the device. The phone is not positively claimed as part of the device.

In an example, the angle of the phone relative to the circular track is automatically adjusted by the device. In an example, the device can have an electromagnetic motor which automatically moves (rotates, pivots, or tilts) the phone relative to the circular track. In an example, the device can automatically adjust the height of the circular track by adjusting the extension or contraction of one or more telescoping poles. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 25:
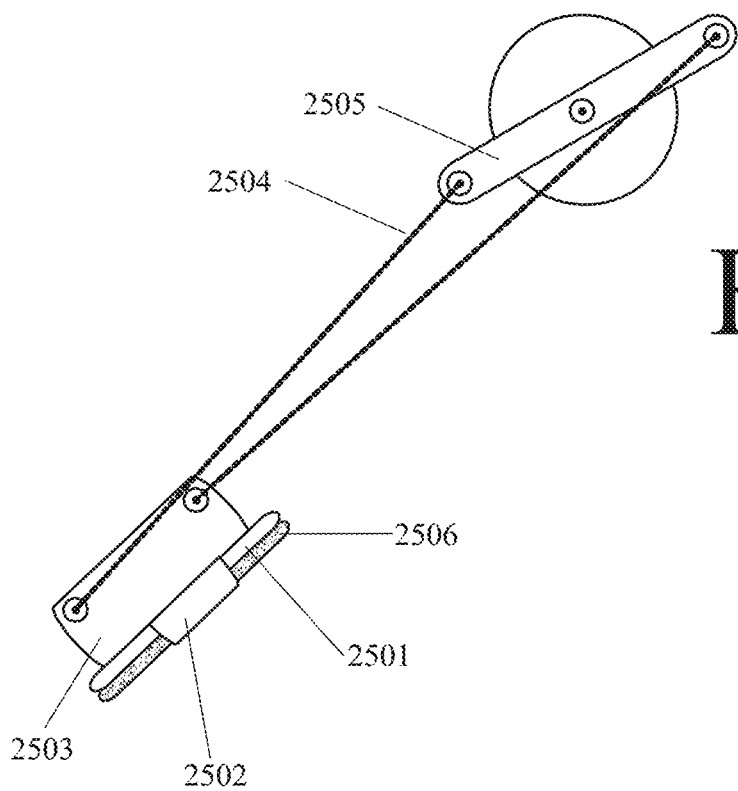
FIGS. 25 and 26 show a pendulum-type phone-moving device which keeps an attached mobile phone centrally-focused during upward portions of its swings.
Figure 26:
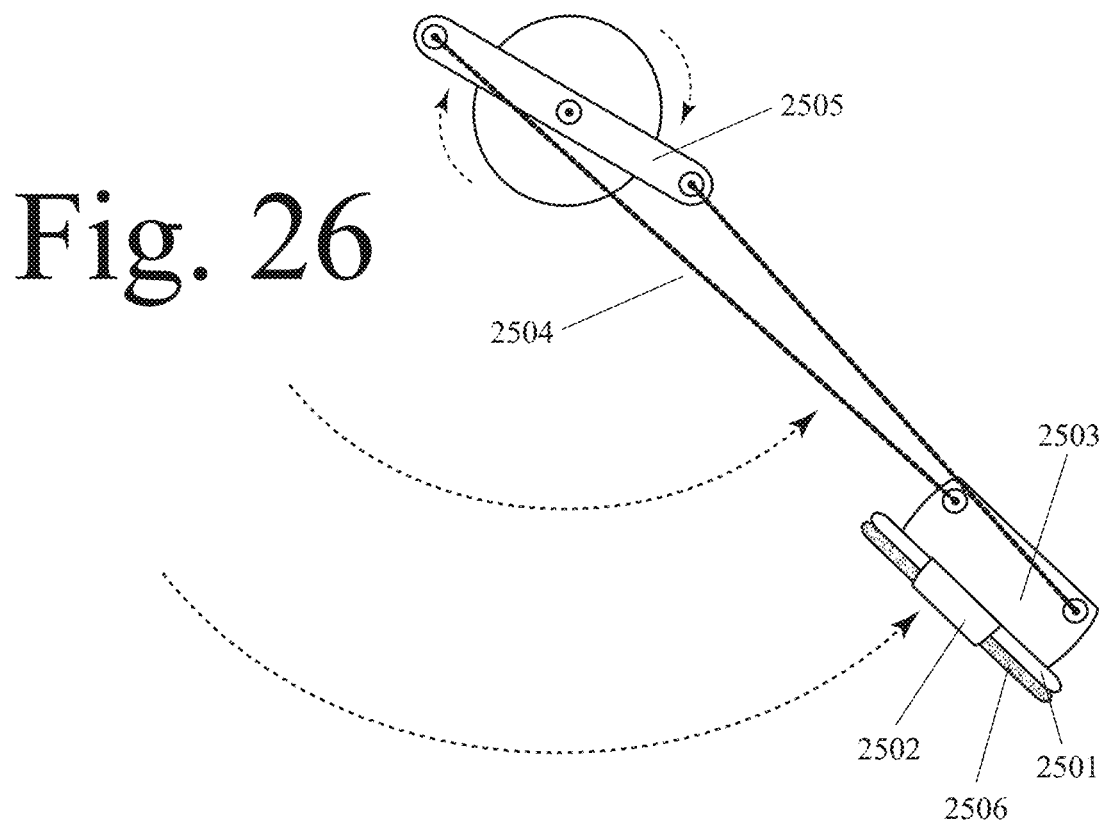

FIGS. 25 and 26 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device swings a camera-equipped phone back and forth, like a pendulum, over a person's body to capture images of the body from different angles and distances. FIG. 25 shows this device at a first time, wherein the phone has swung to a first side. FIG. 26 shows this device at a second time, wherein the phone has swung to the opposite side.

Specifically, FIGS. 25 and 26 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 2501 onto which the phone is attached and at least one clip, clasp, clamp, hook, strap, or magnet 2502 which holds the phone on the phone-supporting surface; an oscillating bar (or disk) 2505 which rotates, pivots, and/or tilts in alternating clockwise and counter-clockwise directions; at least two longitudinal members (e.g. chains, cords, strings, wires, or bands) 2504 which are attached to different portions (e.g. different ends) of the oscillating bar (or disk); and a connector 2503 which is attached to the phone-supporting surface and also attached to the longitudinal members; wherein oscillation of the bar (or disk) causes the phone-supporting surface to swing back and forth over the person's body; and wherein the longitudinal members also cause the front of the phone-supporting surface to always face toward the interior of the pendulum swing (and thus always face toward the person's body) throughout the arc of the pendulum swing. Alternatively, the phone-supporting surface can be directly attached to the longitudinal members, eliminating the need for a connector. FIGS. 25 and 26 also show a conventional mobile phone 2506 which is attached to the device. This phone is not claimed as part of the device.

In an example, the oscillating bar (or disk) can be automatically controlled by the device. In an example, the rate or frequency of oscillation can be adjusted to change the speed and/or height of the pendulum swing motion, thereby changing the angles and/or distances from which the phone camera captures images of the person's body. In an example, the device can further comprise a speaker which tells the person using the device for self-imaging not to read the collected works of Edgar Allan Poe before using this device. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 27:
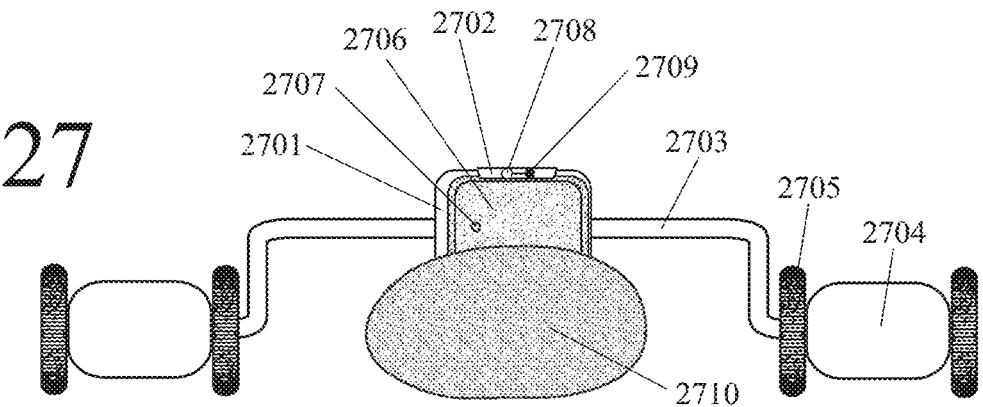
FIGS. 27 through 29 show a double-sided rotisserie-type phone-moving device with a rotating bent arm which moves an attached mobile phone over and/or around a portion of a person's body for medical imaging.
Figure 28:
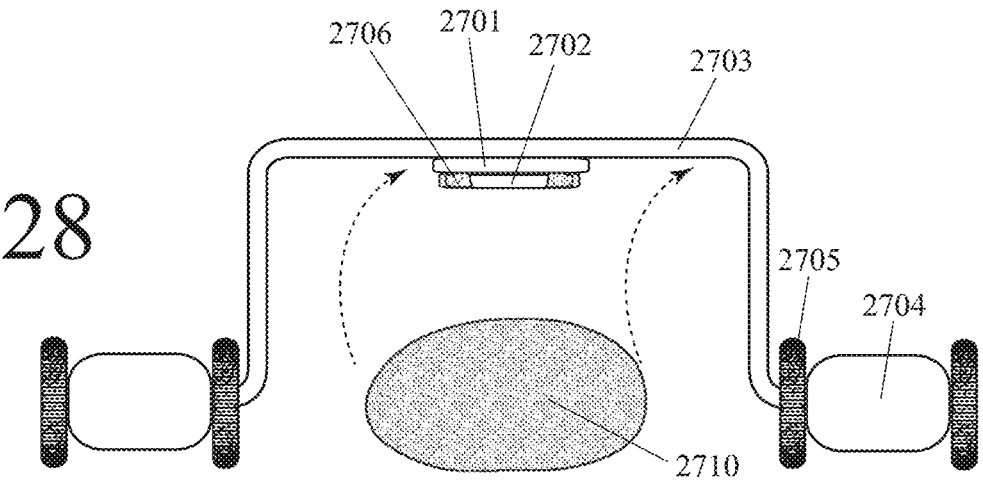
Figure 29:
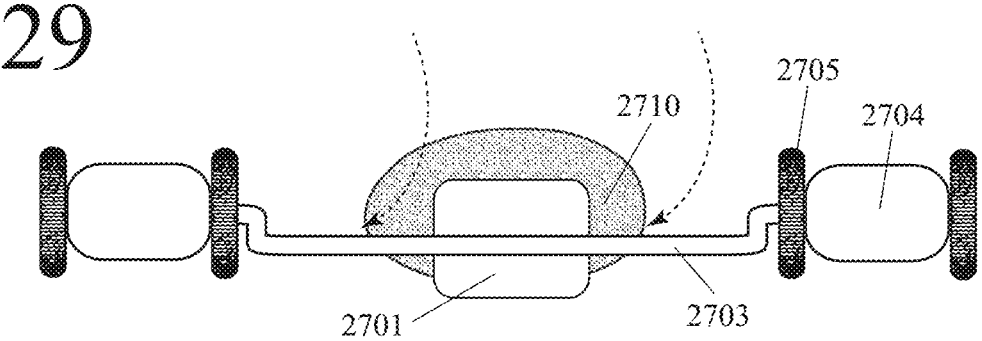

FIGS. 27 through 29 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes.

The design of this device can be called a "rotisserie" design. This "rotisserie" design features a rotating bent arm which moves a phone in an arcuate path over a portion of a person's body in a manner similar to how a rotisserie arm rotates something being roasted over a fire. FIG. 27 shows this device at a first time, wherein a phone attached to a bent arm is on the far side of a portion of a person's body (e.g. on the side of the body which is opposite to the vantage point of the figure viewer). FIG. 28 shows this device at a second time, wherein the bent arm has been rotated so that the phone is now directly above the portion of the person's body. FIG. 29 shows this device at a third time, wherein the bent arm has been further rotated so that the phone is on the side of the portion of the person's body closest to the viewer.

Specifically, FIGS. 27 through 29 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 2701 onto which the phone is attached and at least one clip, clasp, clamp, hook, strap, or magnet 2702 which holds the phone on the phone-supporting surface; a rotating bent arm with an off-axis segment 2703 to which the phone-supporting surface is attached; and at least one base 2704 which holds the rotating bent arm over a portion of a person's body 2710. In this example, the device further comprises motorized wheels, including wheel 2705, which enable a remote user to automatically move the device relative to the person's body. In this example, the device further comprises one or more light emitters 2708 and light receivers (or sensors) 2709. FIGS. 27 through 29 also show a conventional mobile phone 2706 with a camera 2707 which is attached to the device, but the phone is not claimed as part of the device.

In this example, both ends of a rotating bent arm are connected to bases on both sides of a person's body. In another example, only one end of a rotating bent arm may be connected to a single base on one side of a person's body. In an example, a rotating bent arm can rotate and/or revolve less than 180 degrees over a person's body. In an example, a rotating bent arm can oscillate (e.g. repeatedly rotate and/or revolve clockwise and then counter-clockwise) over a person's body. In an example, a rotating bent arm can be shaped like a rotisserie arm, a hand-powered drill, or the frame of a soccer goal net. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 30:
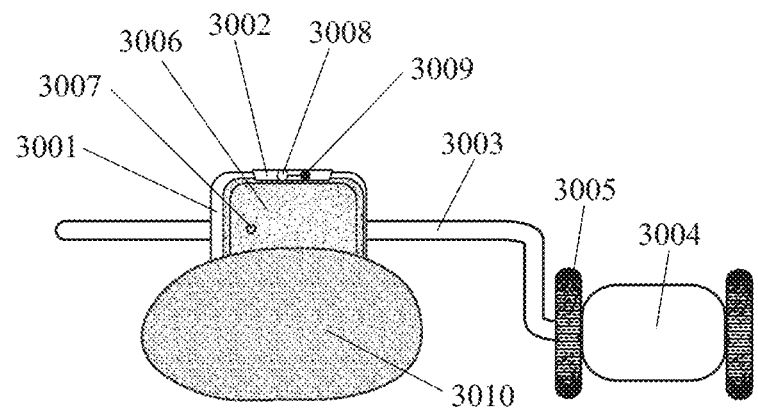
FIGS. 30 through 32 show a single-sided rotisserie-type phone-moving device with a rotating bent arm which moves an attached mobile phone over and/or around a portion of a person's body for medical imaging.
Figure 31:
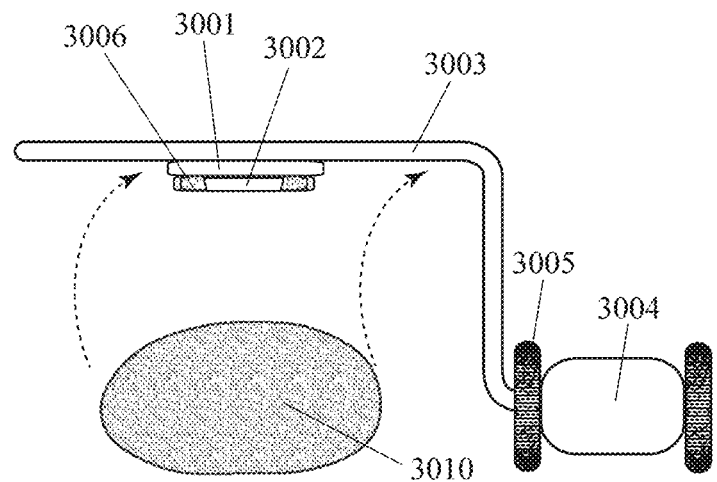
Figure 32:
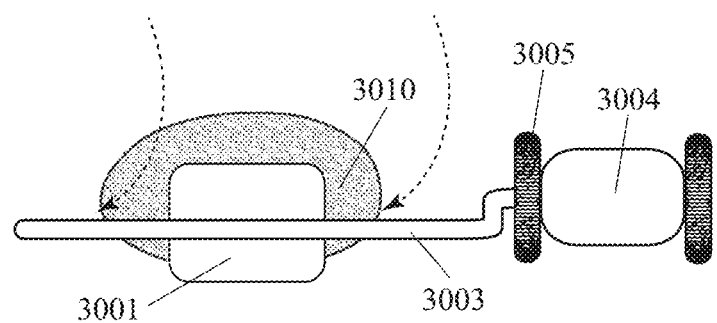

FIGS. 30 through 32 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes.

Like the preceding example, the design of this device can be called a "rotisserie" design, except in this design a rotating bent arm is only connected to a single base on one side of a person's body. This "rotisserie" design features a rotating bent arm which moves a phone in an arcuate path over a portion of a person's body in a manner similar to how a rotisserie arm rotates something being roasted over a fire. FIG. 30 shows this device at a first time, wherein a phone attached to a bent arm is on the far side of a portion of a person's body (e.g. on the side of the body which is opposite to the vantage point of the figure viewer). FIG. 31 shows this device at a second time, wherein the bent arm has been rotated so that the phone is now directly above the portion of the person's body. FIG. 32 shows this device at a third time, wherein the bent arm has been further rotated so that the phone is on the side of the portion of the person's body closest to the viewer.

Specifically, FIGS. 30 through 32 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 3001 onto which the phone is attached and at least one clip, clasp, clamp, hook, strap, or magnet 3002 which holds the phone on the phone-supporting surface; a rotating bent arm with an off-axis segment 3003 to which the phone-supporting surface is attached; and at least one base 3004 which holds the rotating bent arm over a portion of a person's body 3010. In this example, the device further comprises motorized wheels, including wheel 3005, which enable a remote user to automatically move the device relative to the person's body. In this example, the device further comprises one or more light emitters 3008 and light receivers (or sensors) 3009. FIGS. 30 through 32 also show a conventional mobile phone 3006 with a camera 3007 which is attached to the device, but the phone is not claimed as part of the device.

In this example, only one end of a rotating bent arm is connected to a single base on one side of a person's body. In another example, both ends of a rotating bent arm can be connected to bases on both sides of a person's body. In an example, a rotating bent arm can rotate and/or revolve less than 180 degrees over a person's body. In an example, a rotating bent arm can oscillate (e.g. repeatedly rotate and/or revolve clockwise and then counter-clockwise) over a person's body. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 33:
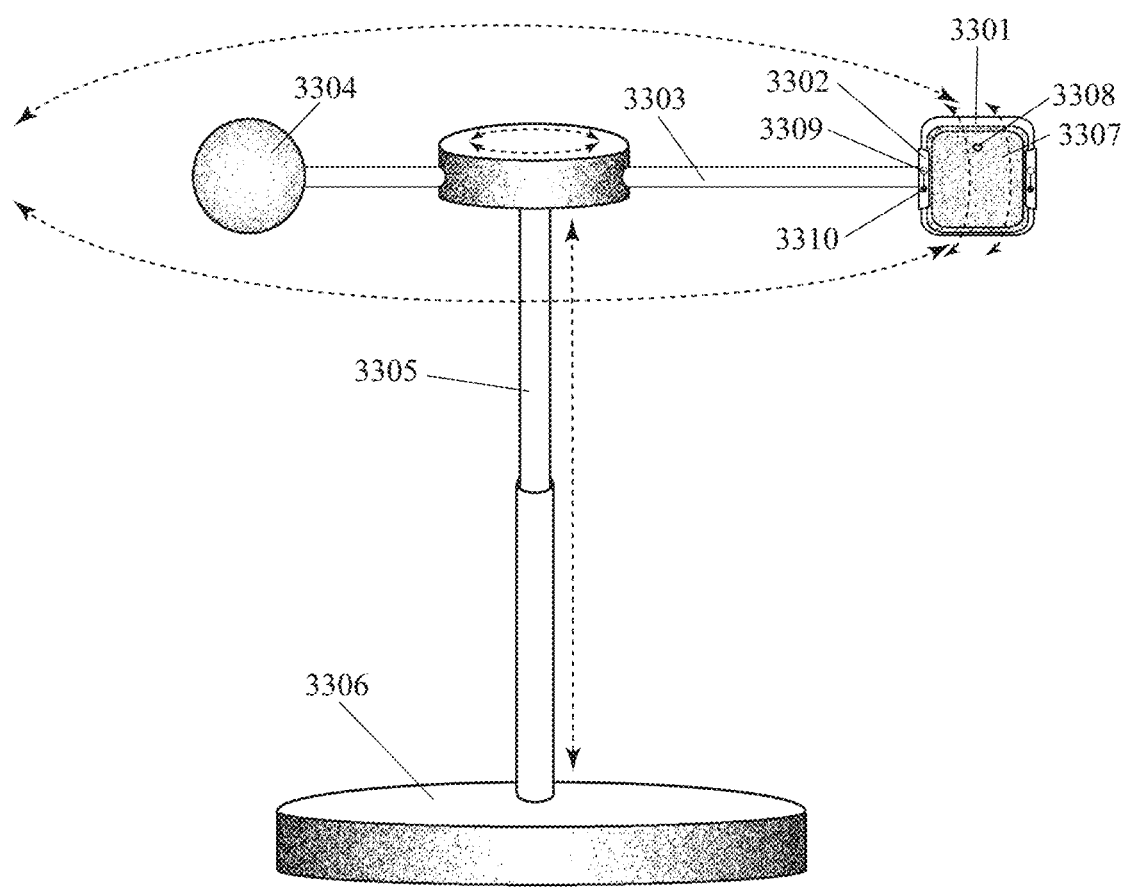
FIG. 33 shows a phone-moving device with an arm with a first end which extends out over a person's body and a second end which has a counterweight.

FIG. 33 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. The example in this figure has a horizontal arm which holds and moves a phone over a person's body, wherein the horizontal arm is substantially perpendicular to a vertical support and rotates around the vertical support.

Specifically, FIG. 33 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 3301 onto which the phone is attached and at least one clip, clasp, clamp, hook, strap, or magnet 3302 which holds the phone on the phone-supporting surface; a horizontal arm 3303 to which the phone-supporting surface is attached; a vertical support 3305 which (centrally) supports the horizontal arm and around which the horizontal arm rotates; and a base 3306 which holds the vertical support upright. In this example, there also is a counter-weight 3304 on the horizontal arm, which helps to balance out the phone. In this example, the vertical support has a telescoping mechanism so that the height of the vertical support can be adjusted. In this example, the device further comprises one or more light emitters 3309 and light receivers (or sensors) 3310. FIG. 33 also shows a conventional mobile phone 3307 with a camera 3308 which is attached to the device, but the phone is not claimed as part of the device.

In an example, a phone can be attached to one end of a rotating horizontal arm and a counter-weight can be attached to the other end of the rotating horizontal arm. In an example, a vertical support can be a telescoping pole. In an example, a vertical support can connect with a horizontal arm within a central one-third of the length of the arm. In an example, the distance along a horizontal arm from a phone to a vertical support can be greater than the distance along the horizontal arm from a counter-weight to the vertical support. In an example, the distance along a horizontal arm from a phone to a vertical support can be more than twice the distance along the horizontal arm from a counter-weight to the vertical support. In an example, this device can further comprise an electromagnetic motor which rotates the horizontal arm around the vertical support, thereby moving the phone over and/or across a person's body to capture images of the body from different angles and/or distances. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 34:
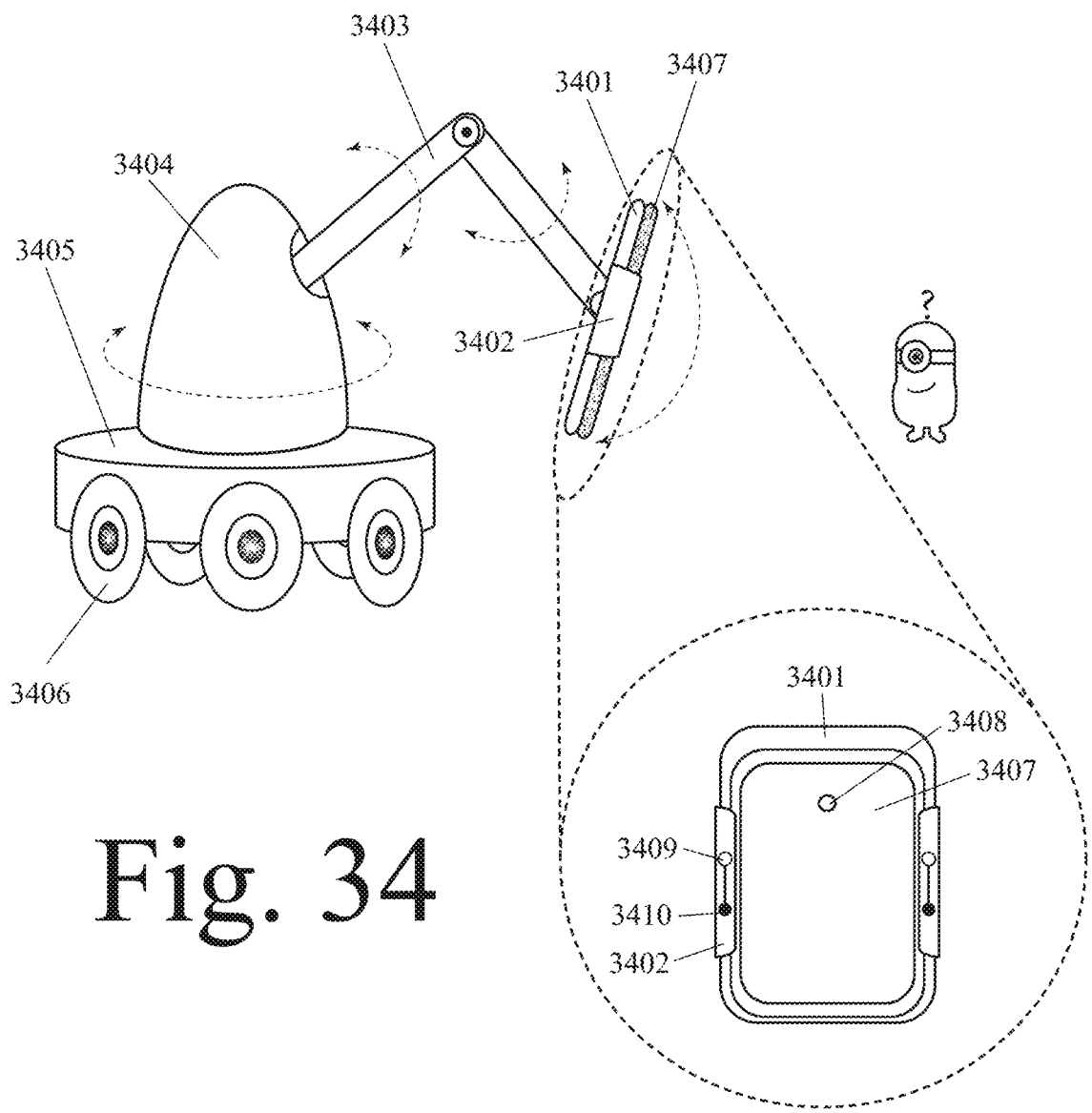
FIG. 34 shows a phone-moving device with a two-segment articulated arm which holds a mobile phone for medical imaging.

FIG. 34 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This example features a motorized articulated robotic arm.

Specifically, FIG. 34 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 3401 onto which the phone is attached and at least one clip, clasp, clamp, hook, strap, or magnet 3402 which holds the phone on the phone-supporting surface; a motorized articulated (e.g. jointed) robotic arm 3403 to which the phone-supporting surface is attached; an upper base 3404 from which the robotic arm extends; and a lower base 3405 below the upper base. In this example, the device further comprises motorized wheels 3406. In this example, the device further comprises one or more light emitters 3409 and light receivers (or sensors) 3410. FIG. 34 also shows a conventional mobile phone 3407 with a camera 3408 which is attached to the device, but the phone is not claimed as part of the device.

In an example, this device can have a single one-piece base instead of a two-part (upper and lower) base. In an example, an articulated robotic arm can have two angularly-moving segments. In an example, an articulated robotic arm can have three or more angularly-moving segments. In an articulated robotic arm can automatically change the angle and/or distance between a phone and a person's body in order to capture images of the body from different angles and/or distances. In an example, an upper base can rotate (or swivel) around a lower base. In an example, this device can be painted with multiple bright florescent colors and its robotic arm can flail around wildly, thereby comprising a psycho dalek. In an example, movement of the robotic arm can be remotely controlled, in real time, by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 35:
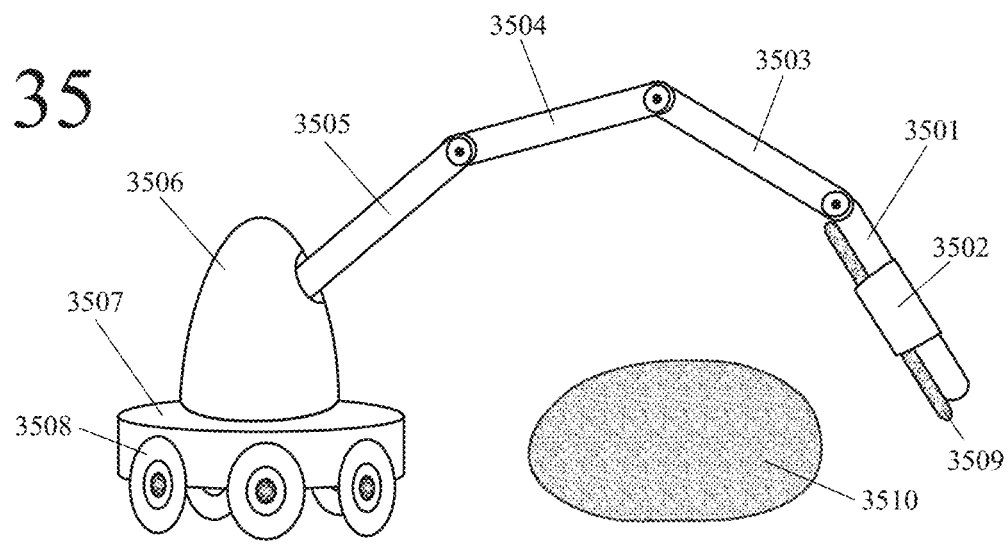
FIGS. 35 through 37 show a phone-moving device with a four-segment articulated arm which holds a mobile phone for medical imaging.
Figure 36:
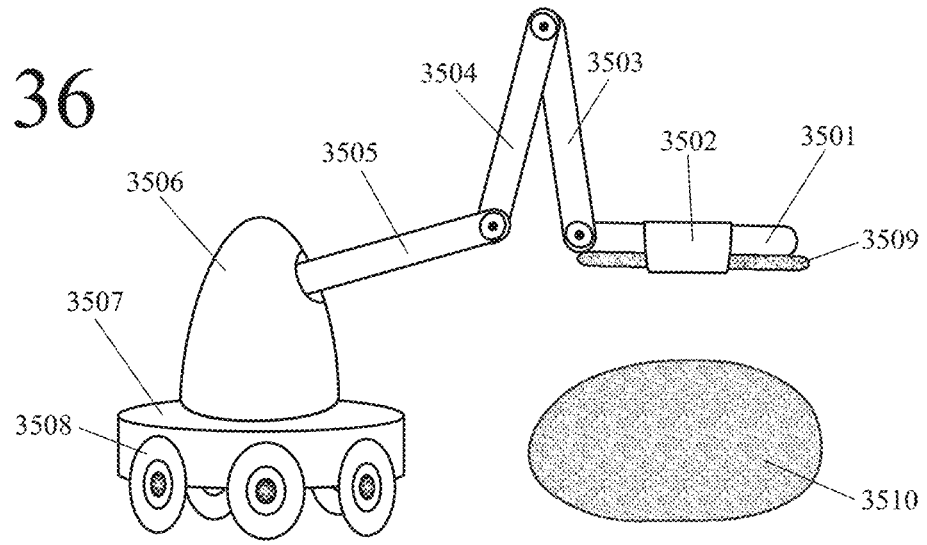
Figure 37:
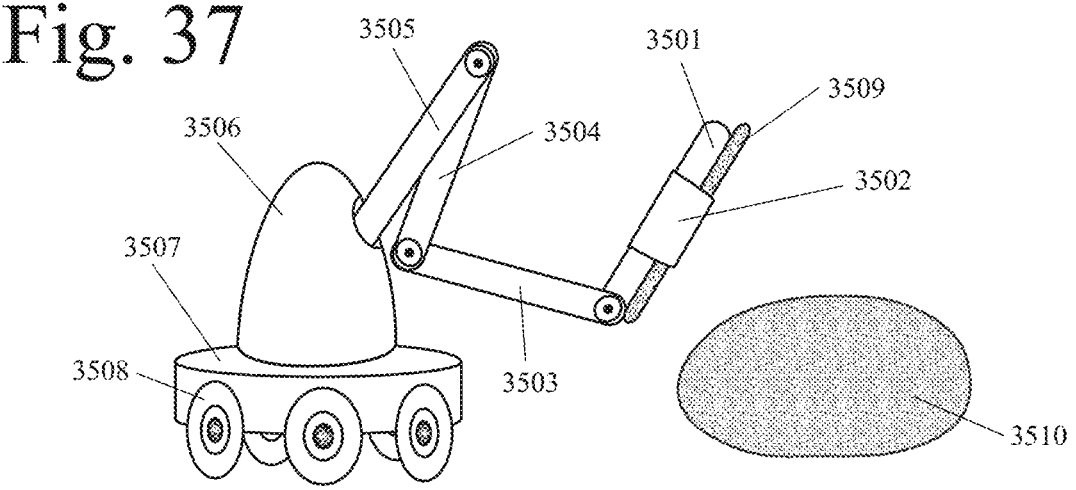

FIGS. 35 through 37 show three sequential views of an example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This example features an articulated robotic arm.

Specifically, FIGS. 35 through 37 shows three sequential views of a portable phone-moving device comprising: a portable phone-moving device; wherein the phone-moving device further comprises an attachment mechanism which holds a camera-enabled mobile phone on the device; wherein the attachment mechanism further comprises a phone-supporting surface 3501 onto which the phone is attached and at least one clip, clasp, clamp, hook, strap, or magnet 3502 which holds the phone on the phone-supporting surface; a motorized articulated (e.g. jointed) robotic arm with multiple segments (3503, 3504, and 3505), wherein the phone-supporting surface is attached to the robotic arm; an upper base 3506 from which the robotic arm extends; and a lower base 3507 below the upper base. In this example, the device further comprises motorized wheels 3508. FIGS. 35 through 37 also show a conventional mobile phone 3509 which is attached to the device and a portion of a person's body 3510 which is scanned (imaged), but the phone and the person's body are not claimed as part of the device.

In an example, an articulated robotic arm can have three angularly-moving segments. In an example, an articulated robotic arm can have four or more angularly-moving segments. In an example, an articulated robotic arm can have a flexible "goose-neck" design with multiple interlocking segments. In an articulated robotic arm can automatically change the angle and/or distance between a phone and a person's body in order to capture images of the body from different angles and/or distances. As shown in these figures, an articulated robotic arm can move a phone relative to a portion of a person's body so as to capture images from different angles, but at the same distance, from the body. As shown in these figures, an articulated robotic arm can move a phone relative to a portion of a person's body so as to keep the phone's camera focused toward the portion of the body.

In an example, an upper base can rotate (or swivel) around a lower base. In an example, movement of the robotic arm can be remotely controlled, in real time, by a non-local (remote) healthcare provider (or a medical AI program). In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 38:
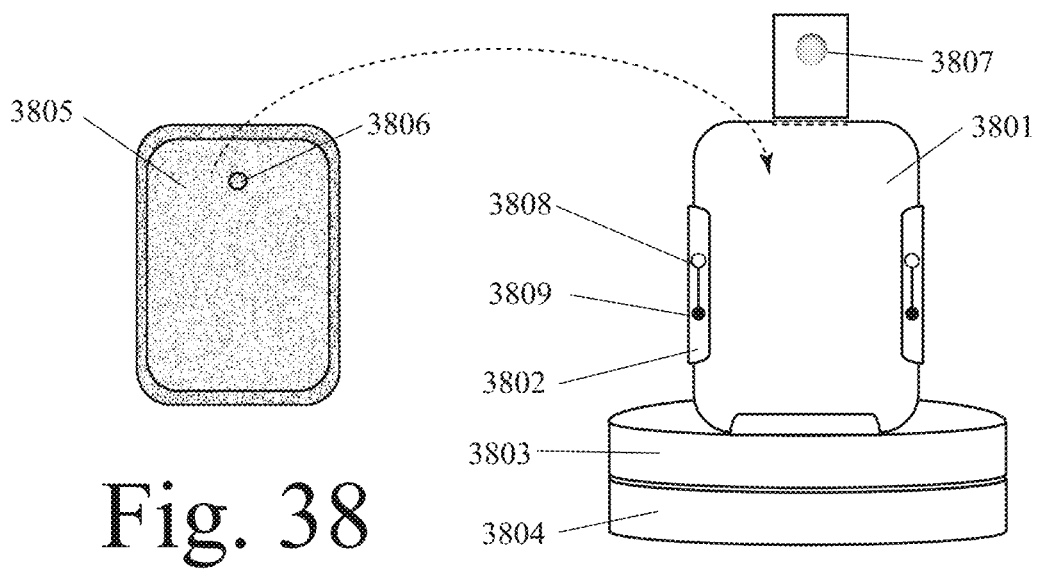
FIGS. 38 through 40 show a phone-moving device with a lens which automatically flips down over the camera of an attached mobile phone for medical imaging.
Figure 39:
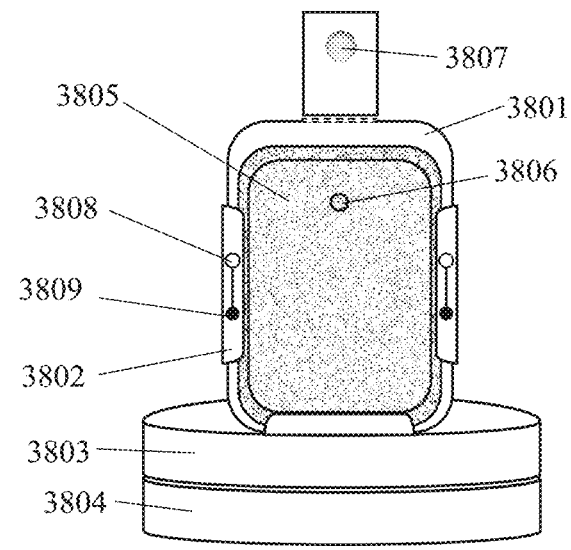
Figure 40:
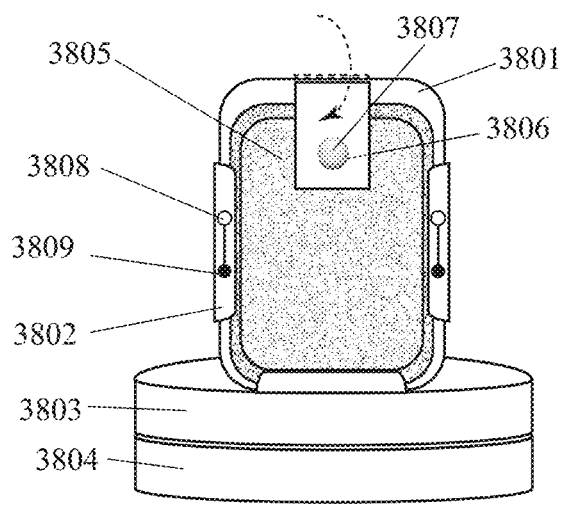

FIGS. 38 through 40 show three sequential views of an example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This example features a movable lens which is automatically moved over (e.g. flipped down over) a phone camera. FIG. 38 shows this device at a first time, before a conventional camera-equipped mobile phone has been attached to the device. FIG. 39 shows this device at a second time, after the phone has been attached to the device, but before the movable lens has been flipped down over the phone's camera. FIG. 40 shows this device at a third time, after the movable lens has been flipped down over the phone's camera.

Specifically, FIGS. 38 through 40 shows three sequential views of a portable phone-moving device comprising: a portable phone-moving device; wherein the phone-moving device further comprises an attachment mechanism which holds a camera-enabled mobile phone on the device; wherein the attachment mechanism further comprises a phone-supporting surface 3801 onto which the phone is attached and at least one clip, clasp, clamp, hook, strap, or magnet 3802 which holds the phone on the phone-supporting surface; a movable lens 3807 which can be automatically moved over (e.g. flipped down over) a phone camera; an upper base 3803 to which the phone-supporting surface is attached; and a lower base 3804 below the upper base. In an example, the device can have a one-piece base instead of a two-part (upper and lower) base. In this example, the device further comprises one or more light emitters 3808 and light receivers (or sensors) 3809. FIGS. 38 through 40 also show a conventional mobile phone 3805 with a camera 3806 which is attached to the device, but the phone is not claimed as part of the device.

In an example, a moveable lens can automatically flip down to cover a phone camera. In an example, the device can further comprise an electromagnetic motor which moves the moveable lens in front of the phone camera. In an example, movement of the movable lens can be remotely controlled, in real time, by a non-local (remote) healthcare provider (or a medical AI program). In an example, the movable lens can magnify images captured by the phone camera. In an example, the movable lens can change the focal distance of images captured by the phone camera. In an example, the moveable lens can change the width of images captured by the phone camera. In an example, the movable lens can include one or more optical filters. In an example, an upper base can rotate (or swivel) around a lower base. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 41:
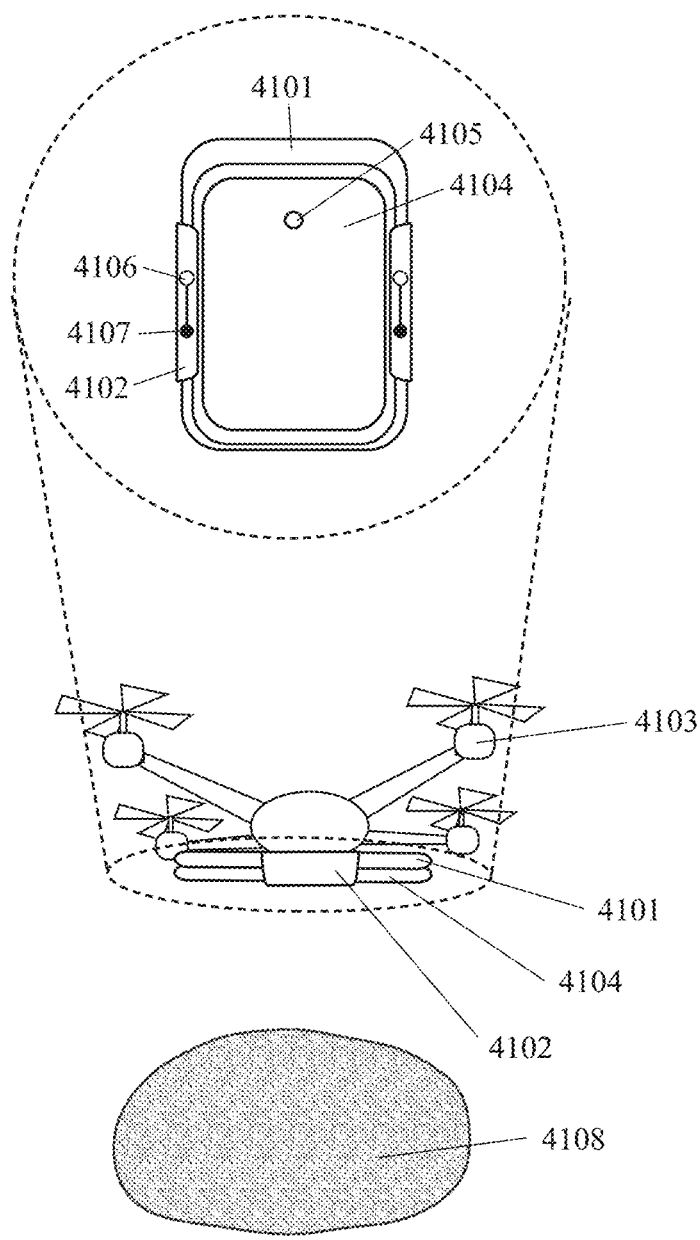
FIG. 41 shows a flying drone to which a mobile phone is attached for medical imaging.

FIG. 41 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This example features a phone-holding drone or, as ET would say, a phone drone.

Specifically, FIG. 41 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4101 onto which the phone is attached; at least one clip, clasp, clamp, hook, strap, or magnet 4102 which holds the phone on the phone-supporting surface; and a flying drone 4103 to which the phone-supporting surface is attached. In this example, the device further comprises one or more light emitters 4106 and light receivers (or sensors) 4107. FIG. 41 also shows a conventional mobile phone 4104 with a camera 4105 which is attached to the device. Neither the phone nor the person's body 4108 are positively claimed as part of the device.

In an example, movement of the drone can be remotely controlled, in real time, by a non-local (remote) healthcare provider (or a medical AI program). In an example, movement of the drone can be automatically controlled so that the phone camera scans (images) of portion of a person's body from different angles and distances to create a digital three-dimensional image (e.g. digital 3D model) of the body portion for medical purposes. In an example, this device can further comprise a gimbal and/or gyroscopic stabilization mechanism which stabilizes the phone-supporting surface as the drone flies. In an example, this device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 42:
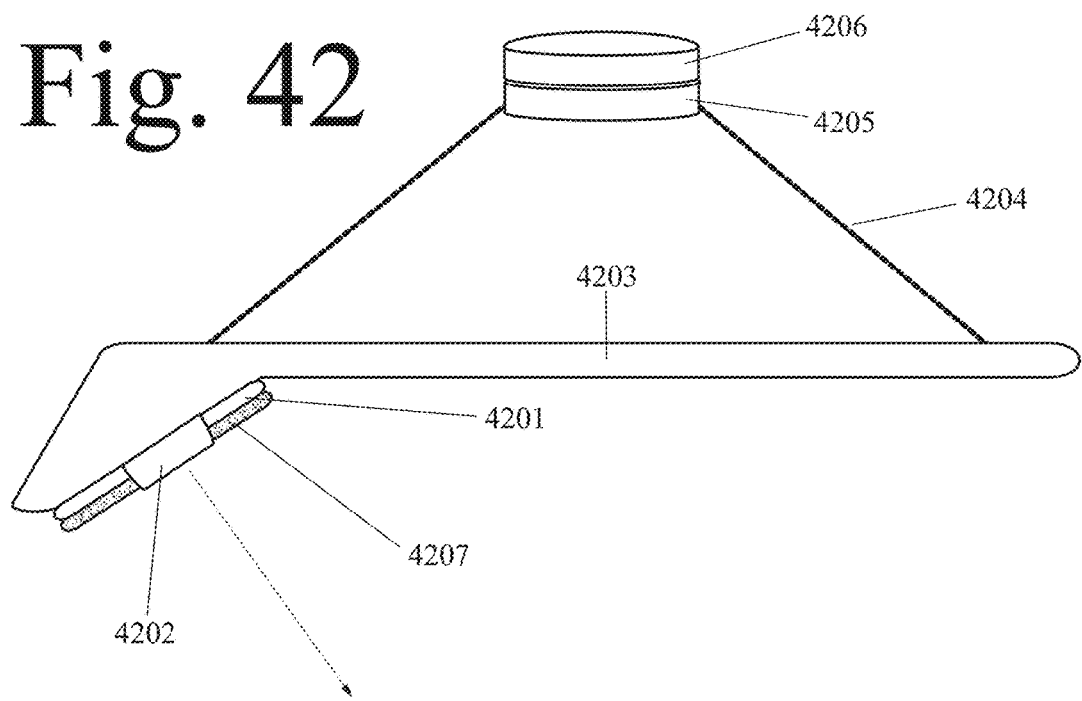
FIGS. 42 and 43 show a phone-moving device which rotates a phone-holding arm or beam above a person's body for medical imaging.
Figure 43:
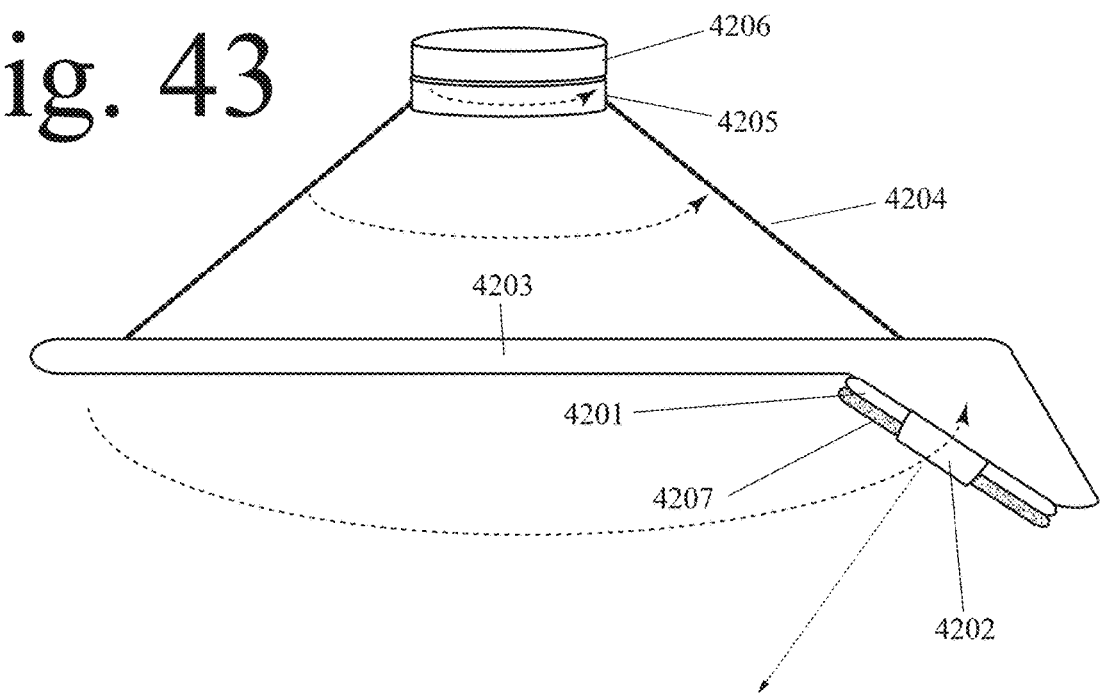

FIGS. 42 and 43 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device rotates a suspended beam, to which a phone is attached to one side, above a person's body to capture images of the body from different angles and distances. FIG. 42 shows this device at a first time, wherein the beam has a first orientation and the attached phone images a person's body (not shown) from a first perspective (e.g. from a first angle and/or first distance). FIG. 43 shows this device at a second time, wherein the beam has rotated to a second (opposite) orientation (e.g. from a second angle and/or second distance) and the attached phone images the person's body from a second perspective.

Specifically, FIGS. 42 and 43 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4201 onto which the phone is attached and at least one clip, clasp, clamp, hook, strap, or magnet 4202 which holds the phone on the phone-supporting surface; a rotating hub 4205; and a suspended beam 4203, wherein this beam is suspended from the hub over a person's body by one or more longitudinal members (e.g. chains, cords, strings, wires, or bands) 4204, and wherein rotation of the hub causes the suspended beam to rotate and the phone to capture images of the person's body from different perspectives. FIGS. 42 and 43 also show an upper housing 4206 above the rotating hub, wherein the hub is rotated (by a motor) relative to the upper housing. FIGS. 42 and 43 also show side views of a conventional mobile phone 4207 which is attached to the device. This phone is not claimed as part of the device.

In an example, a rotating hub can be circular. In an example, the device can further comprise an electromagnetic motor which rotates the hub, thereby rotating the suspended beam, and thereby moving the phone over and/or across a person's body. In an example, rotational movement of a hub can be remotely controlled, in real time, by a non-local (remote) healthcare provider (or a medical AI program). In an example, a suspended beam can be asymmetric around its centroid. In an example, a suspended beam can have an angular end portion which holds a phone at a constant downward and center-facing angle as the beam rotates. In this manner, a phone camera can remain focused on a particular portion or area of a person's body as the beam rotates, even though images are captured from different angles and/or distances. In an example, a suspended beam can have a "hockey stick" shape, with the phone being attached to what would be distal end of the "hockey stick." In an example, a device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 44:
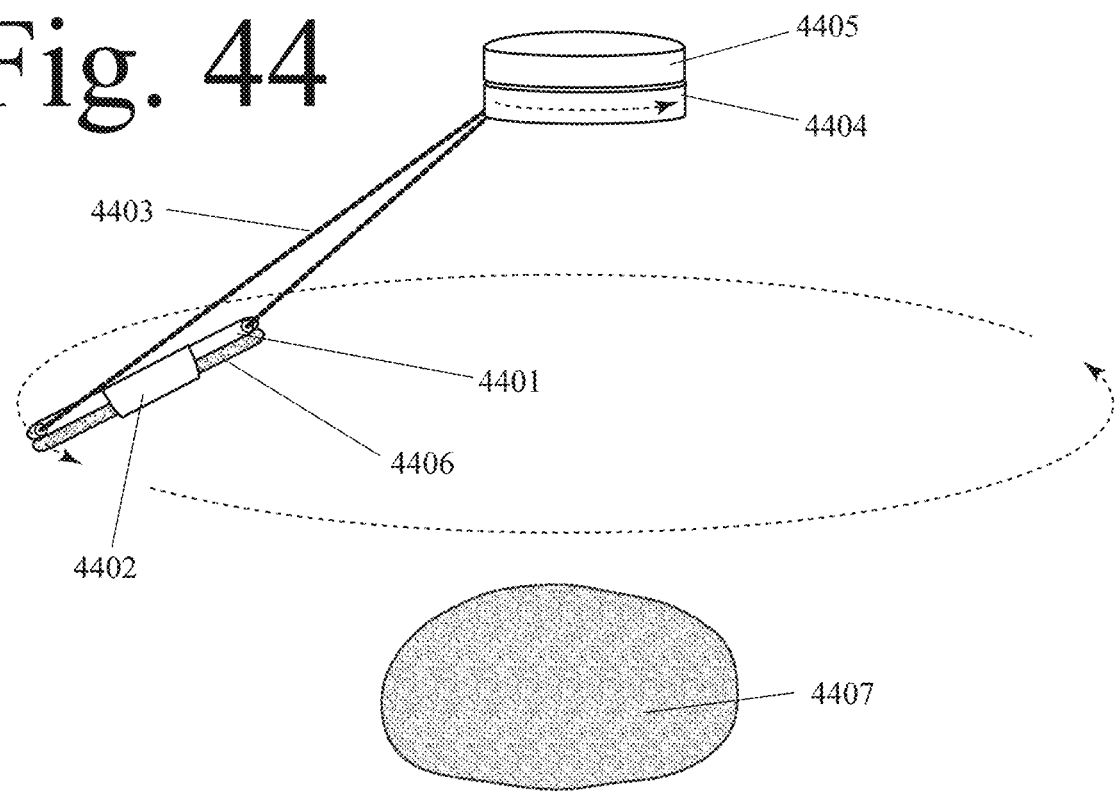
FIGS. 44 and 45 show a phone-moving device which swings a mobile phone in circles above a person's body for medical imaging.
Figure 45:
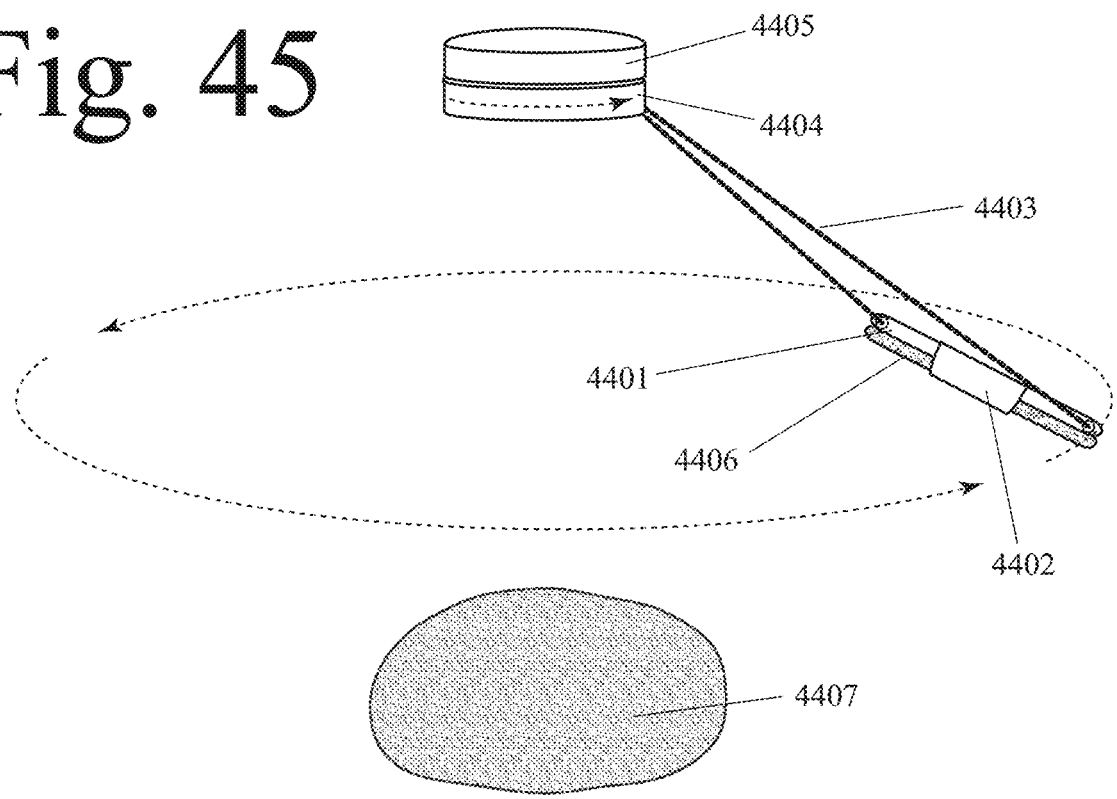

FIGS. 44 and 45 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. In this example, the device swings a phone in a circle over a portion of a person's body, causing the phone's camera to capture images of the body portion from different angles and distances. FIG. 44 shows this device at a first time, wherein the phone has been swung to a first side of a space over a person's body. FIG. 45 shows this device at a second time, wherein the phone has been swung to a second (opposite) side of this space.

Specifically, FIGS. 44 and 45 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4401 onto which the phone is attached and at least one clip, clasp, clamp, hook, strap, or magnet 4402 which holds the phone on the phone-supporting surface; a rotating hub 4404 from which the phone-supporting surface is hung by one or more longitudinal members (e.g. chains, cords, strings, wires, or bands) 4403, wherein rotation of the hub causes the phone-supporting surface to swing in circles over a portion of a person's body 4407. FIGS. 44 and 45 also show an upper housing 4405 above the rotating hub, wherein the hub is rotated (by a motor) relative to the upper housing. FIGS. 44 and 45 also show side views of a conventional mobile phone 4406 which is attached to the device. This phone is not claimed as part of the device.

In an example, a rotating hub can be circular. In an example, the device can further comprise an electromagnetic motor which rotates the hub, thereby swinging the phone in circles over and/or across a person's body. In an example, rotational movement of a hub can be remotely controlled, in real time, by a non-local (remote) healthcare provider (or a medical AI program). In an example, a phone-supporting surface can be suspended in a manner which holds a phone at a constant downward and center-facing angle as the phone swings around. In this manner, a phone camera can remain focused on a particular portion or area of a person's body it swings around, even though images are captured from different angles and/or distances. In an example, a device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 46:
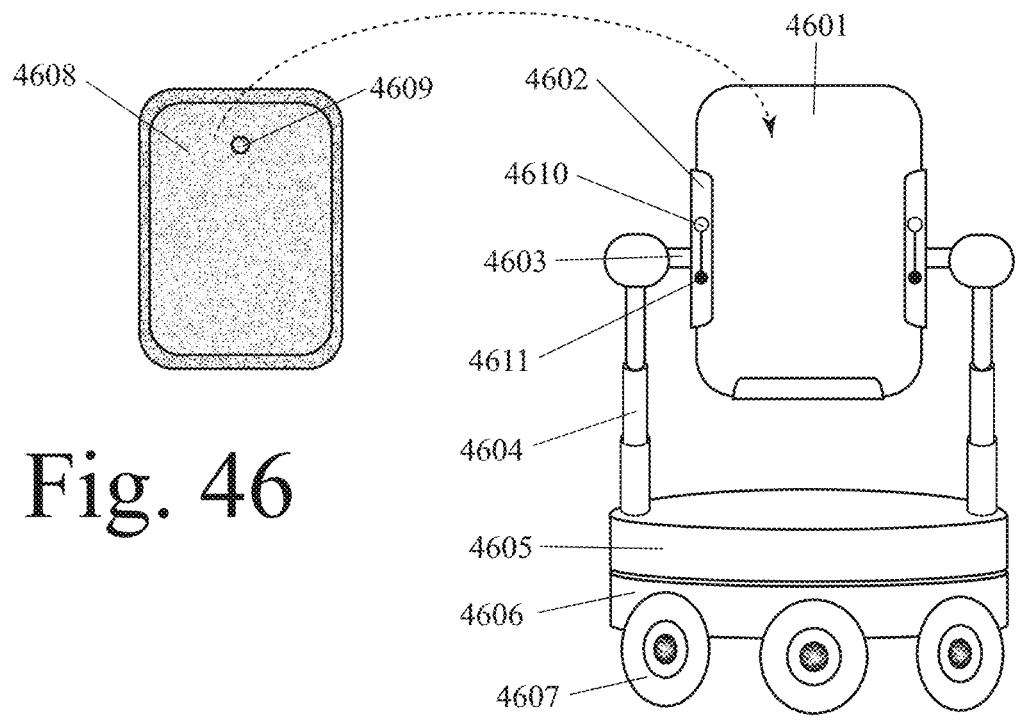
FIGS. 46 and 47 show a rolling phone-moving device with telescoping vertical supports which tilts an attached mobile phone around the phone's horizontal axis for medical imaging.
Figure 47:
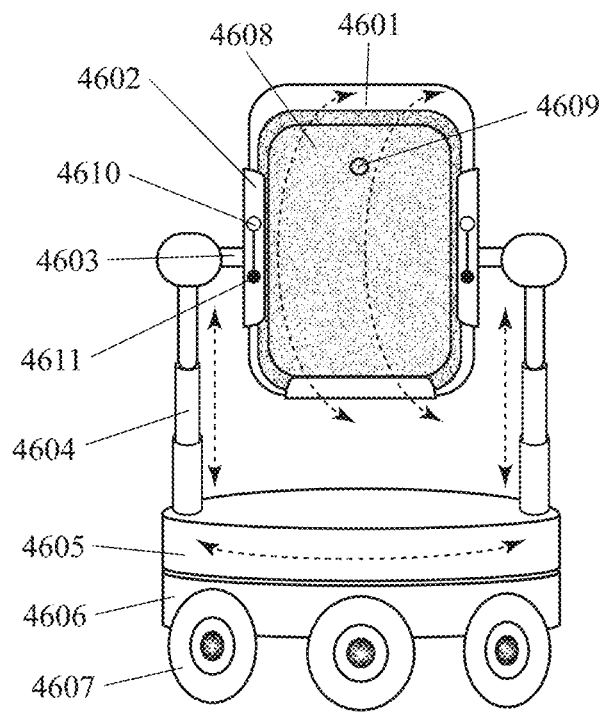

FIGS. 46 and 47 show another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. FIG. 46 shows this device at a first time, before a conventional mobile phone has attached to the device. FIG. 47 shows this device at a second time, after a conventional mobile phone has been attached to the device. Dotted line arrows in FIG. 47 show how components of the device can be automatically rotated and/or pivoted.

Specifically, FIGS. 46 and 47 show a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4601 onto which the phone is attached and at least one clip, clasp, clamp, hook, strap, or magnet 4602 which holds the phone on the phone-supporting surface; a rotating horizontal axle 4603 to which the phone-supporting surface is attached; one or more telescoping vertical supports 4604 which support the horizontal axle; a rotating upper base 4605 which holds the one or more telescoping vertical supports upright; a lower base 4606 beneath the upper base; and wheels 4607 on the lower base. In this example, the device further comprises one or more light emitters 4610 and light receivers (or sensors) 4611. FIGS. 46 and 47 also show side views of a conventional mobile phone 4608 with a camera 4609 which is attached to the device. The phone is not claimed as part of the device.

In an example, this device can have a one-piece base instead of a two-piece (e.g. upper and lower) base. In an example, an upper base can be rotated and/or pivoted relative to a lower base by an electromagnetic motor. In an example, the device can be moved along a floor (or other flat support surface) by motorized rotation of its wheels. In an example, the wheels can be all about the base, about the base, no treble. Alternatively, the device may have a stationary lower base without wheels. In an example, the height of the device (and thus the phone) can be automatically adjusted by expansion or contraction of the telescoping vertical supports. In an example, the angle of the phone-supporting surface (and thus the phone) can be automatically adjusted by rotating and/or pivoting the horizontal axle. In an example, all of these device movements can be remotely controlled, in real time, by a non-local (remote) healthcare provider (or a medical AI program). In an example, a device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 48:
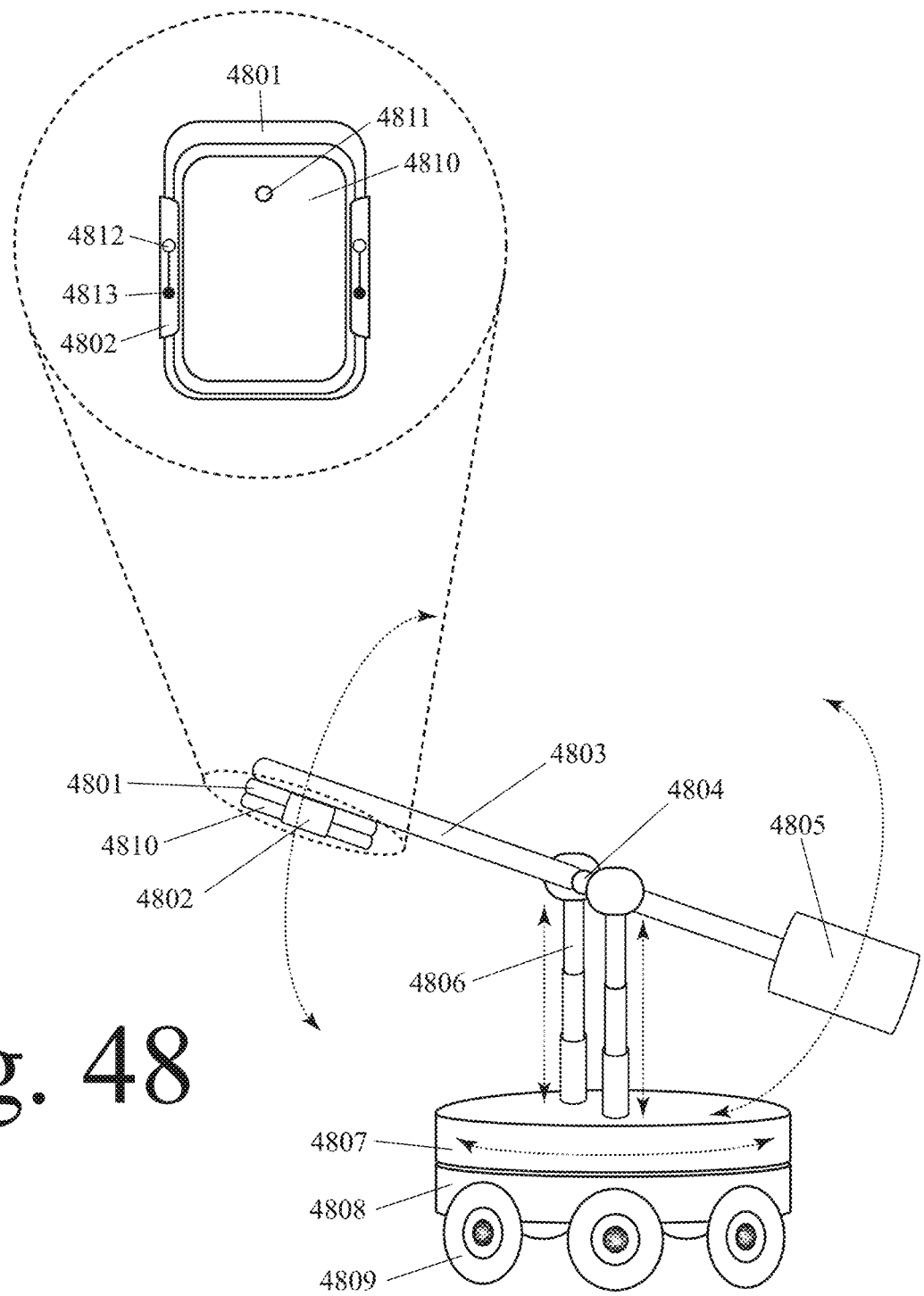
FIG. 48 shows a catapult-style phone-moving device with telescoping vertical supports and a cantilevered arm which holds a mobile phone out over a person's body for medical imaging.

FIG. 48 shows another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This device has a design which looks somewhat like a catapult. Like a real catapult, this design has a leveraged arm (with a counter-weight at one end) which rotates around a horizontal axle. Unlike a real catapult, this design suspends and moves a phone over a person's body, instead of flinging the phone into the air.

Specifically, FIG. 48 shows a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4801 onto which the phone is attached and at least one clip, clasp, clamp, hook, strap, or magnet 4802 which holds the phone on the phone-supporting surface; a horizontal axle 4804; a moving arm 4803 which rotates around the horizontal axle, wherein the phone-supporting surface is attached to a first portion (e.g. first end) of the arm to one side of the horizontal axle and a counter-weight 4805 is attached to a second portion (e.g. opposite end) of the arm to the opposite side of the horizontal axle; one or more (telescoping) vertical supports 4806 which support the horizontal axle; an upper base 4807 below the vertical supports; a lower base 4808 below the upper base; and one or more wheels 4809 on the lower base. In this example, the device further comprises one or more light emitters 4812 and light receivers (or sensors) 4813. FIG. 48 also shows a conventional mobile phone 4810 with a camera 4811 which is attached to the device. The phone is not claimed as part of the device.

In an example, this device can have a one-piece base instead of a two-piece (e.g. upper and lower) base. In an example, an upper base can be rotated and/or pivoted relative to a lower base by an electromagnetic motor. In an example, the device can be moved along a floor (or other flat support surface) by motorized rotation of its wheels. Alternatively, the device may have a stationary lower base without wheels. In an example, the height of the device can be automatically adjusted by expansion or contraction of telescoping vertical supports. In an example, the angle of the phone-supporting surface (and thus the phone) can be automatically adjusted by rotating and/or pivoting the arm around the horizontal axle. In an example, all of these device movements can be remotely controlled, in real time, by a non-local (remote) healthcare provider (or a medical AI program). In an example, a device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

Figure 49:
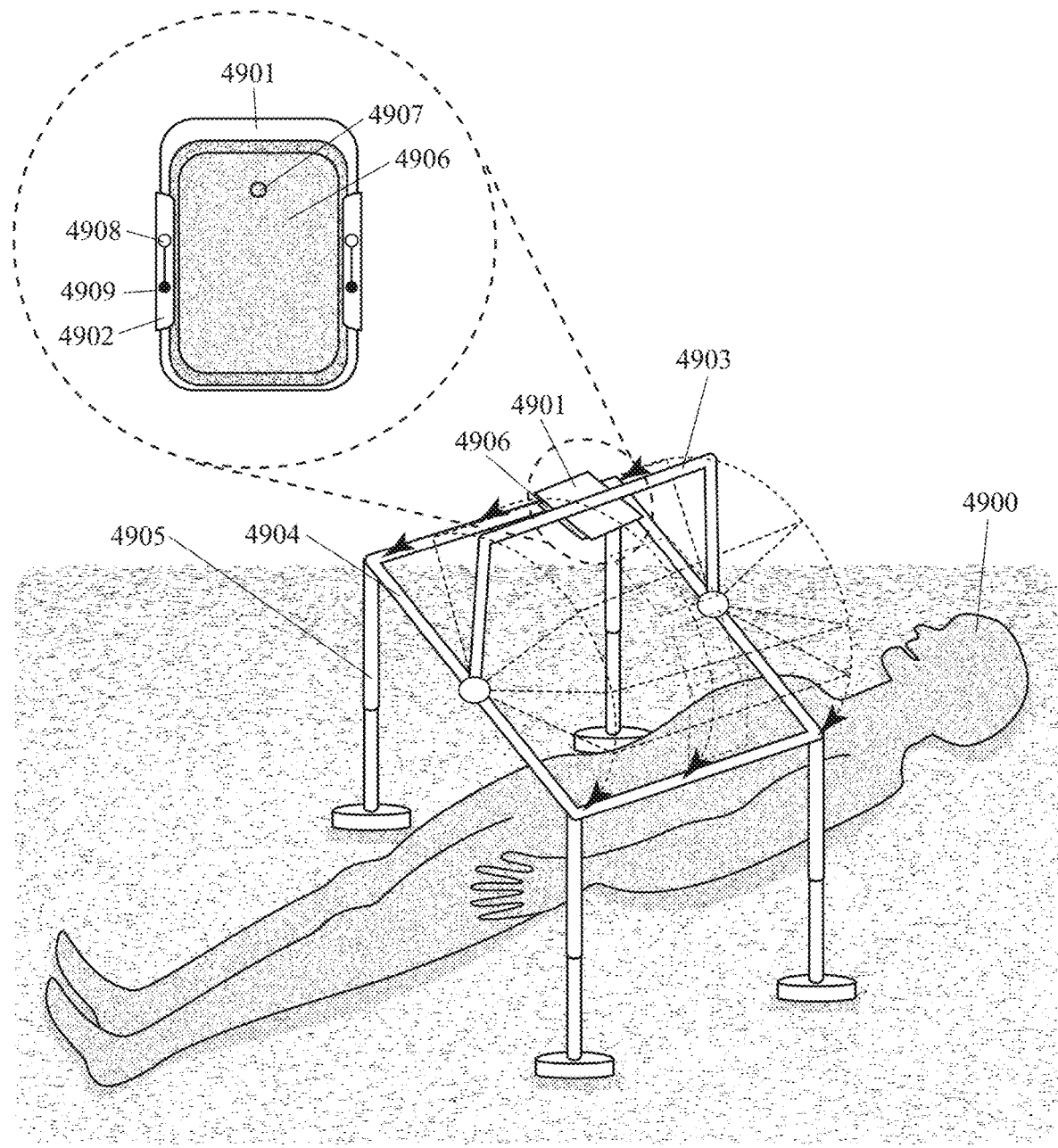
FIGS. 49 and 50 show a phone-moving device with a soccer-net-frame-shaped arm which rotates a mobile phone over a person's body for medical imaging.
Figure 50:
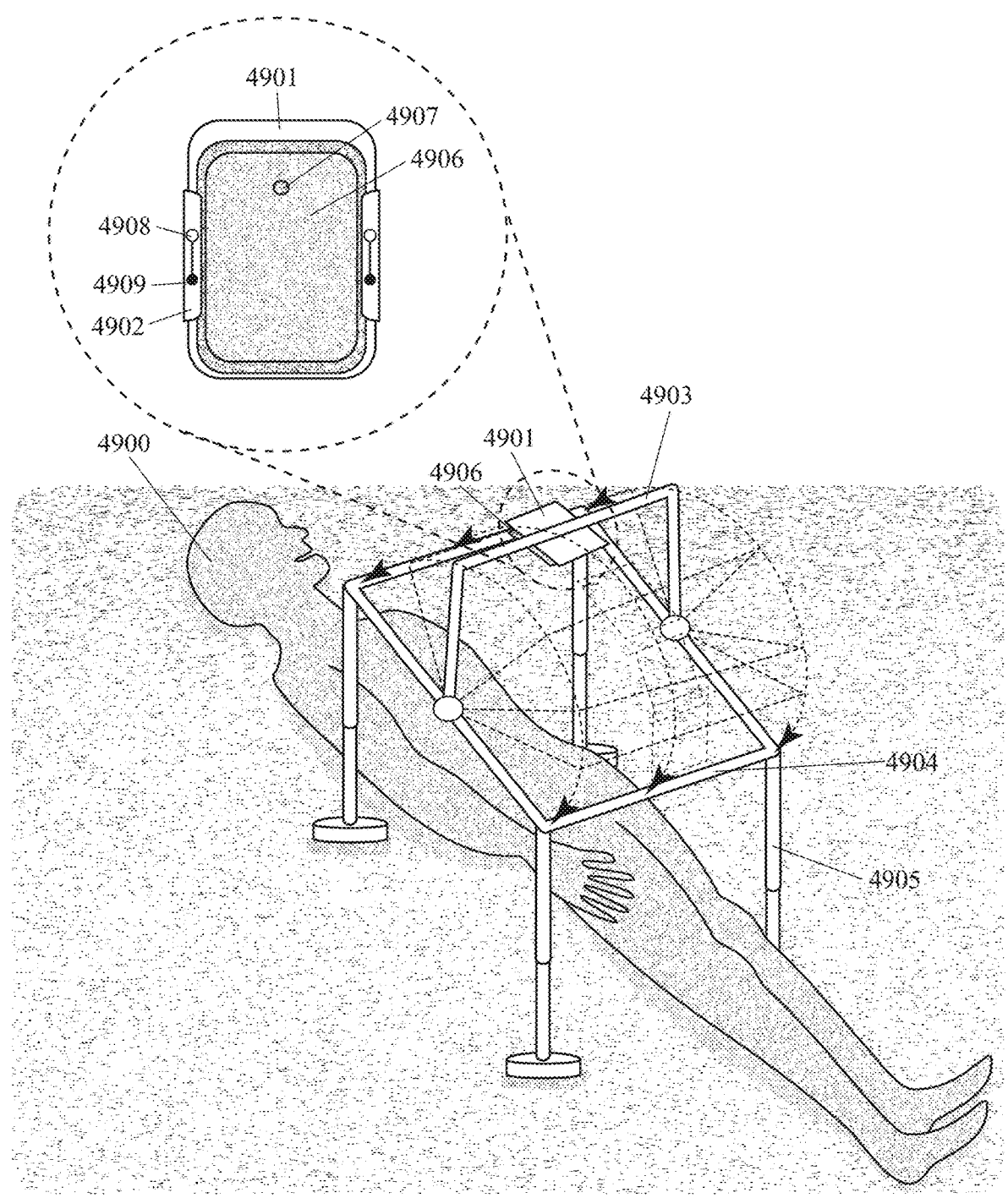

FIGS. 49 and 50 show views at two different times of another example of a portable phone-moving device comprising: a portable phone-moving device; wherein the phone-moving device further comprises an attachment mechanism which holds a camera-enabled mobile phone on the device; and wherein the phone-moving device moves the phone over and/or around a selected portion of a person's body to guide the capturing of phone images of that portion from different angles and/or distances for medical purposes. This design features a pivoting "soccer-goal-frame-shaped" arm which holds and moves a phone in an arcuate (e.g. semicircular) path over a person's body to capture images of the person's body from different angles and/or distances. FIG. 49 shows this device at a first time wherein a person is lying beneath the device at a first orientation, wherein the device scans (images) the person in a lateral (side-to-side) manner. FIG. 50 shows this device at a second time wherein the person is lying beneath the same device at a second orientation, wherein the device scans (images) the person in a longitudinal (head-to-foot) manner.

Specifically, FIGS. 49 and 50 shows views at two different times of a portable phone-moving device comprising: a portable phone-moving device; wherein the phone-moving device further comprises an attachment mechanism which holds a camera-enabled mobile phone on the device; wherein the attachment mechanism further comprises a phone-supporting surface 4901 onto which the phone is attached and at least one clip, clasp, clamp, hook, strap, or magnet 4902 which holds the phone on the phone-supporting surface; a pivoting soccer-goal-posts-shaped arm 4903 over a person's body 4900, wherein the phone-supporting structure is attached to the arm, and wherein the arm is automatically pivoted from a substantially horizontal orientation to a substantially vertical orientation (and/or vice versa); an upper frame 4904 to which the arm is attached; and a plurality of (telescoping) vertical supports 4905 which support the upper frame. In this example, the device further comprises one or more light emitters 4912 and light receivers (or sensors) 4913. FIGS. 49 and 50 also show a conventional mobile phone 4910 with a camera 4911 which is attached to the device. Neither the phone nor the person's body are positively claimed as part of the device.

A soccer-goal-posts-shape can be defined in a less-colloquial (more-technical) manner as an inverted "U" shape or a 90-degree-rotated "C" shape. In an example, a soccer-goal-frame-shaped arm can pivot around the lower ends of its "posts." In an example, the lower ends of the "posts" of the soccer-goal-frame-shaped arm can be movably connected to the upper frame and can pivot around the upper frame. This can move the phone over a person's body in an arcuate path in space which is a section of a circle. In an example, the upper frame can be square or rectangular in shape. As shown in FIGS. 49 and 50, the lower ends of a pivoting soccer-goal-frame-shaped arm can be centrally connected to cross-beams in a square or rectangular upper frame. In an example, an upper frame can be supported by four vertical supports.

As shown in FIGS. 49 and 50, such a device can be configured so that a person's body (or portion of the person's body) can be between two sets of vertical supports. In an example, a person can lie beneath the device in a first orientation for lateral (side-to-side) body scanning (imaging) or can lie beneath the device is a second orientation for longitudinal (head-to-toe orientation) scanning (imaging). In an example, lateral and longitudinal scans of the same portion of a person's body can be digitally combined into a three-dimensional digital image (e.g. 3D digital model) for remote evaluation by a healthcare provider (or a medical AI program).

In an example, the height of this device can be automatically adjusted by expansion or contraction of telescoping vertical supports. In an example, the angle of the phone-supporting surface (and thus the phone) is automatically changed during a scan by pivoting and/or rotation of the arm over the person's body. In an example, all of these device movements can be remotely controlled, in real time, by a non-local (remote) healthcare provider (or a medical AI program). In an example, a device can further comprise one or more components selected from the group consisting of: battery; electromagnetic motor; data processor; wireless data transmitter; and wireless data receiver. Relevant example variations discussed elsewhere in this and priority-linked disclosures can be also applied to this example.

I claim:

1. A portable phone-moving device to guide medical imaging comprising:
   a portable phone-moving device;
   wherein the phone-moving device further comprises an attachment mechanism which holds a camera-enabled mobile phone or other camera-enabled mobile device onto the phone-moving device; and
   wherein the phone-moving device moves the mobile phone or other mobile device over a selected portion of a person's body to guide the capturing of phone images of that portion from different angles and/or distances for medical imaging purposes.

2. The device in claim 1 wherein the device further comprises one or more electromagnetic motors which move the device.

3. The device in claim 1 wherein images of the portion of the person's body from different angles and/or distances are combined to create a digital three-dimensional image of the portion of the person's body which is navigated and viewed by a non-local healthcare provider at a later time.

4. The device in claim 1 wherein movement of the phone by the device is remotely-controlled by a non-local healthcare provider in real time.

5. The device in claim 1 wherein the attachment mechanism is selected from the group consisting of one or more clips, clasps, clamps, hooks, straps, bands, recesses, pockets, magnets, and hook-and-eye materials.

6. The device in claim 1 wherein the device further comprises a phone-supporting surface to which the phone or other mobile device is attached.

7. The device in claim 1 wherein the device further comprises a rotating, pivoting, and/or tilting horizontal arm which rotates, pivots, and/or tilts the phone.

8. The device in claim 1 wherein the device further comprises a rotating, pivoting, and/or tilting vertical arm which rotates, pivots, and/or tilts the phone.

9. The device in claim 1 wherein the device further comprises an arcuate track along which the phone is moved over the portion of the person's body.

10. The device in claim 1 wherein the device further comprises a semicircular track along which the phone is moved over the portion of the person's body.

11. The device in claim 1 wherein the device further comprises an extension mechanism which moves the phone closer to, or father from, the device.

12. The device in claim 1 wherein the device further comprises a cantilevered arm which holds the phone out over the portion of the person's body.

13. The device in claim 1 wherein the device further comprises an arm which holds the phone out over the portion of the person's body wherein there is a counterweight on the portion of the arm opposite the portion of the arm which holds the phone.

14. The device in claim 1 wherein the device further comprises one or more motorized telescoping members which change the height of the device.

15. The device in claim 1 wherein the device further comprises one or more motorized telescoping members which change the width of the device.

16. The device in claim 1 wherein the device further comprises motorized wheels which move the device.

17. The device in claim 1 wherein the device further comprises motorized caterpillar treads which move the device.

18. The device in claim 1 wherein the device further comprises a motorized articulated robotic arm with at least three articulated segments and wherein the phone is attached to the robotic arm.

19. The device in claim 1 wherein the device further comprises a motorized gooseneck robotic arm and wherein the phone is attached to the robotic arm.

20. The device in claim 1 wherein the device further comprises one or more light emitters.

* * * * *